US008674063B2

(12) United States Patent
Chinea Santiago et al.

(10) Patent No.: US 8,674,063 B2
(45) Date of Patent: Mar. 18, 2014

(54) CHIMERICAL PEPTIDIC MOLECULES WITH ANTIVIRAL PROPERTIES AGAINST THE VIRUSES OF THE FLAVIVIRIDAE FAMILY

(75) Inventors: Glay Chinea Santiago, Ciudad de la Habana (CU); Vivian Huerta Galindo, Ciudad de la Habana (CU); Alejandro Miguel Martin Dunn, Ciudad de la Habana (CU); Noralvis Fleitas Salazar, La Habana (CU); Osmany Guirola Cruz, Ciudad Habana (CU); Patricia Gabriela Toledo Mayora, Ciudad de la Habana (CU); Mónica Sarría Núñez, Ciudad de la Habana (CU); Alexis Musacchio Lasa, La Habana (CU); Olvaldo Reyes Acosta, Ciudad de la Habana (CU); Hilda Elisa Garay Pérez, Ciudad de la Habana (CU); Anìa Cabrales Rico, Ciudad Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 703 days.

(21) Appl. No.: 12/513,085

(22) PCT Filed: Oct. 30, 2007

(86) PCT No.: PCT/CU2007/000020
§ 371 (c)(1),
(2), (4) Date: Jun. 16, 2010

(87) PCT Pub. No.: WO2008/052490
PCT Pub. Date: May 8, 2008

(65) Prior Publication Data

US 2010/0273702 A1 Oct. 28, 2010

(30) Foreign Application Priority Data

Oct. 30, 2006 (CU) .................................. 2006-0207

(51) Int. Cl.
*C07K 14/00* (2006.01)

(52) U.S. Cl.
USPC .............................. 530/324; 514/3.7; 514/4.3

(58) Field of Classification Search
USPC .................................... 530/324; 514/3.7, 4.3
See application file for complete search history.

(56) References Cited

U.S. PATENT DOCUMENTS

| | | | | |
|---|---|---|---|---|
| 7,034,109 | B2 * | 4/2006 | Bonny | 530/330 |
| 7,279,164 | B2 | 10/2007 | Hermida Cruz et al. | |
| 2004/0259224 | A1 | 12/2004 | Gulirakhoo | |

FOREIGN PATENT DOCUMENTS

| | | | |
|---|---|---|---|
| EP | 0474313 | A2 | 3/1992 |
| EP | 1418180 | A2 | 5/2004 |
| EP | 1454988 | A1 | 9/2004 |
| WO | WO9306214 | A1 | 4/1993 |
| WO | WO 96/37221 | A1 | 11/1996 |
| WO | WO 97/26359 | A1 | 7/1997 |
| WO | WO9743310 | A1 | 11/1997 |
| WO | WO9823754 | A1 | 6/1998 |
| WO | WO 9831814 | A1 | 7/1998 |
| WO | WO9907733 | A2 | 2/1999 |
| WO | WO9918216 | A2 | 4/1999 |
| WO | WO 00/66791 | A1 | 11/2000 |
| WO | WO2004052293 | A2 | 6/2004 |
| WO | WO2005002501 | A2 | 1/2005 |
| WO | WO2006078657 | A2 | 7/2006 |
| WO | WO2006136697 | A2 | 12/2006 |
| WO | WO2007124698 | A2 | 11/2007 |

OTHER PUBLICATIONS

Database UniProt (online) Subname: Full=Polyprotein; XP002492705 retrieved from EBI accession No. UNIPROT: Q2QFY7 Database accession No. Q2QFY7 the whole document (Jan. 24, 2006).
Shiryaev Sergey A et al., "Cleavage Targets and the D-Arginine-Based Inhibitors of the West Nile Virus NS3 Processing Proteinase", Biochemical Journal, vol. 393, No. Part 2, 503-511 (2006).
Portal-Nunez S. et al., "Peptide Inhibitors of Hepatitis C Virus NS3 Protease" Antiviral Chemistry & Chemotherapy, Blackwell Scientific Publ. London, GB, vol. 14, No. 5, 225-233 (2003).
Deshayes S. et al., "Cell-Penetrating Peptides: Tools for Intracellular Delivery of Therapeutics", CMLS Cellular and Molecular Live Sciences, Birkhauser-Verlag, BA, vol. 62, No. 16, 1839-1849 (2005).
Blok, J., et al., "Variation of the Nucleotide and Encoded Amino Acid Sequences of the Envelope Gene from Eight Dengue-2 Viruses", Archives of Virology 1989, 105(1-2):39-53.
Lanciotti, Robert S., et al., "Molecular evolution and epidemiology of dengue-3 viruses", Journal of General Virology 1994, 75(1):65-75.
Lanciotti, Robert S., et al., "Molecular evolution and phylogeny of dengue-4 viruses", Journal of General Virology 1997, 78(9):2279-2286.
Silva, Ricardo, et al., "Characterisation of the 1pdA gene from *Neisseria meningitidis* by polymerase chain reaction, restriction fragment length polymorphism and sequencing", FEMS Microbiology Letters May 1999, 174 (1):191-199.
Tettelin, Herve, et al., "Complete Genome Sequence of *Neisseria meningitidis* Serogroup B Strain MC58", Science 2000, 287(5459):1809-1815.
Wang, Eryu, et al., "Evolutionary Relationships of Endemic/Epidemic and Sylvatic Dengue Viruses", Journal of Virology 2000, 74(7):3227-3234.

(Continued)

*Primary Examiner* — David Lukton
(74) *Attorney, Agent, or Firm* — Hoffmann & Baron, LLP

(57) ABSTRACT

The present invention is relative to chimerical peptides, whose primary structure holds at least one segment which inhibits the activation of the NS3 protease of a virus from the Flaviviridae family, they also contain a cell penetrating segment and they are capable of inhibiting or attenuate the viral infection. This invention is also relative to pharmaceutical compounds which contain these chimerical peptides for the prevention and/or treatment of the infection caused by a virus of the Flaviviridae family.

15 Claims, 5 Drawing Sheets

(56) References Cited

OTHER PUBLICATIONS

Chaturvedi et al., "Dengue Vaccines: Problems and Prospects," Indian J. Med. Res. vol. 121, May 2005, pp. 639-652.
Perez et al., "Safety and Preliminary Immunogenicity of the Recombinant Outer Membrane Protein P64K of *Neiseria meningitis* in Human Volunteers," Biotechnol. Appl. Biochem, 34, 121-125 (2001).
Pugachev et al., "New Developments in Flavivirus Vaccines with Special Attention to Yellow Fever," Curr Opin Infect Dis 18:387-394 (2005).
Murray, et al., "Processing of the Dengue Virus Type 2 Proteins prM and C-prM", Journal of General Virology, 74, 175-182 (1993).
Srivastava et al., "Mice Immunized with a Dengue Type 2 Virus E and NS1 Fusion Protein Made in *Escherichia coli* are Protected Against Lethal Dengue Virus Infection," Vaccine vol. 13, No. 13 (1995).
Goncalvez et al., "Epitope Determinants of a Chimpanzee Fab Antibody that Efficiently Cross-Neutralizes Dengue Type 1 and Type 2 Viruses Map to Inside and in Close Proximity to Fusion Loop of the Dengue Type 2 Virus Envelope Glycoprotein", Journal of Virology, 78(23):12919-12928(2004).
Mason et al., "The Antigenic Structure of Dengue Type I Virus Envelope with NS1 Proteins Expressed in *Escherichia Coli*", Journal of General Virology, 71, 2107-2114(1990).
Mota et al., "Induction of Protective Antibodies Against Dengue Virus by Tetravalent DNA Immunization of Mice with Domain III of the Envelope Protein", Vaccine 23, 3469-3476(2005).
Thullier et al., "A recombinant Fab Neutralizes Dengue Virus in Vitro", Journal of Biotechnology, Elsevier Science Publishers, vol. 69, No. 2-3, pp. 183-190 (1999) Abstract.
Monath, T. "Dengue and Yellow Fever—Challenges for the Development and Uses of Vaccines", N.Engl J. Med 357:222222-2225 (2007).
Mustafa et al., "Dengue Vaccine The Current Status", MJAFI, vol. 64, No. 2, 161-164 (2008).
Shresta, et al., "Murine Model for Denjue Virus-Induced Lethal Disease with Increased Vascular Permeability", Journal of Virology, 80:20, 10208-10217 (2006).
Irie et al., "Sequence analysis of cloned dengue virus type 2 genome (New Guinea-C strain)", Department of Biochemistry and Molecular Biology, University of Kansas Medical Center, Gene 75 197-211 (1989).
Gruenberg et al., "Partial Nucleotide Sequence and Deduced Amino Sequence of the Structural Proteins of Dengue Virus Type 2, New Guinea C and PUO-218 Strains", J. gen Virol. 69, 1391-1398 (1988).
Zhao et al., "Cloning Full-Length Dengue Type 4 Viral DNA Sequences: Analysis of Genes Coding for Structural Proteins", Virol. 155:77-88 (1986).
Gaines et al., "Pathogen-Derived Resistance to Dengue Type 2 Virus in Mosquito Cells by Expression of the Premembrane Coding Region of the Viral Genome", Journal of Virology, p. 2132-2137 (1996).
Kaufman et al., "Monoclonal Antibodies for Dengue Virus PRM Glycoprotein Protect Mice Against Lethal Dengue Infection", Am. J. Trop. Med. Hyg., 41(5), pp. 576-580 (89-157) 1989.
Bray et al., "Dengue Virus Premembrane and Membrane Proteins Elicit a Protection Immune Response", Virology, 185, 505-508 (1991).
Randolph et al., "Acidotropic Amines Inhibit Proteolytic Processing of Flavivirus prM Protein", Virology 174, 450-458 (1990).

* cited by examiner

Figure 1A.

```
                10        20        30        40        50
DEN2J SWPLNEAIMAVGMVSILASSLLKNDIPMTGPLVAGGLLTVCYVLTGRSADLELERAADVK 60
DEN3  SWPLNEGVMAVGLVSILASSLLRNDVPMAGPLVAGGLLIACYVITGTSADLTVEKAADVT 60
DEN1S SWPLNEGIMAVGIVSILLSSLLKNDVPLAGPLIAGGMLIACYVISGSSADLSLEKAAEVS 60
DEN4  SWPLNEGIMAVGLVSLLGSALLKNDVPLAGPMVAGGLLLAAYMMSGSSADLSLEKAANVQ 60
MVEV  -WPATEVLTAVGLMFAIVGGLAELDISMSVPFTIAGLMLVSYVISGKATDMWLERAADVS 59
YEFV2 SIPVNEALAAAGLVGVLAGLAFQEMENFLGPIAVGGLLMMLVSVAGRVDGLELKKLGEVS 60
YEFV1 SIPVNEALAAAGLVGVLAGLAFQEMENFLGPIAVGGLLMMLVSVAGRVDGLELKKLGEVS 60
STEVM SWPASEVLTGVGLMCALAGGLLEEETSMVVPFAIAGLMYITYTVSGKAAEMWIEKAADIT 60
JAEV1 -WPATEFLSAVGLMFAIVGGLAELDISMSIPFMLAGLMAVSYVVSGKATDMWLERAADIS 59
JAEVN -WPATEFLSAVGLMFAIVGGLAELDISMSIPFMLAGLMAVSYVVSGKATDMWLERAADIS 59
KUNJM -WPATEVMTAVGLMFAIVGGLAELDISMAIPMTIAGLMFAAFVISGKSTDMWIERTADIS 59
WNV   -WPATEVMTAVGLMFAIVGGLAELDISMAIPMTIAGLMFAAFVISGKSTDMWIERTADIT 59
POWVL RRSLSEPLTVVGVMLAMASGLLRHSSEALLALSAGSFLILMLILGTRRLQLTAEWAGVVE 60
         . .* : .*:: : .     .      .: .. :     :     ::     :

                70        80        90       100       110
DEN2J WEDQAEISGSSPILSITISEDGSMSIKNEEEEQTLTILIRTGLLVISGVFPVSIPITAAA 120
DEN3  WEEEAEQTGVSHNLMITVDDDGTMRIKDDETENILTVLLKTALLIVSGIFPYSIPATMLV 120
DEN1S WEEEAEHSGASHNILVEVQDDGTMKIKDEERDDTLTILLKATLLAVSGVYPLSIPATLFV 120
DEN4  WDEMADITGSSPIIEVKQDEDGSFSIRDVEETNMITLLVKLALITVSGLYPLAIPVTMTL 120
MVEV  WEAGAAITGTSERLDVQLDDDGDFHLLNDPGVPWKIWVLRMTCLSVAAITPWAILPSAFG 119
YEFV2 WEEEAEISGSSARYDVALSEQGEFKLLSEEKVPWDQVVMTSLALVGAALHPFALLLVLAG 120
YEFV1 WEEEAEISGSSARYDVALSEQGEFKLLSEEKVPWDQVVMTSLALVGAALHPFALLLVLAG 120
STEVM WEQNAEITGTSPRLDVDLDSHGNFKLLNDPGAPVHLFALRFILLGLSARFHWFIPFGVLG 120
JAEV1 WEMDAAITGSSRRLDVKLDDDGDFHLIDDPGVPWKVWVLRMSCIGLAALTPWAIVPAAFG 119
JAEVN WEMDAAITGSSRRLDVKLDDDGDFHLIDDPGVPWKVWVLRMSCIGLAALTPWAIVPAAFG 119
KUNJM WEGDAEITGSSERVDVRLDDDGNFQLMNDPGAPWKIWMLRMACLAISAYTPWAILPSVVG 119
WNV   WESDAEITGSSERVDVRLDDDGNFQLMNDPGAPWKIWMLRMACLAISAYTPWAILPSVIG 119
POWVL WNPELVNEGGEVSLKVRQDAMGNLHLTEVEREERRLALWLVFGLLASAYHWSGILVTMGA 120
      *:       *.      :  . *::.                 : :.      :

DEN2J WYLWEVKKQR 130
DEN3  WHTWQKQTQR 130
DEN1S WYFWQKKKQR 130
DEN4  WYMWQVKTQR 130
MVEV  YWLTLKYTKR 129
YEFV2 WLFHVRGARR 130
YEFV1 WLFHVRGARR 130
STEVM FWLLGKHSKR 130
JAEV1 YWLTLKTTKR 129
JAEVN YWLTLKTTKR 129
KUNJM FWITLQYTKR 129
WNV   FWITLQYTKR 129
POWVL WTVYEL---- 126
      :
```

CHIMERICAL PEPTIDIC MOLECULES WITH ANTIVIRAL PROPERTIES AGAINST THE VIRUSES OF THE FLAVIVIRIDAE FAMILY

This application is the U.S. National Phase of, and Applicants claim priority from, International Application Number PCT/CU2007/000020 filed 30 Oct. 2007 and Cuban Application bearing Serial No. 2006-0207 filed 30 Oct. 2006, which are incorporated herein by reference.

FIELD OF THE INVENTION

The present invention is relative to the pharmaceutical industry, more specifically to chimerical peptides, whose primary structure holds at least a segment which inhibits the NS3 protease of a virus from the Flaviviridae family, they also includes a cell penetrating segment and they are capable to inhibit or attenuate the viral infection. The invention is also relative to pharmaceutical compounds which contain the chimerical peptides for the prevention and/or treatment of the infection caused by viruses from the Flaviviridae family.

DESCRIPTIVE MEMORY

The Flaviviridae family is constituted by enveloped positive single-stranded RNA viruses, which belong to one of three genera: Flavivirus, Hepacivirus and Pestivirus. The Flavivirus genus includes more than 70 virus, many of them cause relevant diseases in humans and in other species. Members of this genus are the Yellow Fever Virus (YFV), Dengue Virus (DV), Japanese Encephalitis Virus (JEV), Tick-borne Encephalitis Virus (TBE), West-Nile Virus (WNV), St. Louis Encephalitis Virus (SLEV) and others. The Hepatitis C virus (HCV) is the prototype of the Hepacivirus. As members of the genus Pestivirus we find the Bovine Viral Diarrhea virus (BVDV), the Classical Swine Fever virus (CSFV), Border Disease virus (BDV) and others.

The viruses belonging to different genera of the Flaviviridae family, do not display antigenic cross-reactivity and show diverse biological properties, however they show evident similarities in aspects such as virion morphology, genome organization and the replication strategy (Leyssen, P., De Clercq, E., Neyts, J. 2000 *Perspectives for the treatment of infections with Flaviviridae. Clin Microbiol Rev.,* 3: 67-82; Rice, C. M. 1996. *Flaviviridae: the viruses and their replication, p.* 931-960. In B. N. Fields, D. M. Knipe, and P. M. Howley (ed.), *Fields virology,* $3^{rd}$ ed., vol. 1. Lippincott-Raven Publishers, Philadelphia, Pa.; Westaway, E. G. 1987. *Flavivirus replication strategy. Adv. Virus Res.* 33:45-90)

The HCV constitutes an important health problem worldwide. According to the WHO about 3% of the world population has been infected by the virus, indicating that more than 170 millions of chronic carriers are in risk of developing cirrhosis and/or liver cancer (*Consensus Panel. EASL International Consensus Conference on Hepatitis C, Paris,* 26-28 Feb. 1999*, Consensus Statement. J. Hepatol.,* 1999, 30, 956). Every year about 3-4 millions new infections by HCV arise worldwide (Tan, S. L., Pause, A., Shi, Y. & Sonenberg, N. (2002) *Nat. Rev. Drug Discov.* 1, 867-881). At least 85% of the infected patients evolves to a chronic infection (Alter, M. J., E. E. Mast, L. A. Moyer, and H. S. Margolis. 1998. *Hepatitis C. Infect. Dis. Clin. North Am.* 12:13-26). The chronic Hepatitis C frequently ends in cirrhosis and/or cancer, whether it is symptomatic or asymptomatic. Follow-up studies carried out for 10-20 years show development of cirrhosis in 20-30% of the patients, and 1-5% of these patients could develop cancer in the following 10 years (Dutta, U., J. Kench, K. Byth, M. H. Khan, R. Lin, C. Liddle, and G. C. Farrell. 1998. *Hepatocellular proliferation and development of hepatocellular carcinoma: a case-control study in chronic hepatitis C. Hum. Pathol.* 29:1279-1284; Pontisso, P., C. Belluco, R. Bertorelle, L. De Moliner, L. Chieco Bianchi, D. Nitti, M. Lise, and A. Alberti. 1998. *Hepatitis C virus infection associated with human hepatocellular carcinoma: lack of correlation with p53 abnormalities in Caucasian patients. Cancer* 83:1489-1494). It is estimated that the number of deaths per year caused by HCV in the United States can reach 35000 by the year 2008 (Dutta, U., J. Kench, K. Byth, M. H. Khan, R. Lin, C. Liddle, and G. C. Farrell. 1998. *Hepatocellular proliferation and development of hepatocellular carcinoma: a case-control study in chronic hepatitis C. Hum. Pathol.* 29:1279-1284; Pontisso, P., C. Belluco, R. Bertorelle, L. De Moliner, L. Chieco Bianchi, D. Nitti, M. Lise, and A. Alberti. 1998. *Hepatitis C virus infection associated with human hepatocellular carcinoma: lack of correlation with p53 abnormalities in Caucasian patients. Cancer* 83:1489-1494.).

Currently, the anti-HCV treatments approved by the FDA are the interferon monotherapy and the interferon-ribavirin combined therapy (Dymock, B. W. *Emerging Drugs* 2001, 6(1), 13 and references within). Recently, the use of pegylated interferon variants have been approved, which increase the therapeutic efficacy of these treatments, but they are still far from being ideals. Because of the seriousness of this disease, new and more effective treatments are needed.

The Flavivirus infecting human beings are transmitted by arthropods such as ticks and mosquitoes, which makes these diseases so difficult to eradicate (Monath, T. P., and F. X. Heinz. 1996. *Flaviviruses, p.* 961-1034. In B. N. Fields, D. M. Knipe, and P. M. Howley (ed.), *Fields virology,* 3rd ed., vol. 1. Lippincott-Raven Publishers, Philadelphia, Pa.). The Yellow Fever is still an important cause of hemorrhagic fever, with mortality rates as high as 50%, although a vaccine is already available.

The Dengue Virus is pandemic in tropical areas and its re-emergence is an increasing public health problem worldwide. It is estimated that annually occur approximately 100 million infections by dengue virus and 2.5 milliard persons live in endemic areas (Gubler, D. J. 1998. *Clin. Microbiol. Rev.* 11, 480-496; Monath, T. P. (1994) *Proc. Natl. Acad. Sci. USA* 91, 2395-2400.) During the period 1990-1998, the average number of Dengue Hemorrhagic Fever (DHF) cases reported to the WHO was 514 139 per year, including 15 000 deaths, although it is considered that the real burden of the disease is some times higher. However, neither vaccines nor specific antiviral treatments are commercially available. The dengue virus complex is conformed by four distinct viruses or serotypes (VD1-VD4), which are related genetically and antigenically. The DV is transmitted to humans by the mosquitoes, mainly by the *Aedes aegypti*. The infection causes diverse clinical manifestations varying from asymptomatic and benign to an undifferentiated febrile illness or more severe manifestations like the DHF and the potentially lethal Dengue Shock Syndrome (DSS). The most severe clinical manifestations are frequently associated to sequential infections with two different serotypes (Halstead, S. B. *Neutralization and antibody-dependent enhancement of dengue viruses. Adv. Virus Res.* 60:421-67., 421-467, 2003. *Hammon WMc. New haemorragic fever in children in the Philippines and Thailand. Trans Assoc Physicians* 1960; 73: 140-155). Epidemiological studies have been carried out showing evidences of sequential infection with different serotypes as a risk factor for severe disease (Halstead, S. B. *Neutralization*

*and antibody-dependent enhancement of dengue viruses. Adv. Virus Res.* 60:421-67., 421-467, 2003. *Hammon WMc. New haemorragic fever in children in the Philippines and Thailand. Trans Assoc Physicians* 1960; 73: 140-155). This phenomena has been explained through the theory of the "antibody dependent enhancement (ADE)", which postulates that an increase in infectivity is associated with a more efficient cell entry of the virus mediated by FC receptor of the infected cells (Halstead S B. *Pathogenesis of dengue: challenges to molecular biology. Science* 1988; 239: 476-481).

Other Flavivirus is the JEV, which is the main cause of viral encephalitis worldwide. About 50000 cases occur annually in Asia with a high mortality rate of 30% and causing long lasting neurological disorders in 30% of cases (Kalita, J., and U. K. Misra. 1998. *EEG in Japanese encephalitis: a clinico-radiological correlation. Electroencephalogr. Clin. Neurophysiol.* 106:238-243; Kaluzova, M., E. Eleckova, E. Zuffova, J. Pastorek, S. Kaluz, O. Kozuch, and M. Labuda. 1994. *Reverted virulence of attenuated tick-borne encephalitis virus mutant is not accompanied with the changes in deduced viral envelope protein amino acid sequence. Acta Virol.* 38:133-140).

Severe encephalitis is also caused by other Flaviviruses like the TBEV, being two subtypes of this virus: the eastern type with an associated mortality of 20% and the western type with 1-2% (Heinz, F. X., and C. W. Mandl. 1993. *The molecular biology of tick-borne encephalitis virus. APMIS* 101:735-745); the Murray Valley Encephalitis (MVE) in Australia (Mackenzie, J. S., and A. K. Broom. 1995. *Australian X disease, Murray Valley encephalitis and the French connection. Vet. Microbiol.* 46:79-90); the SLEV in the western United States and the WNV, which is endemic in Africa, Middle East and the Mediterranean and has also caused recent outbreaks in the United States. Since it appeared in the United States in 1999, it has expanded very fast, infecting about 15 000 persons and leading to more than 600 deaths. However, currently there are not available vaccines or drugs which protect against the WNV (van der Meulen, K. M., Pensaert, M. B. and Nauwynck, H. J. (2005) *West Nile virus in the vertebrate world. Arch. Virol.* 150, 637-657).

Hemorrhagic manifestations are caused by other Flaviviruses like the Omsk Hemorrhagic Fever Virus (OHFV) in Russia, with a lethality rate between 0.5-3% and the Kyasanur Forest Disease Virus (KFDV) in India (Monath, T. P., and F. X. Heinz. 1996. *Flaviviruses, p.* 961-1034. In B. N. Fields, D. M. Knipe, and P. M. Howley (ed.), *Fields virology,* 3rd ed., vol. 1. Lippincott-Raven Publishers, Philadelphia, Pa.).

Other Flavivirus, the Louping ill virus (LIV) infects mainly sheep, although occasional human infections have also been reported (Davidson, M. M., H. Williams, and J. A. Macleod. 1991. *Louping ill in man: a forgotten disease. J. Infect.* 23:241-249).

The Pestivirus BVDV, CSFV and BDV cause important diseases in animals. In their respective hosts the cause severe affections which usually lead to death, although these viruses can cross species causing a milder disease in other hosts. Frequently, infections occur by oronasal or transplacental route. The latter is responsible of persistent infections which are a threat for the rest of the livestock (Edwards, S., P. M. Roehe, and G. Ibata. 1995. *Comparative studies of border disease and closely related virus infections in experimental pigs and sheep. Br. Vet. J.* 151:181-187).

It is presumed that the members of the Flaviviridae family share a similar replication strategy. The viral replication cycle begins with the adhesion of the virus to the host cell surface. In the case of Dengue virus, it has been shown that the virus binds to glycosaminoglycans, which could be the initial site of interaction with the cells. It has been also shown that the virus binds to DC-SIGN, although it is likely that the role of these molecules is related to the viral concentration on the cell surface or in the spread of the virus to secondary replication sites in vivo. After the initial binding, the virus interacts with high affinity receptors and/or co-receptors, which mediate the virus entry into the cell by endocytosis. In the case of the WNV, it has been postulated that the $\alpha_v\beta_3$ integrin could serve to these means (Chu, J. J-H., and Ng, M.-L., 2004. *Interaction of West Nile Virus with $\alpha_{v\beta3}$ Integrin Mediates Virus Entry into Cells. J. Biol. Chem.* 279, 54533-54541). It has also been shown that the HCV binds to the cellular receptor CD81 (Pileri, P., Y. Uematsu, S. Campagnoli, G. Galli, F. Falugi, R. Petracca, A. J. Weiner, M. Houghton, D. Rosa, G. Grandi, and S. Abrignani. 1998. *Binding of hepatitis C virus to CD*81. *Science* 282:938-941). Once the virus is localized in the endocytic compartments, a drop in the compartment pH induces the fusion process between the viral and the cell membrane, and this process is mediated by structural changes of the fusion protein of the virus envelope. This process leads to the discharge of the virus capsid into the cytoplasm, where the viral RNA is later released.

In the cytoplasm the genomic RNA of the virus, interacts through its non-coding 5' region (5'UTR) with the ribosome, leading to the translation of the virus unique open reading frame. This way, the precursor viral polyprotein is synthesized, which in the case of Flaviviruses includes three structural proteins (C, preM and E) and five non structural proteins (NS1-5). This polyprotein is then modified co- and post-translationally giving rise to the individual mature functional proteins of the virus. The RNA-dependent RNA-polymerase of the virus with associated cofactors produces copies of negative-single stranded RNA, which are later used as templates for the synthesis of the genomic positive-single stranded viral RNA. The viral proteins participating in the replication are associated to membranous structures apparently related to the endoplasmic reticulum (ER).

After the replication is completed, the genomic RNA associates with the nucleocapsid, the immature virions bud into the lumen of the ER (budding occurs at the membrane of the ER or related membranous structures induced by the virus), covered by a lipid envelope containing viral proteins. Passing through the exocytic pathway, the envelope proteins are glycosilated and become mature, leading to the final release of the mature virions to the extracellular space.

The replication of the Flaviviriae requires the NS3pro protease (localized approximately in the first 180 residues of the non structural protein NS3) for the correct processing of the precursor polyprotein, this way constituting an attractive potential target for the design of antiviral drugs (Chappell, K. J., Nall, T. A., Stoermer, M. J., Fang, N. X., Tyndall, J. D., Fairlie, D. P. and Young, P. R. (2005) *Site-directed mutagenesis and kinetic studies of the West Nile Virus NS*3 *protease identify key enzyme-substrate interactions. J. Biol. Chem.* 280, 2896-2903. SHIRYAEV, S. A., RATNIKOV, B. I., CHEKANOV, A. V., SIKORA, S., ROZANOV, D. V., GODZIK, A., WANG, J., SMITH, J. W., HUANG, Z., LINDBERG, I., SAMUEL, M. A., DIAMOND, M. S. and Alex Y. STRONGIN, A. Y., 2006. *Cleavage targets and the D-arginine-based inhibitors of the West Nile virus NS*3 *processing proteinase. Biochem. J.* 393, 503-511. Kolykhalov, A. A.; Mihalik, K.; Feinstone, S. M.; Rice, C. M. *J. Virol.* 2000, 74, 2046; Bartenschlager, R.; Lohmann, V. *J. Gen. Virol.* 2000, 81, 1631. Matusan, A. E., Kelley, P. G., Pryor, M. J., Whisstock, J. C., Davidson, A. D. and Wright, P. J. (2001) *J. Gen. Virol.* 82, 1647-1656).

In Flavivirus this protease is responsible for the proteolytic cleavage at the junctions NS2A/NS2B, NS2B/NS3, NS3/NS4A and NS4N/NS5, as well as the internal cleavage in C, NS3 and NS4A (Chambers, T. J., Nestorowicz, A., Amberg, S. M. and Rice, C. M. (1993) *Mutagenesis of the yellow fever virus NS2B protein: effects on proteolytic processing, NS2B-NS3 complex formation, and viral replication. J. Virol.* 67, 6797-6807. Jan, L. R., Yang, C. S., Trent, D. W., Falgout, B. and Lai, C. J. (1995) *Processing of Japanese encephalitis virus non-structural proteins: NS2B-NS3 complex and heterologous proteases. J. Gen. Virol.* 76, 573-580. Lobigs, M. (1993) *Flavivirus premembrane protein cleavage and spike heterodimer secretion require the function of the viral proteinase NS3. Proc. Natl. Acad. Sci. U.S.A.* 90, 6218-6222. Yamshchikov, V. F. and Compans, R. W. (1994) *Processing of the intracellular form of the west Nile virus capsid protein by the viral NS2B-NS3 protease: an in vitro study. J. Virol.* 68, 5765-5771).

In HCV, NS3pro mediates the proteolytic processing of the viral polyprotein in the segment comprised between the proteins NS2-NS5B (R. Bartenschlager, 1999, *The NS3/4A proteinase of the hepatitis C virus: unravelling structure and function of an unusual enzyme and a prime target for antiviral therapy. J. Viral Hepat.* 6, 165).

Besides the central role played by the NS3pro protease in the viral replication cycle processing the virus proteins, this protein can also process cellular substrates and hence it could be involved in various mechanisms of cellular damage and pathogenesis (Shiryaev, S. A., Ratnikov, B. I., Chekanov, A. V., Sikora, S., Rozanov, D. V., Godzik, A., Wang, J., Smith, J. W, Huang, Z., Lindberg, I., Samuel, M. A., Diamond, M. S, and Strongin, A. Y. (2005) *The cleavage targets and the (D)-arginine-based inhibitors of the West Nile virus NS3 processing proteinase. Biochem. J.* 393, 503-511).

Thus, it has been shown that the NS3 protease from WNV produces proteolytic cleavage in neuronal myelin basic protein (MBP). Regarding DV and WNV, it has been suggested that NS3 is involved in the induction of virus mediated apoptosis (Ramanathan, M. P., Chambers, J. A., Pankhong, P., Chattergoon, M., Attatippaholkun, W., Dang, K., Shah, N. and Weiner, D. B. (2005) *Virology doi:*10/1016/*j.virol.* 2005.08.043)

For its optimal function, the NS3 protease needs to interact with other viral protein or cofactor, the NS2B protein in Flavivirus and NS4A in Hepacivirus and Pestivirus. In DV the presence of NS2B induces an increase in the proteolytic activity of NS3 between 3300 and 6600 times (Yusof, R., Clum, S., Wetzel, M., Murthy, H. M. & Padmanabhan, R., 2000. *J. Biol. Chem.* 275, 9963-9969).

In HCV, NS3 binding to NS4A is required for the proteolytic cleavage at NS3/4A, NS4A/B and NS4B/5A and it increases the efficiency of the processing at the junction NS5A/B (Bartenschlager R, Ahlborn L L, Mous J, Jacobsen H. *Kinetic and structural analyses of hepatitis C virus polyprotein processing. J Virol* 1994; 6: 5045-5055. Fulla C, Tomei L, De Francesco R. *Both NS3 and NS4A are required for proteolytic processing of hepatitis c virus nonstructural proteins. J Virol* 1994; 6: 3753-3760. Lin C, Pragai B M, Grakoui A, Xu J, Rice C M. *Hepatitis C virus NS3 serine proteinase: trans-cleavage requirements and processing kinetics. J Virol* 1994; 6: 8147-8157. Tanji Y, Hijikata M, Satoh S, Kaneko T, Shimotohno K. *Hepatitis C virus-encoded nonstructural protein NS4A has versatile functions in viral protein processing. J Virol* 1995; 6: 1575-1581). The addition of a NS4A fragment to NS3pro in a 10 times molar excess increases the catalytic efficiency coefficient $K_{cat}/K_m$ in approximately 40 times (SHIMIZU, Y., YAMAJI, K., MASUHO, Y., YOKOTA, T., INOUE, H., SUDO, K., SATOH, S. y SHIMOTOHNO, K. 1996. *Identification of the Sequence on NS4A Required for Enhanced Cleavage of the NS5A/5B Site by Hepatitis C Virus NS3 Protease. J. Virol* 70, 127-132).

The crystal structures of NS3pro and the NS3pro-NS2B complex from DV and the complex formed by NS3pro-NS2B from WNV with a peptide inhibitor have been experimentally determined (Murthy, H. M., Clum, S. & Padmanabhan, R., 1999. *J. Biol. Chem.* 274, 5573-5580. Murthy, H. M., Judge, K., DeLucas, L. & Padmanabhan, R., 2000. *J. Mol. Biol.* 301, 759-767. Erbel P, Schiering N, D'Arcy A, Renatus M, Kroemer M, Lim S P, Yin Z, Keller T H, Vasudevan S G, Hommel U., 2006. *Structural basis for the activation of flaviviral NS3 proteases from dengue and West Nile virus. Nat. Struct Mol. Biol.*). Similarly, the crystal structures of NS3pro and the complex NS3pro/NS4A from HCV have also been determined (Love, R. A., Parge, H. E., Wickersham, J. A., Hostomsky, Z., Habuka, N., Moomaw, E. W., Adachi, T., Hostomska, Z., 1996. *The crystal structure of hepatitis C virus NS3 proteinase reveals a trypsin-like fold and a structural zinc binding site. Cell.* 87, 331-342. Kim, J. L., Morgenstern, K. A., Lin, C., Fox, T., Dwyer, M. D., Landro, J. A., Chambers, S. P., Markland, W., Lepre, C. A., O'Malley, E. T., Harbeson, S. L., Rice, C. M., Murcko, M. A., Caron, P. R., Thomson, J. A., 1996. *Crystal structure of the hepatitis C virus NS3* protease domain complexed with a synthetic NS4A cofactor peptide. Cell. 87, 343-535. *Erratum in: Cell,* 89:159, 1997).

The NS3pro protease adopts a chymotrypsin-like fold, which comprises two beta barrels and the His51-Asp75-Ser135 catalytic triad being localized in a crevice created between these domains. The binding of NS2B protein induces large changes in the tridimensional structure of NS3pro, affecting both the N- and C-terminal domains and comprising changes in the location and extend of the secondary structural segments.

The structure of the complex formed by the NS3pro-NS2B active protease with a peptide inhibitor shows that NS2B forms a belt around NS3pro, adopting a mainly extended structure and including five beta strands.

The first three strand are associated to beta strands from NS3 protein: the strand Trp53-Ala58 (WNV numbering) runs antiparallelly to the NS3 beta strand Gly21-Met26 corresponding to the N-terminal beta barrel and the beta strands Glu67-Ile68 and Arg74-Asp76 are parallel to the beta strands B2a y B2b of the NS3 C-terminal beta barrel. The strands 4 and 5 form a beta hairpin, which interacts with the substrate binding site contacting the E1b-F1 loop from the N-terminal beta barrel. The folding of NS2B below the E2b-F2 beta hairpin of the C-terminal barrel induces a conformational change in this region of NS3 which leads to the arrangement of residues important for substrate recognition (Gly151, Gly153 y Tyr161). The residue Tyr161 makes pi-cation interactions with the arginine at P1 position. The negative electrostatic potential associated to the main chain carbonyl groups of residues Asp82-Gly83 and the atom Od1 of Asn84 from NS2B makes it favorable the interaction with the positive charge of the guanidinium group from the arginine at position P2. This way, they contribute to the conformation of the S2 site. Thus, the NS2B binding to NS3 completes essential elements of the enzyme active site and it also contributes to the thermodynamic stability of protein folding. These facts offer a structural basis for understanding the activation process of this protease.

In the case of HCV, NS3 activation is mediated by the binding of the beta strand Thr20-Leu31 from NS4A, which is structurally equivalent to strand 1 of NS2B from Flavivirus (SHIMIZU, Y., YAMAJI, K., MASUHO, Y., YOKOTA, T., INOUE, H., SUDO, K., SATOH, S. y SHIMOTOHNO, K. 1996. *Identification of the Sequence on NS4A Required for Enhanced Cleavage of the NS5A/58 Site by Hepatitis C Virus NS3 Protease. J. Virol* 70, 127-132).

Among the current approaches being carried out to obtain antiviral molecules against Flaviviridae, those based on NS3 inhibition are focused mainly in developing inhibitors targeting the active site. These approaches seem to be very promising, which is supported by recent results achieved in the development of drugs against HCV. However, these experiences have also shown clearly the difficulties inherent to these approaches. One of the more prominent is the generation of escape mutants. The polymerases of RNA viruses have relatively low fidelity and in the case of HCV it introduces a mutant per copy of the virus genome. It results in the fact that molecules developed by this means although they are very potent they could have a limited useful lifetime. It has lead to the introduction of therapeutic interventions based on cocktails of drugs as a need for antiviral treatments. It has also been observed that escape mutants raised against one drug can frequently escape the antiviral activity of other drugs targeting the same active site.

The present invention describes novel methods aimed to the design of antiviral agents against Flaviviridae, which are based in the concept of inhibition of the NS3 protease activation process. The key approach of this concept is the design of peptidic molecules and/or drugs capable of blocking the interaction between NS3 and its cofactor (NS2B or NS4A), and hence being able to interfere with the correct folding of the active NS3 protease. Such molecules are capable to bind to regions of the NS3 protease which are involved in the interaction with the cofactor, and compete with it and/or stabilize the structure of the inactive protease.

An advantage of this invention is that the probability of generation of escape mutants against these molecules is expected to be lower compared to those inhibitors of the active protease which compete with the substrate for the active site. The molecules of the present invention bind to binding sites in NS3 which are involved in protein-protein interactions essential for the viral replication cycle, therefore mutations generated in these regions of NS3 should have additional compensatory mutations in the cofactor.

Other advantage is the high specificity of the inhibitory activity displayed by these molecules. It is due to the fact that its binding sites on NS3 are essentially specific for the viral protease and they are not present on the host serine proteases. Furthermore, the host serine proteases have active sites showing specificities very similar to NS3 and hence they could be potential targets for toxicity of active site blocking drugs.

In the present invention we describe chimerical peptidic molecules which inhibit infections by Flaviviridae, and whose primary structure can be described according the following formula:

$$[P]-[L_1]-[I]-[L_2]-[T] \text{ or } [I]-[L_3]-[P]-[L_4]-[T],$$

where, [P] is the amino acid sequence of a "cell penetrating peptide", typically of 10-30 amino acids, which have the capacity to allow the internalization of the whole peptidic molecule into the cell cytoplasm and to get access to the contiguity of the rough endoplasmic reticulum (RER); [L1, L2, L3, L4], are linker sequences of 0-6 residues; [I], is a NS3pro activation inhibitor sequence, containing residues which make contacts with at least one amino acid from the beta strands B2a and B2b of the C-terminal beta barrel, or from the beta strand A1 of the N-terminal beta barrel of the NS3pro protein from Flavivirus (or the corresponding structurally equivalent regions of Pestivirus or Hepacivirus) in its active or inactive conformation; [T], amino acid sequence between 0 and 10 residues, which is typically one or two signals of retention in the ER (like the sequences KDEL, KKXX and LRRRRL), or the sequence XRR with the capability to bind the P1 and P2 substrate binding sites of the NS3pro protease of Flavivirus.

More specifically, we have shown that peptides which have been designed according to the present invention are capable of inhibit the viral infection by DV.

Cationic Cell Penetrating Peptides

The present invention describes the design of chimerical peptides which are capable to inhibit the viral infection of viruses from the Flaviviridae family. The designed peptides contain an [I] segment, which inhibit the activation of the viral NS3pro protease. However, in this invention we show that synthetic peptides with amino acid sequences corresponding to the segment [I] are not capable to penetrate the target cells and hence they do not inhibit the viral infection in cell lines and in vivo. Inhibition of the viral infection is achieved combining the [I] segment with a cell penetrating [P] segment.

A number of peptides derived from certain proteins have the capability to penetrate into the cells and get access into the cytoplasm and nucleus. These peptides are known as cell penetrating peptides or protein transduction domains (PTD) (Joliot, A., and Prochiantz, A. (2004) *Transduction peptides: from technology to physiology. Nat. Cell Biol.* 6, 189-96. Snyder, E. L., and Dowdy, S. F. (2004) *Cell penetrating peptides in drug delivery. Pharm. Res.* 21, 389-93. Deshayes, S., Morris, M. C., Divita, G., and Heitz, F. (2005) *Cell penetrating peptides: tools for intracellular delivery of therapeutics. Cell. Mol. Life. Sci.* 62, 1839-49). The most studied PTDs are the cationic peptides derived from proteins such as the HIV transcription factor TAT, the homeobox antennapedia (penetratin) from *Drosophila melanogaster* and the protein VP22 from the Herpes simplex virus. These peptides have raised great interest as potential carriers for the introduction of cargo molecules into the cells in order to enhance their biological activity, being these cargoes very diverse in nature like small drug-like molecules or genes and proteins. The potential of the PTDs as vectors for molecules with therapeutic interest have been shown in cell systems and also in animal models (Beerens, A. M., Al Hadithy, A. F., Rots, M. G., and Haisma, H. J. (2003) *Protein transduction domains and their utility in gene therapy. Curr. Gene Ther.* 3, 486-94. Wadia, J. S., and Dowdy, S. F. (2003) *Modulation of cellular function by TAT mediated transduction of full length proteins. Curr. Protein Pept. Sci.* 4, 97-104.) Wadia, J. S., and Dowdy, S. F. (2005) *Transmembrane delivery of protein and peptide drugs by TAT-mediated transduction in the treatment of cancer. AdV. Drug Deli Very ReV.* 57, 579-96. Rudolph, C., Schillinger, U., Ortiz, A., Tabatt, K., Plank, C., Muller, R. H., and Rosenecker, J. (2004) *Application of novel solid lipid nanoparticle (SLN)-gene vector formulations based on a dimeric HIV-1 TAT-peptide in vitro and in vivo. Pharm. Res.* 21, 1662-9).

A significant amount of research have been carried out in order to elucidate the mechanisms by which these peptides can get access into the cytoplasm and the nucleus passing through biological barriers formed by the cellular membrane systems such as the plasma membrane, the membranes of the endocytic compartments and the nucleus. Recently, it has been shown that a number of previously documented observations in culture cells regarding the cellular localization and cell entry of the PTDs at low and physiological temperature were due to artifacts caused by the fixation procedues and unspecific binding of peptides to the plasma membrane (Richard, J. P., Melikov, K., Vives, E., Ramos, C., Verbeure, B., Gait, M. J., Chemomordik, L. V., and Lebleu, B. (2003) *Cell penetrating peptides. A reevaluation of the mechanism of cellular uptake. J. Biol. Chem.* 278, 585-90. Vives, E., Richard, J. P., Rispal, C., and Lebleu, B. (2003) *TAT peptide internalization: seeking the mechanism of entry. Curr. Protein Pept. Sci.* 4, 125-32).

The most recent results suggest that endocytosis plays an essential role in the entry of PTDs into the cells. However, a detailed and generally accepted description of the intracellular traffic of these peptides has not emerged yet.

It was first reported that TAT peptide fusion proteins entry into the cells passing to neutral caveosomes via plasma membrane caveolae, but more recent studies have shown that caveolae are not required and TAT peptide cell entry occurs by macropinocytosis (Ferrari, A., Pellegrini, V., Arcangeli, C., Fittipaldi, A., Giacca, M., and Beltram, F. (2003) *Caveolae-mediated internalization of extracellular HIV-*1 *tat fusion proteins visualized in real time. Mol. Ther.* 8, 284-94. Wadia, J. S., Stan, R. V., and Dowdy, S. F. (2004) *Transducible TAT-HA fusogenic peptide enhances escape of TAT-fusion proteins after lipid raft macropinocytosis. Nat. Med.* 10, 310-5). Consistently with the postulated cell entry mediated by endocytosis, the PTDs have been observed in early and recycling endosomes. However, the biological activity shown by the molecules associated to the PTDs indicates that these peptides should escape at least partially from the endocytic compartments by a still unknown mechanism getting access into the cytosol. Colocalization of internalized TAT peptide with the Golgi marker BODIPY-ceramide has been reported, consistently with its lacks of visualization in later endosomes and lysosomes labeled with Lysotracker (Fischer, R., Kohler, K., Fotin-Mleczek, M., and Brock, R. 2004. *A stepwise dissection of the intracellular fate of cationic cellpenetrating peptides. J. Biol. Chem.* 279, 12625-35).

These data suggest that these peptides are capable to traffic to the Golgi directly from the early endosomes, which is consistent with a potential peptide entry into the cytosol from the ER preceded by retrograde transport of the peptides from the Golgi. However, other studies have reported colocalization of peptides in acidic late endocytic structures and in lysosomes. Such results have been reported for TAT peptide, octaarginine, TAT protein and conjugates of liposomes with TAT peptide (Al-Taei, S., Penning, N. A., Simpson, J. C., Futaki, S., Takeuchi, T., Nakase, I., and Jones, A. T. 2006. *Intracellular Traffic and Fate of Protein Transduction Domains HIV-*1 *TAT Peptide and Octaarginine. Implications for Their Utilization as Drug Delivery Vectors. Bioconjugate Chem.* 17, 90-100. Fretz, M. M., Koning, G. A., Mastrobattista, E., Jiskoot, W., and Storm, G. (2004) *OVCAR-*3 *cells internalize TAT-peptide modified liposomes by endocytosis. Biochim. Biophys. Acta* 1665, 48-56. Vendeville, A., Rayne, F., Bonhoure, A., Bettache, N., Montcourrier, P., and Beaumelle, B. (2004) *HIV-*1 *Tat enters T cells using coated pits before translocating from acidified endosomes and eliciting biological responses. Mol. Biol. Cell* 15, 2347-60).

However, it is possible that the PTDs could exploit various different mechanisms of cell entry and intracellular traffic, depending of several factors like cell type, nature of the PTD, temperature, cargo, etc.

DETAILED DESCRIPTION OF THE INVENTION

The present invention describes two topological variants of chimerical peptides which inhibit the viral infection by Flaviviridae:

$$[P]-[L_1]-[I]-[L_2]-[T] \text{ o } [I]-[L_3]-[P]-[L_4]-[T],$$

As [P] penetrating peptide are preferably selected, but not restricted to those, cationic peptides with the capability to carrier cargo molecules into the cells. As possible cationic peptides could be chosen penetratin, polyarginines of 7-10 residues such as R9 nonapeptide or R10 decapeptide or TAT peptide, although any other peptide sequence between 10-30 residues showing similar penetrating capability could be selected. These penetrating cationic peptides have the capability to penetrate into the cytoplasm of the cell via endocytosis, which could involve the traffic through the ER. This property is favorable for the biological activity of these peptides because it guarantees the peptide localization in the contiguity of the RER, the place where the precursor polyprotein synthesis and processing is carried out and constitutes the target of peptide antiviral activity.

Alternatively, other cell penetrating peptides could be also used as [P] segments like the cationic dendrimeric peptides or peptides comprising D-amino acids, which are very resistant to proteolytic degradation. The cationic peptides also guarantee a good biodistribution in vivo of the peptides from the present invention, allowing its favorable effective concentration in organs and tissues infected by Flaviviridae, to higher levels compared to larger molecules as the monoclonal antibodies. One example could be the use of peptides permeable to the blood-brain barrier (BBB) to treat Flaviviridae infections causing encephalitis like TBE, WNV, JEV, SLEV and KV. The molecular transport through the BBB is a formidable problem even for small drugs aimed for treatment of intraencephalic diseases (Temsamani, J. and Vidal, P. 2004. *The use of Cell-penetrating peptides for drug delivery. Drug Discov. Today* 9, 1012-1019).

The NS3pro protease inhibitory sequence [I], has the capability to inhibit or modify the interaction between the proteins NS3 and NS2B from Flavivirus (or between NS3 and NS4A from Hepacivirus and Pestivirus), and this way it affects the correct folding of NS3pro which is necessary for the protease activation process. In one embodiment of this invention, [I] consists in the sequence Asp50-Glu62 of the protein NS2B from DV2, or its homologous sequences from other Flavivirus. This sequence contains the residues corresponding to the beta strand 1 of the protein NS2B, which makes contacts with residues located at the N-terminal beta barrel of the active NS3pro protein. Thus, peptides according to the topologies described in this invention, compete with the native sequence of the cofactor NS2B protein during the folding of the NS3pro protein to the adoption of its active conformation. It leads to the formation of inactive NS3pro-peptide complexes because the full activation requires structural rearrangements not only in the N-terminal domain, but also in the C-terminal beta barrel two. Protease activation would need an additional binding of the region Glu66-Ile86 of the protein NS2B to the C-terminal domain of NS3pro. In addition, the binding of the segment [I] serves as an anchor of the peptides of the present invention to the protein NS3, in such a way that the N- or C-terminal extensions of these peptides could alter the surface topography of NS3 and interfere with its interactions with viral and/or host proteins. Such interactions include the substrate recognition and/or other interactions related to the conformation and/or functioning of the viral replication complex. Thus, in one embodiment of the present invention the [P] segment corresponding to the first topological variant are poly-D arginine, which besides having the cell penetrating property are also inhibitors of the Flavivirus NS3pro protease (SHIRYAEV, S. A., RATNIKOV, B. I., CHEKANOV, A. V., SIKORA, S., ROZANOV, D. V., GODZIK, A., WANG, J., SMITH, J. W., HUANG, Z., LINDBERG, I., SAMUEL, M. A., DIAMOND, M. S. and Alex Y. STRONGIN, A. Y., 2006.

*Cleavage targets and the D-arginine-based inhibitors of the West Nile virus NS*3 processing proteinase. Biochem. J. 393, 503-511). Thus, the binding of the [I] segment/anchor to NS3pro facilitates the fit of the polyArg peptides in the substrate binding site of the protease, well corresponding to the same chain anchored by the peptide (cis-inhibition) or a different chain (trans-inhibition). In an analog way, Hepacivirus and Pestivirus inhibitory peptides incorporate as [I] sequence the segment corresponding to the region Thr20-Leu31 of the NS4A protein (numbering of HCV), which is structurally equivalent to the beta strand 1 of the NS2B protein from Flavivirus.

In a second embodiment, which applies to Flavivirus, the [I] segment does not relate to any specific segment of the NS2B sequence, but consists in a peptide sequence with the capability to bind to NS3pro protein and stabilize the N-terminal barrel in its inactive conformation. In this case the peptide sequence makes contacts with the segment corresponding to Tyr23-Tyr33 of the NS3pro protein from DV2, or a homologous region corresponding to other Flavivirus. In addition, the [I] segment also makes stabilizing structural contacts with the residues from the segments Ala1-Gly14 and Ala56-Met59 of the protein NS3pro. Therefore, these peptides promote their inhibitory effect by interfering with the native folding of the protein NS3, inducing a folding pathway leading to the inactive conformation of the protease.

Such [I] sequences could be obtained by theoretical methods and/or experimental methods which make use of combinatorial libraries. In case of design by theoretical methods, the invention implies the use of one or various methods of computational molecular modeling and the use of three dimensional structural models of the protein NS3pro in its inactive conformation. Making use of the method(s) of computational modeling and the spatial coordinates of the 3D structural model of the inactive NS3pro protein, it is possible to model a polypeptide main chain in an extended conformation, which forms an antiparallel beta strand with the segment corresponding to the beta strand A1 of the N-terminal beta barrel. In addition, it is also possible to model the side chains of the polypeptide chain, in such a way that the chemical identity of this side chains and its conformers imply energetically favorable atomic contacts. This invention involves the combined exploring by computational means of the peptide sequence and conformational space, the side chain rotamer space of the peptide and also of the protease and the selection of the most favorable peptide variants according to an energy scoring of the obtained models, which indicate a potential higher affinity of the peptide-protein interaction.

The coordinates corresponding to the inactive NS3pro structural models could originate from experimental data obtained by the methods of x-ray diffraction and/or NMR or by the use of models obtained by computational modeling methods. In the case of DV2, the coordinates could be obtained from the file 1BEF of the Protein Data Bank (PDB). For other Flavivirus, it is possible to obtain 3D models by the method of homology modeling. In the present invention we describe the [I] sequence: QWPALPKIEAQDG (SEQ ID NO: 369), which was designed according to this second embodiment of the present invention. The FIG. 1D shows a computational model of the tridimensional structure of the NS3pro-[I] complex corresponding to this embodiment. According to this model, the [I] segment adopt an extended beta strand structure associated to the segment Gly29-Y33 of NS3pro (DV2 numbering).

Additionally, combinatorial libraries of synthetic peptides or phage displayed peptides libraries could be used in order to obtain [I] sequences with similar properties to peptides described in the second embodiment of the present invention. In this case the recombinant NS3pro protein is used as target for ligand selection or biopanning.

In other embodiment of the present invention, the [I] segment consist in the sequence Ser70-Gly82 of the protein NS2B from DV2, or its homologous sequences from other Flavivirus. This sequence contains the beta strands 3 and 4 of the protein NS2B, which contact and form part of the active NS3pro protease. Thus, peptides according to the topologies described in this invention, compete with the corresponding segment of the cofactor NS2B protein during the folding of the NS3 protein to its active conformation and hamper the proteolytic processing at the junction NS2B-NS3. It leads to the formation of inactive NS3pro-peptide complexes, because these peptides interfere with the correct configuration of the substrate binding site, in particular at P2 site, which is essential for the enzyme catalytic activity.

In addition, the binding of the [I] segment corresponding to peptides of this invention serves as an anchor to the protein NS3, such that the N-terminal or C-terminal extension of the peptides could modify the surface topography of NS3 and interfere with the interaction of this protein with other viral or host proteins.

In an embodiment related to the previous one (peptide 10 in table 1), the [I] segment consists in the sequence Ser70-Ile86 of the NS2B protein from DV2, or its homologous sequences from other Flavivirus. This region includes, besides the beta strands 3 and 4, also the beta strand 5 of NS2B. In this case, the peptides corresponding to the first topological variant include a C-terminal extension comprising a [L2] segment of 3 or 4 residues and a [T] segment consisting of the tripeptide XRR, with a C-terminal carboxylic group. The sequences of these peptides are consistent with their binding to the NS3 protein adopting its active conformation, the beta strand 5 and the loop between the strands 4 and 5 guarantee the correct formation of the P2 site.

Moreover, the binding of the segment [I] facilitates the structural changes in the C-terminal beta barrel which are necessary for the activation, such as the change in orientation of the E2b-F2 beta hairpin, which allows the arrangement of important residues involved in the substrate recognition like Gly151, Gly153 and Tyr161. However, the formed complex is inactive, because the [L2] segment serves as stabilizing-linker allowing the additional binding of the [T] segment to the substrate binding site, with the dipeptide RR occupying the positions S1 and S2. Thus, the protease active site becomes blocked by the peptide. The segments [L1], [L2], [L3] and [L4] of the present invention are linker sequences of 0-6 residues, which connect the segment [P], [I] and [T], depending on the topological variant. These linker segments contains mainly small and/or polar amino acids (Gly, Ser, beta-Ala), which provide flexibility. These linker segments could also consist of sequences capable to interact favorably with residues from the NS3pro protein, providing the peptides of the present invention with an additional stabilizing effect.

The [T] segments of the present invention are sequences between 0 and 10 amino acids, localized at the C-terminal ends of the peptides. In an embodiment, the [T] segment is an ER retention signal, like the KDEL sequence. The addition of this signal facilitates the traffic of peptides by retrograde transport to the ER. The increase in peptide concentration within the ER contributes to enhance the transport of the peptides to the cytosol. It results in an increase of the effective peptide concentration in the contiguity of the ER, where occurs the synthesis of the viral polyprotein and in particular the synthesis of the NS3pro. The incorporation of the KDEL signal to the peptide sequence is compatible with the presence of cationic cell penetrating peptides as [P] segments, because the retrograde transport through the ER is a putative pathway of cationic peptide penetration into the cytosol. This way of penetration involved the traffic of peptides from early endosomes to the ER via the trans-Golgi network (TGN). The sequence KDEL interacts with the KDEL receptor present at the TGN which transport the peptide to the ER where it is discharged. The peptide transport from the ER lumen into the cytosol is an efficient process, which occurs through channels present at the ER membrane formed by the Sec61 protein from the translocon complex. This mode of penetration into the cytosol is exploited by bacterial toxins like the cholera toxin, Ricin and the exotoxin A from *Pseudomonas*, etc.

Use of a FG Hairpin Based Segment as Cell Penetrating Peptide. Inhibitory Effect of This Segment on DV Entry into the Cell.

A novelty of the present invention is the modular structures displayed by these peptides, combining segments or modules with different functions: segment with antiviral activity, cell penetrating peptide, signals for traffic and intracellular localization, lipidation, etc. Thus, it is possible to exploit the capability of peptides of 20-30 residues to incorporate in its sequence a great variety of information, which allows to maximize the functional activity of the peptides in cells and in vivo. In this invention we have also incorporated bi- or polyfunctional modules in peptide design.

The antiviral activity displayed by peptides of the present invention is based primarily on the inhibition of NS3 protease activation process. The [I] segments or modules described in the present invention as inhibitors of the viral protease activation process, have the capability to bind to the NS3pro protein and to block the interaction between this protein with the viral protein NS2B from Flavivirus (NS4A in Hepacivirus), which is necessary for activation of the protease. However, the presence of this segment does not guarantee that peptides are capable to block the viral infection in vitro and in vivo. Thus, we show in the example 3 that the segment Ser70-Gly82 corresponding the protein NS2B from DV2 is capable of inhibiting the viral infection in vitro only if it is present in the same polypeptide chain together with a cell penetrating peptide. In order to inhibit the viral infection, the peptides of the present invention need to penetrate cells, get access into the cytosol and bind the NS3pro protein, whose folding take place at the cytosolic face of the ER membrane.

In an embodiment of the present invention, we use as cell penetrating segment the sequence corresponding to the FG beta hairpin of domain III from the envelope protein of DV1-4. In this invention we show that [P] segments based in these sequences are capable carry into the cell different peptide cargoes. Previously, it has been shown that cyclic peptides based on the sequence of the FG hairpin from DV1-2, interact with the cell receptor LRP1 (aplicación de patente: Métodos y moléculas para la prevención y el tratamiento de la infección con Flavivirus. CU 2006-0091. Huerta V, Chinea G, Fleitas N, Martín A M, Sarria M, Guirola O, Toledo PG, Sánchez A, Besada V A, Reyes O, Garay H E, Cabrales A, Musacchio A, Padrón G R, González L J).

It is known that the LRP1 receptor interacts and internalize into the cells about 30 natural ligands, among them the pertussis exotoxin A (Herz J, Strickland D K. (2001) LRP: a multifunctional scavenger and signaling receptor. J Clin Invest. 108:779-84. Kounnas M Z, Morris R E, Thompson M R, FitzGerald D J, Strickland D K, Saelinger C B, 1992. *The alpha 2-macroglobulin receptor/low density lipoprotein receptor-related protein binds and internalizes Pseudomonas exotoxin A. J Biol Chem* 267:12420-12423). This receptor is expressed in the majority of cell types, tissues and organs. The DV has also the capacity to infect many cell lines and organs, therefore the use of peptides containing a cell penetrating peptide based on the sequence of the FG hairpin, is very favorable in order to achieve an affective internalization into the infection susceptible cells. LRP1 expression is high in the liver and the brain, which are main target organs of diseases caused by Flaviviridae. For example, the viruses from the TBE and JEV complexes cause encephalitis and the YFV is mainly viscerotropic and causes hepatitis. For the same reason, this segment would be also effective against HCV, as present in the anti-HCV peptides described in the present invention.

In the particular case of chimerical peptides described in the present invention as inhibitors of dengue infection, those modules based on the FG hairpin possess a bifunctional character. Besides the already described role as cell penetrating segment, this segment displays also anti-DV antiviral activity per se. Previously it has been shown that peptides based on the FG hairpin inhibit infection productive cell entry of DV by a mechanism which involves an step occurring after virus adhesion to the plasma membrane (aplicación de patente: Métodos y moléculas para la prevención y el tratamiento de la infección con Flavivirus. CU 2006-0091. Huerta V, Chinea G, Fleitas N, Martín A M, Sarria M, Guirola O, Toledo P G, Sánchez A, Besada V A, Reyes O, Garay H E, Cabrales A, Musacchio A, Padrón G R, González L J). These peptides are highly efficient inhibiting viral infection when they are present in solution at the moment of virus entry into the cell. Furthermore, as shown in the example 2, the peptides of the present invention, which do not possess a cell penetrating segment based on the FG hairpin and whose antiviral effect is based only in their NS3 protease inhibitory modules, are less efficient if they are administered to the media at the same time as the virus. These peptides (lacking FG hairpin segment) show their maximum antiviral activity if they are preincubated with the cells before the virus is added, which is consistent with a mechanism of inhibition requiring cell penetration and an effective intracellular localization in order to inhibit the NS3 protease activation.

Therefore, a novel element of the present invention consists in the combination of a cell entry inhibitor (which is also a cell penetrating peptide) and a segment inhibiting the viral protease activation.

Hence, these chimerical peptides possess a biological activity profile which is more favorable compared with those peptides based in only one of these segments, considering the relationship between the moments of peptide addition with respect to the beginning of the viral infection.

Cell Penetration and Intracellular Fate. N-Terminal Lipidation and Retention in the ER.

The present invention applies also for the lipidation of the previously described chimerical peptides. The herein mentioned lipidation typically consists on the myristoylation or the palmitoylation at the N-terminal ends of peptides. In this patent as myristoylation we mean the chemical modification of the peptides by covalent attachment of the myristic acid $CH_3(CH_2)_{12}CO_2H$ to the N-terminal group of the peptides by means of an amide bond, resulting in the chemical structure $CH_3(CH_2)_{12}CO_2$—NH—P, where P is the amino acid sequence of the myristoylated peptide. Similarly, the palmitoylation results in the addition of the $CH_3(CH_2)_{14}CO_2H$ palmitic group. As lipidation we also mean herein the covalent attachment of the lipid chain to the side chains of the amino acid residues SER and/or TYR, added as N-terminal extensions to the peptides. In order to exert their antiviral activity, which is based primarily on the inhibition of the NS3 protease activation, the peptides of the present invention need to cross various biological barriers, consisting of diverse membrane systems of the cell.

These peptides need to transit from the extracellular space to their final fate optimal for the antiviral effect, the cytosolic face of the ER. In general, lipidation increases peptide lipophilicity, which is a favorable property regarding the interaction with biological membranes. In this invention we have originally combined peptide lipidation with the addition of some traffic and cellular localization signals (sequences) which enhance the biological activity of peptides. Thus, this design is aimed to increase the efficiency of various steps involved in the manifestation of peptide antiviral activity on the cells: adsorption on the plasma membrane, cell penetration, intracellular traffic/retrograde transport, intracellular localization on the ER membrane and the interaction with NS3pro protein.

The choice of the chemical nature of the lipid(s) adequate for peptide lipidation is not trivial. One premise of the chimerical peptide design of the present invention, consists in selecting specific lipid(s) for its chemical conjugation to the peptides, in such a way that this chemical modification affect favorably the physicochemical and functional properties of the peptides concerning the different processes involved in their antiviral action: binding to the plasma membrane, cell penetration/endocytosis, intracellular traffic/retrograde transport, transport to cytosol and binding to NS3pro. During this process, the peptides should interact with membranes of different biophysical properties, and participate in the transport between different intracellular compartments. An optimal lipid regarding one individual step could be detrimental respect to other steps and therefore being not indicated for lipidation of antiviral peptides of the present invention. As an example, considering the interaction with the ER membrane, the monosaturated glycerolipids are potentially favorable. These lipids are common in this membrane (Keenan T. W. AND Morrea, D. J. *Phospholipid class and fatty acid composition of Golgi apparatus isolated from rat liver and comparison with other cell fractions. Biochemistry* 9: 19-25, 1970), which is characterized by its higher fluidity and smaller thickness compared to the plasma membrane rich in sphingolipids, sterols and disaturated phospholipids. Thus, an unsaturated lipid with relatively short chain which would be adequate for insertion in the ER membrane would not be favorable in the plasma membrane. This kind of lipids would localize preferably in the most fluid domains of the plasma membrane, segregated from domains rich in sphingolipids and cholesterol such as the lipid rafts, which are involved in endocytosis. Various previous analysis of the endocytic routing of lipid analogs differing in the nature of their hydrophobic tails have shown that short tailed unsaturated lipids after being endocytosed are efficiently recycled back to the plasma membrane via the endocytic recycling compartment (ERC) and saturated long tailed lipids are routed through the endocytic way to late endosomes and lysosomes (Mukherjee, S., Soe, T. T and Maxfield, F. R. 1999. *J. Cell Biol.*, 144, 1271-1284; Koval, M., and R. E. Pagano, 1989. *J. Cell Biol.* 108:2169-2181; Mayor, S., J. F. Presley, and F. R. Maxfield, 1993. *J. Cell Biol.* 121:1257-1269; Sandhoff, K., and A. Klein., 1994. *FEBS Lett.* 346:103-107).

Previous studies have reported examples of peptide myristoylation facilitating cell penetration and the biological activity of peptides at their corresponding intracellular targets (P. J. Bergman, K. R. Gravitt, C. A. O'Brian, *An N-myristoylated protein kinase C-alpha pseudosubstrate peptide that functions as a multidrug resistance reversal agent in human breast cancer cells is not a P-glycoprotein substrate, Cancer Chemother. Pharmacol.* 40 (1997) 453-456. B. R. Kelemen, K. Hsiao, S. A. Goueli, *Selective in vivo inhibition of mitogen-activated protein kinase activation using cell-permeable peptides, J. Biol. Chem.* 277 (2002) 8741-8748. T. Eichholtz, D. B. de Bont, J. de Widt, R. M. Liskamp, H. L. Ploegh, *A myristoylated pseudosubstrate peptide, a novel protein kinase C inhibitor, J. Biol. Chem.* 268 (1993) 1982-1986).

However, myristoylation per se does not guarantee peptide penetration into the cells. In fact, there are examples of myristoylated peptides which do not penetrate into the cells and it has been postulated that penetration depends also on the nature of the peptide, being favorable properties having a positive net charge and a homogeneous distribution of basic residues between acid and hydrophobic residues (Carrigan, C. N., Imperiali, B. 2005, *Anal. Biochem.* 341 290-298).

The first steps in the interaction of peptides of the present invention with cells are the adhesion to the plasma membrane and/or the binding to molecules present on the membrane. The addition of myristoyl or palmitoyl groups increases the lipophilicity of peptides of this invention, facilitating the peptide binding to the plasma membrane. Besides the presence of the lipid, the peptides of this invention contain sequences of cell penetrating peptides, which interact with molecules present in the membrane. An example is the case of cationic cell penetrating peptides which interact with glycosaminoglycans, in particular with heparin-like heparan sulfates.

It has been shown that binding to heparan sulfates is essential for cell penetration by cationic peptides. They can also interact with other negatively charged molecules of the plasma membrane like anionic lipids and proteins. Similarly, other peptides which interact with endocytic cell receptors can function as carrier or cell penetrating peptides facilitating the entry of cargo molecules into the cells. Lipidation of peptides of the present invention therefore increases the binding affinity to the plasma membrane providing an additional anchoring site.

In general, myristoylated proteins containing a cluster of basic residues juxtaposed to a myristoylation signal interact favorably with membranes rich in cholesterol and sphingolipids (McCabe, J. B., and Berthiaume, L. G. (1999). *Functional roles for fatty acylated amino-terminal domains in subcellular localization. Mol. Biol. Cell* 10, 3771-3786. McCabe, J. B., and Berthiaume, L. G. (2001). *N-Terminal Protein Acylation Confers Localization to Cholesterol, Sphingolipid-enriched Membranes But Not to Lipid Rafts/Caveolae. Mol. Biol. Cell* 12, 3601-3617), which are components of lipid rafts involved in endocytic processes and in the routing of proteins to different organelles and specific membranes of the cells (JOOST C. M. HOLTHUIS, THOMAS POMORSKI, RENEÂ' J. RAGGERS, HEIN SPRONG, AND GERRIT VAN MEER. 2001. *The Organizing Potential of Sphingolipids in Intracellular Membrane Transport. Physiol. Rev.* 81, 1689-1723. Simons, K. and Ikonen, E. 1997. *Functional rafts in cell membranes. Nature,* 387: 569-572). Therefore, the myristoylation is favorable for the capacity of peptides of the present invention to penetrate cells, in particular those peptides containing cationic cell penetrating peptides and/or polyarginines as signals for retention at the cytosolic face the ER membrane. In fact, it has been shown that lipidated peptides, containing certain positive charge can penetrate into the cells (Carrigan, C. N., Imperiali, B. 2005, *Anal. Biochem.* 341 290-298).

Detergent resistant specialized microdomains of the membrane (DRMs) rich in glycosphingolipids and cholesterol seem to be essential for internalization of various bacterial toxins into the cells (Cholera toxin, Ricin, Shiga toxin, etc) and molecules associated to these DRMs like the GM1 ganglioside and the sphingolipid Gb3 are receptors of some of these toxins which penetrate cells by endocytosis (Spangler, B. D. (1992) *Microbiol. Rev.* 56, 622-647. Fujinaga Y, Wolf A A, Rodighiero C, Wheeler T E, Tsai B, Allen L, Jobling M G, Rapoport T A, Holmes R K, Lencer W I. 2003. *Gangliosides that associate with lipid rafts mediate transport of cholera and related toxins from the plasma membrane to endoplasmic reticulum. Mol Biol Cell* 14: 4783-4793. Falguieres T, Mallard F, Baron C, Hanau D, Lingwood C, Goud B, Salamero J, Johannes L. 2001. *Targeting of Shiga toxin B-subunit to retrograde transport route in association with detergent-resistant membranes. Mol Biol Cell* 12: 2453-2468).

These toxins exert their activities in the cytosol after passing through a retrograde transport process which involves the traffic from the endosomes to the ER, well directly or through the TGN (Sandvig K, van Deurs B. 2002. *Membrane traffic exploited by protein toxins. Annu Rev Cell Dev Biol* 18: 1-24). Then these toxins pass from the ER to the cytosol also by retrograde transport and apparently making use of the ER associated degradation mechanism (ERAD) (Lord, J. M., and Roberts, L. M. (1998) *J. Cell Biol.* 140, 733-736. Lord, J. M., Deeks, E., Marsden, C. J., Moore, K., Pateman, C., Smith, D. C., Spooner, R. A., Watson, P., and Roberts, L. M. (2003) *Biochem. Soc. Trans.* 31, 1260-1262. AbuJarour, R. J., Dalal, S., Hanson, P. I. and Draper, R. K. 2005. *J. Biol. Chem.* 280, 15865-15871).

Thus, the potential colocalization of the lipidated peptides of the present invention in membrane domains rich in sphingolipids would be consistent with their potential capacity to exploit a cell penetration mechanism based in the above mentioned lipid dependent retrograde transport used by bacterial toxins.

In other embodiment of the present invention the designed peptides use as cell penetrating peptide the FG hairpin from domain III of the envelope protein of DV3 or the homologous peptides of serotypes 1, 2 and 4. Previously, it has been shown that these peptides bind to the cellular receptor LRP1 (aplicación de patente: Métodos y moléculas para la prevención y el tratamiento de la infección con Flavivirus. CU 2006-0091. Huerta V, Chinea G, Fleitas N, Martín A M, Sarria M, Guirola O, Toledo P G, Sanchez A, Besada V A, Reyes O, Garay H E, Cabrales A, Musacchio A, Padrón G R, González L J). This receptor mediates the endocytosis of about 30 ligands and it is used for cell entry by the pertussis exotoxin PTx (Herz J, Strickland D K. (2001) *LRP: a multifunctional scavenger and signaling receptor. J Clin Invest.* 108:779-84. Kounnas M Z, Morris R E, Thompson M R, FitzGerald D J, Strickland D K, Saelinger C B. *The alpha 2-macroglobulin receptor/low density lipoprotein receptor-related protein binds and internalizes Pseudomonas exotoxin A. J Biol Chem* 1992; 267:12420-12423).

In this invention we have shown that peptides corresponding to the FG hairpin are capable to mediate the cell entry of peptide cargoes. The lipidation (myristoylation or palmitoylation) of these FG hairpin containing peptides would increase the effective affinity for their cellular receptor by enhancing the partition of the peptides in the lipid membrane. This peptide lipidation is also consistent with an increase in the cell penetrating potential of peptides via endocytosis mediated by LRP1 receptor.

One possibility is that these peptides penetrate into the cells in a similar way to PTx. This toxin get access into the cytosol by retrograde transport from the endosomes passing successively through the TGN, the ER and then to the cytosol. PTx has the capacity to exploit at least two retrograde transport pathways mediated by LRP1 interaction: a) lipid dependent pathway and b) lipid independent pathway (Smith, D. C., Spooner, R. A., Watson, P. D., Murray, J. L., Hodge, T. W., Amessou, M., Johannes, L., Lord, J. M. and Roberts, L. M., 2006. *Internalized Pseudomonas Exotoxin A can Exploit Multiple Pathways to Reach the Endoplasmic Reticulum. Traffic,* 7: 379-393). The lipid dependent pathway seems to be related to the localization of a 20% of LRP1 molecules in lipid rafts of the plasma membrane. Those peptides of the present invention, which are lipidated and have the capability to interact with LPR1 can potentially exploit more efficiently the lipid dependent pathway, in particular those peptides including a basic cluster of polyarginines (added as an ER retention signal) have a favorable composition to localize in raft adjacent membrane domains rich in cholesterol and sphingolipids.

Other embodiment of the present invention consists in peptides having the KDEL signal at the C-terminal end. These peptides are synthesized with a carboxylic C-terminal end in order to make functional the KDEL signal for retention at the lumen of the ER (Teasdale, R. D. & Jackson, M. R., 1996. *Annu. Rev. Cell Dev. Biol.* 12, 27-54). The addition of this signal to the peptide sequences contributes favorably to their retrograde transport from the Golgi to ER and the later retention of these peptides in the lumen of the ER. Thus, this signal contributes to the penetration into the cytosol of those peptides which make use at least partially of the retrograde transport pathway. A higher efficiency of the transport leads to a higher cytosolic concentration of the peptides and hence a more potent blocking activity of NS3 protease activation. In the example 3 we have shown that the addition of the KDEL signal to peptides of the present invention can lead to an increase of the antiviral activity of the peptides.

The addition of the KDEL signal is valid for peptides of the present invention having or not lipids attached in their N-terminal ends. It is consistent with the fact that this signal is found both in soluble and in type II membrane proteins of the ER. Lipidated peptides of the present invention present in the lumen of the ER would adopt a topology similar to the type II membrane proteins.

In the case of peptides of the present invention having an FG hairpin related cell penetrating segment, the addition of the KDEL signal provides these peptides with the additional capacity of interfering with the anterograde transport of the receptor LRP1 and hence leading to a decrease of their receptor expression levels on the plasma membrane. Therefore, the combination of these sequence/signals has an indirect negative effect on the entry of the virus into the cells reducing the expression of the receptor at the plasma membrane, and this effect is additional to the above described direct effect of peptides based on the FG hairpin blocking the cell entry of the virus. Previous evidences indicate that peptides based on the FG hairpin favor the interaction of LRP1 with its chaperone receptor associated protein RAP (aplicación de patente: Métodos y moléculas para la prevención y el tratamiento de la infección con Flavivirus. CU 2006-0091. Huerta V, Chinea G, Fleitas N, Martín A M, Sarria M, Guirola O, Toledo P G, Sánchez A, Besada V A, Reyes O, Garay H E, Cabrales A, Musacchio A, Padrón G R, González L J). It means that these peptides are able to interact with intracellular LRP1, present in the exocytic pathway during its transit to the plasma membrane. As these peptides contain also the KDEL signal, the intracellular complexes peptide-LRP1 and/or peptide-LRP1/RAP could bind to the KDEL receptor and thus they could be routed from the Golgi to the ER, affecting the transport of LRP1 to the plasma membrane and indirectly affecting the LRP1 mediated cell entry of the virus.

A common property of peptides of the present invention is that they display antiviral activity based on inhibition of NS3 protease activation. The inhibition of protease activation is achieved by blocking specifically the interaction of the protein NS2B (NS4A in Hepacivirus) with the NS3pro domain, being this interaction a necessary condition for the correct folding and full activity of the protease.

The protein folding and activation of the protease NS3, as well as the folding and processing of the core protein and the rest of non-structural proteins, takes place at the cytosolic face of the ER membrane. Therefore, a way to enhance the antiviral activity of the peptides of the present invention consists in increasing their intracellular localization at the ER membrane. With this aim, the peptides could be chemically lipidated (myristoylated or palmitoylated) at the N-terminal end. The lipidated peptides have the capacity to interact favorably with lipid membranes. The better association of the lipidated peptides with the ER membrane (favored by the lipid moiety) increases the effective apparent affinity of the interaction between the peptides and the NS3pro protein, an effect related to the following factors: 1) increase of the local peptide concentration, 2) the bimolecular interaction occurs in two dimensions (the plane of the membrane) and 3) the fast lateral diffusion of lipidated peptides at the membrane. Furthermore, those peptides lipidated at their N-terminal end when associated to the cytosolic face of the ER membrane simulate topologically the type I membrane proteins, thus they acquires not only the correct localization but also an orientation respect to the membrane which is similar to the viral NS2B protein (NS4A in Hepacivirus).

In general, when there are not additional signals like palmitoylation and/or basic clusters, the myristoylation of cytosolic proteins induce a localization of these proteins mainly at the ER membrane (McCabe, J. B., and Berthiaume, L. G. (1999). *Functional roles for fatty acylated amino-terminal domains in subcellular localization. Mol. Biol. Cell* 10, 3771-3786). The association of the myristate per se with the membrane is not strong enough and does not guarantee the total retention of peptides in the ER membrane. However, the ER membrane constitutes the 60% of the intracellular membranes which guarantee a significant effective concentration of the peptides with respect to the rest of membranes. When in addition to myristoylation basic clusters are also present, the cytosolic proteins localize mainly at the inner face of the plasma membrane and in endosomes.

Various peptides of the present invention contain cationic segments as cell penetrating peptides which guarantee also a favored interaction with negatively charged molecules located at the outer face of the plasma membrane. Some peptide of the present invention contains clusters of arginines as cationic segment which also constitute ER retention/redirection signals (Teasdale, R. D. & Jackson, M. R. (1996) *Annu. Rev. Cell Dev. Biol.* 12, 27-54. Zerangue, N., Schwappach, B., Jan, Y. N. & Jan, L. Y. (1999) *Neuron* 22, 537-548. Schutze, M. P., Peterson, P. A. & Jackson, M. R. (1994) *EMBO J.* 13, 1696-1705). These peptides have been designed with the aim to display simultaneously both properties: an efficient cell penetration and an intracellular localization mainly at the cytosolic face of the ER membrane. The arginines based traffic signals to the ER are highly efficient and play an important role in the mechanism of quality control of membrane proteins (Chang, X. B., Cui, L., Hou, Y. X., Jensen, T. J., Aleksandrov, A. A., Mengos, A. & Riordan, J. R. (1999) *Mol. Cell.* 4, 137-142. Margeta-Mitrovic, M., Jan, Y. N. & Jan, L. Y. (2000) *Neuron* 27, 97-106).

Unlike the dilysine signal which is restricted to the C-terminal end of type I membrane protein, the arginines based signals are found in many positions of the sequence of membrane proteins, including the N- and C-terminal ends and also the internal loops located at the cytosolic face. The versatility of the retention signals based in arginines have been exploited in the present invention in order to design peptides which combine them with the C-terminal KDEL signal. Thus, some lipidated peptides of the present invention containing these signals, enter into the cells and transit to the cytosol by retrograde transport, being favored by the KDEL signal during their transit to the ER and later retained at the cytosolic face of the ER membrane supported by the arginines based signal.

In one embodiment of the present invention we have included the design of lipidated peptides whose sequence contain two successive putative retention signal for retention at the cytosolic face of the ER membrane. The resulting sequence is LRRRRLRRRRL, which corresponds to two consecutive LRRRRL sequence overlapped in a central Leu residue. The sequence of four consecutive arginine preceded by a hydrophobic residue is typical of RE retention sequences (Zerangue, N., Malan, M. J., Fried, S. R., Dazin, P. F., Jan, Y. N., Jan, L. Y. and Schwappach, B. 2001. *PNAS,* 98: 2431-2436). In these regards, one of the novel aspects of the present invention is that the resulting sequence have the duality of being an efficient RE retention signal and also a cell penetrating peptide. The cell penetrating property of the resulting sequence is provided by the eight arginine residues which is similar to the polyarginine sequences, very efficient cationic PTDs.

Figure 1:
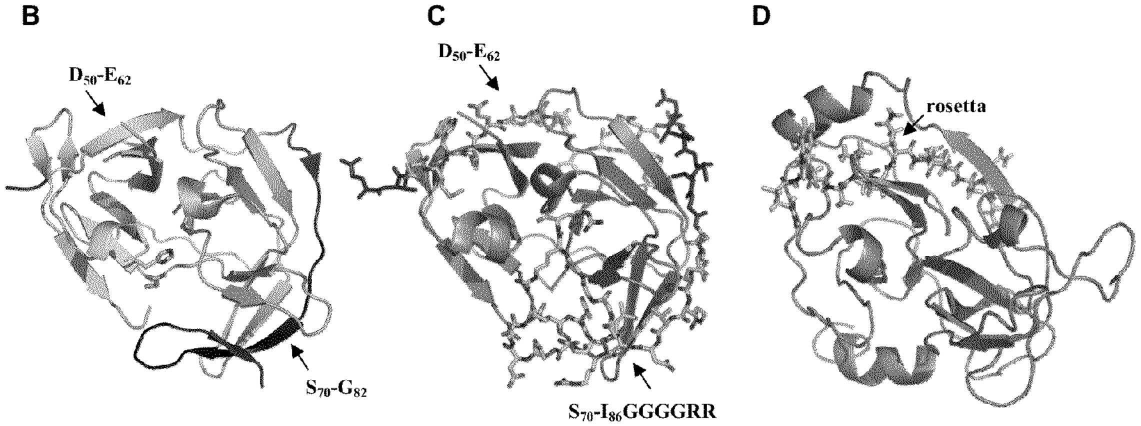
FIG. 1: Design of peptide inhibitors of NS3pro protease activation. A: Multiple sequence alignment of NS2B protein sequences SEQ ID NOS: 370-382 from Flavivirus. The herein described activation inhibitor segments are highlighted with double arrows, the light (dark) gray arrow corresponds to the segment bound to the N-terminal (C-terminal) beta barrel domain of NS3pro. B: Three dimensional structural model of the NS2B-NS3pro complex of Flavivirus. The segment $D_{50}$-$E_{62}$ of NS2B from DV2 bound the N-terminal beta barrel domains of NS3pro and segment $S_{70}$-$G_{82}$ of NS2B from DV2 bound to the C-terminal domain are highlighted. C: NS3pro protease activation inhibitory segments $D_{50}$-$E_{62}$ and $S_{70}$-$I_{86}$-GGGGRR. The C-terminal extension of the latter peptide binds to the protease active site, blocking the interaction of the protease with its substrates. D: Model of the complex formed by NS3pro in its inactive conformation (structure of the protein without NS2B) and a computationally designed peptide of the present invention.

TAT: peptide 1 of table 1; NS2Bden2+pP2: peptide 2 of table 1, cell penetrating segment is penetratin; NS2Bden2+pRR: peptide 3 of table 1, decaarginine as cell penetrating peptide; NS2Bden2+TAT+KDEL: peptide 4 of table 1; pNR+TAT: peptide 18 of table 1, negative control; NS2Bden2: segment [I] of peptide NS2Bden2+TAT.

Figure 6:
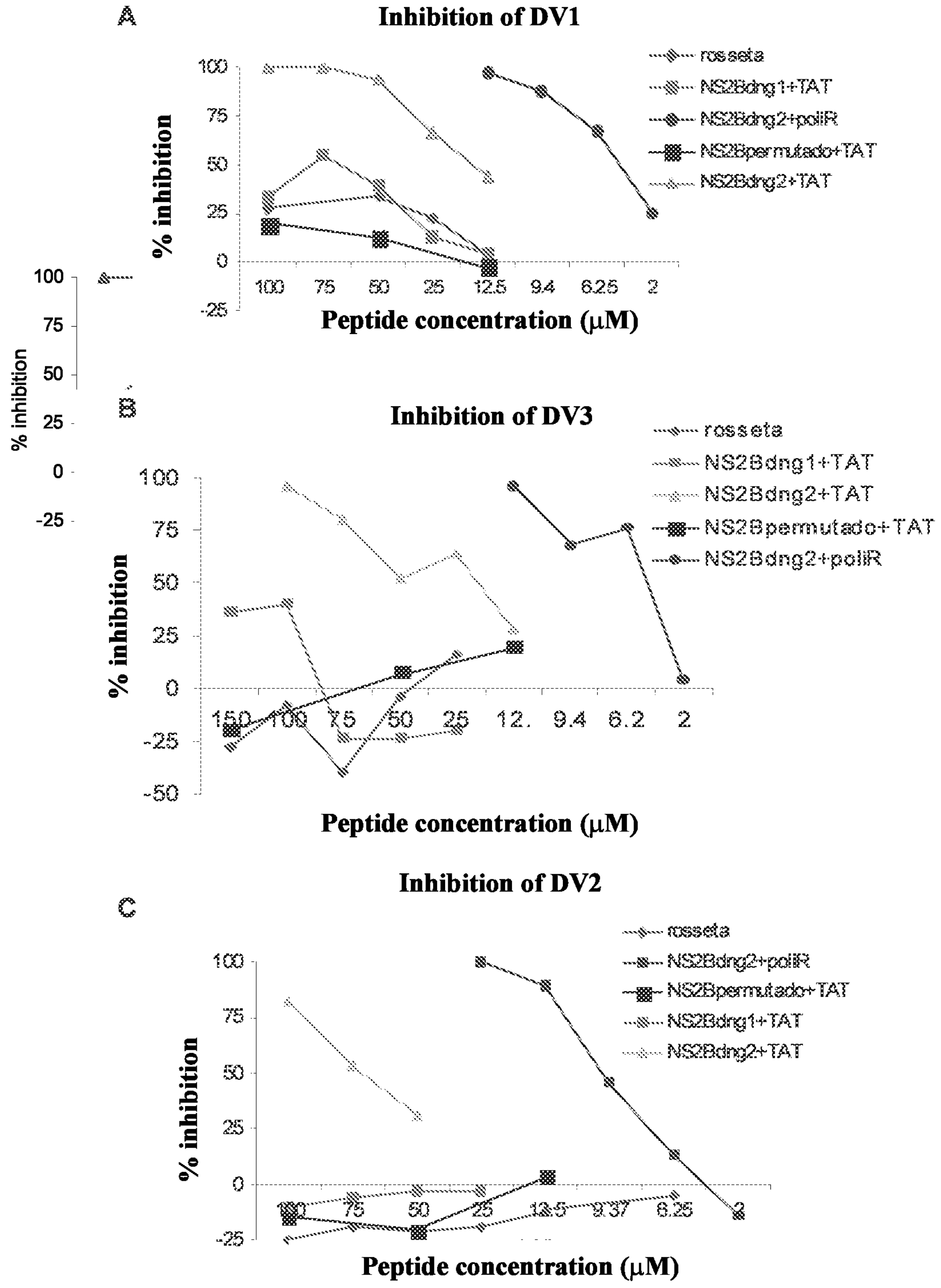

FIG. 6: Antiviral activity of peptides against homologous and heterologous serotypes of DV. The antiviral activity of peptides was tested by reduction of the number of viral plaques in presence of VD1 (A), VD3 (B) and VD2 (C). Rosseta: peptide computationally designed to bind to the N-terminal domain of NS3pro of DV2 (peptide 5 of table 1); NS2Bden2+poliR: peptide 3 of table 1, decaarginine as cell penetrating peptide; NS2Bden2+TAT: peptide 1 of table 1; NS2Bden1+TAT: peptide 6 of table 1; NS2 Bpermutado+TAT: peptide 18 of table 1, negative control of the experiment. The primary structure of NS2 Bpermutado+TAT is analogous to peptide NS2Bden2+TAT, the [I] segment have an amino acid composition identical to NS2Bden2+TAT but the sequence was permutated.

EXAMPLES

Example 1

Design and Synthesis of Chimerical Peptides Inhibitor of the Infection by Flaviviridae The chimerical peptides inhibitor of the infection by Flaviviridae described in this invention have a primary structure according to the following topologies:

$$[P]-[L_1]-[I]-[L_2]-[T] \text{ o } [I]-[L_3]-[P]-[L_4]-[T],$$

where, [P] is the amino acid sequence of a cell penetrating peptide, typically of 10-30 residues, which have the capacity to facilitate the internalization of the whole peptide molecule into the cell cytoplasm and to get access to the contiguity of the RER; [L1, L2, L3, L4], are linker sequences of 0-6 residues; [I], is an amino acid sequence which blocks the activation of NS3pro protease, residues of this segment make contacts with at least one amino acid from the beta strands B2a and B2b of the C-terminal beta barrel domain, or the beta strand A1 of the N-terminal beta barrel domain of NS3pro protein from Flavivirus (or the structurally corresponding region in Hepacivirus or Pestivirus), being the NS3pro protein in its active or inactive conformation (FIG. 1); [T], sequence of 0 to 10 residues, typically is one or two signals of retention in the ER like the sequences KDEL and LRRRRL, or the sequence XRR which displays a capability to binding to the protease active site.

Tables 1 and 2 show sequences of chimerical peptides according to the topologies 1 and 2 respectively. The basic peptide design is based in the presence of a protease activation inhibitor segment [I] and a cell penetrating segment [P]. As [I] segments are included the sequences $D_{50}$-$E_{62}$, $S_{70}$-$G_{82}$ and $S_{70}$-$I_{86}$ of the NS2B protein from DV1-4. The corresponding sequences from WNV and HCV are also included. The segment $D_{50}$-$E_{62}$ binds to the N-terminal domain of NS3pro and the segments $S_{70}$-$G_{82}$ y $S_{70}$-$I_{86}$ bind to the C-terminal domain (FIG. 1A-C).

TABLE 1

Design of chimerical peptides according to the topology [P]-[L1]-[I]-[L2]-[T]

| SEQ ID NO. | No | [P] | [L1] | [I] | [L2] | [T] | Virus | Penetrating peptide | Target domain |
|---|---|---|---|---|---|---|---|---|---|
| 1 | 1 | **YGRKKRRQRRRPPQ** | **GGG** | **SSPILSITISEDG** | | | dengue 2 | TAT | C-terminal |
| 5 | 2 | **RQIKIWFQNRRMKWKK** | **GGG** | **SSPILSITISEDG** | | | dengue 2 | penetratin | C-terminal |
| 6 | 3 | **RRRRRRRRRR** | **GGG** | **SSPILSITISEDG** | | | dengue 2 | R10 | C-terminal |
| 16 | 4 | **YGRKKRRQRRRPPQ** | **GGG** | **SSPILSITISEDG** | **GG** | **KDEL*** | dengue 2 | TAT | C-terminal |
| 26 | 5 | **YGRKKRRQRRRPPQ** | **GGG** | **QWPALPKIEAQDG** | | | diserio | TAT | N-terminal |
| 27 | 6 | **YGRKKRRQRRRPPQ** | **GGG** | **ASRNILVEVQDDG** | | | dengue1 | TAT | C-terminal |
| 28 | 7 | **YGRKKRRQRRRPPQ** | **GGG** | **VSRNLMITVDDDG** | | | dengue3 | TAT | C-terminal |
| 29 | 8 | **YGRKKRRQRRRPPQ** | **GGG** | **SSPIIEVKQDEDG** | | | dengue4 | TAT | C-terminal |
| 20 | 9 | **YGRKKRRQRRRPPQ** | **GGG** | **SSERVDVRLDDDG** | | | WNV | TAT | C-terminal |
| 31 | 10 | **YGRKKRRQRRRPPQ** | **bA** | **SSPILSITISEDG SMSI** | **GGG** | **GRR*** | dengue 2 | TAT | C-terminal |
| 39 | 11 | **YGRKKRRQRRRPPQ** | **GGG** | **DLELERAADVKWE** | | | dengue 2 | TAT | N-terminal |
| 47 | 12 | **RRRRRRRRRR** | **GGG** | **DLELERAADVKWE** | | | dengue 2 | R10 | N-terminal |

TABLE 1-continued

Design of chimerical peptides according to the topology [P]-[L1]-[I]-[L2]-[T]

| SEQ ID NO. | No | [P] | [L1] | [I] | [L2] | [T] | Virus | Penetrating peptide | Target domain |
|---|---|---|---|---|---|---|---|---|---|
| 55 | 13 | YGRKKRRQRRRPPQ | GGG | DLELERAADVKWE | GG | KDEL* | dengue 2 | TAT | N-terminal |
| 56 | 14 | YGRKKRRQRRRPPQ | GGG | DLSLEKAAEVSWE | | | dengue1 | TAT | N-terminal |
| 57 | 15 | YGRKKRRQRRRPPQ | GGG | DLTVEKAADVTWE | | | dengue3 | TAT | N-terminal |
| 58 | 16 | YGRKKRRQRRRPPQ | GGG | DL SLEKAANVQWD | | | dengue4 | TAT | N-terminal |
| 59 | 17 | YGRKKRRQRRRPPQ | GGG | DMWIERTADITWE | | | WNV | TAT | N-terminal |
| 63 | 18 | YGRKKRRQRRRPPQ | GGG | LEGSDISPSTISI | | | negative control | TAT | |
| 64 | 19 | YGRKKRRQRRRPPQ | | | | | negative control | TAT | |
| 65 | 20 | YGRKKRRQRRRPPQ | GGG | TGSVVIVGRIIL | | | HCV | TAT | N-terminal |
| 66 | 21 | YGRKKRRQRRRPPQ | GGG | TGSVVIVGQIIL | | | HCV | TAT | N-terminal |
| 67 | 22 | CSNIVIGIGDKALKINWC | bA | SSPILSITISEDG | | | dengue 2 | FG-den3 | C-terminal |
| 77 | 23 | CSNIVIGIGDKALKINWC | bA | DLELERAADVKWE | | | dengue 2 | FG-den3 | N-terminal |
| 85 | 24 | CSNIVIGIGDKALKINWC | bA | SSPILSITISEDG SMSI | GGG | GRR* | dengue 2 | FG-den3 | C-terminal |
| 93 | 25 | CSNIVIGIGDKALKINWC | bA | SSPILSITISEDG | GG | KDEL* | dengue 2 | FG-den3 | C-terminal |
| 103 | 26 | CSNIVIGIGDKALKINWC | bA | DLELERAADVKWE | GG | KDEL* | dengue 2 | FG-den3 | N-terminal |
| 111 | 27 | myr-bA-CSNIVIGIGDKALKINWC | bA | SSPILSITISEDG | bA | LRRRRL | dengue 2 | FG-den3 | C-terminal |
| 121 | 28 | myr-bA-CSNIVIGIGDKALKINWC | bA | DLELERAADVKWE | bA | LRRRRL | dengue 2 | FG-den3 | N-terminal |
| 111 | 29 | pal-bA-CSNIVIGIGDKALKINWC | bA | SSPILSITISEDG | bA | LRRRRL | dengue 2 | FG-den3 | C-terminal |
| 121 | 30 | pal-bA-CSNIVIGIGDKALKINWC | bA | DLELERAADVKWE | bA | LRRRRL | dengue 2 | FG-den3 | N-terminal |
| 129 | 31 | myr-bA-CSNIVIGIGDKALKINWC | bA | SSPILSITISEDG | | dengue 2 | FG-den3 | | C-terminal |
| 139 | 32 | myr-bA-CSNIVIGIGDKALKINWC | bA | DLELERAADVKWE | | dengue 2 | FG-den3 | | N-terminal |
| 129 | 33 | pal-bA-CSNIVIGIGDKALKINWC | bA | SSPILSITISEDG | | | dengue 2 | FG-den3 | C-terminal |
| 139 | 34 | pal-bA-CSNIVIGIGDKALKINWC | bA | DLELERAADVKWE | | | dengue 2 | FG-den3 | N-terminal |
| 147 | 35 | myr-bA-CSNIVIGIGDKALKINWC | bA | SSPILSITISEDG | bA | LRRRRLKDEL* | dengue 2 | FG-den3 | C-terminal |
| 148 | 36 | myr-bA-CSNIVIGIGDKALKINWC | bA | DLELERAADVKWE | bA | LRRRRLKDEL* | dengue 2 | FG-den3 | N-terminal |
| 147 | 37 | pal-bA-CSNIVIGIGDKALKINWC | bA | SSPILSITISEDG | bA | LRRRRLKDEL* | dengue 2 | FG-den3 | C-terminal |

TABLE 1-continued

| SEQ ID NO. | No | [P] | [L1] | [I] | [L2] | [T] | Virus | Penetrating peptide | Target domain |
|---|---|---|---|---|---|---|---|---|---|
| | | Design of chimerical peptides according to the topology [P]-[L1]-[I]-[L2]-[T] | | | | | | | |
| 148 | 38 | **pal-bA-CSNIVIGIGDKALKINWC** | **bA** | **DLELERAADVKWE** | **bA** | **LRRRRLKDEL*** | dengue 2 | FG-den3 | N-terminal |
| 364 | 39 | **RRRRRRRRRR** | **GGG** | **SSPILSITISEDG** | **GG** | **KDEL*** | dengue 2 | R10 | C-terminal |

*: carboxilic C-terminal end. Myr-: covalent attachment of a myristoyl group to the N-terminal end of the peptide. Pal-: covalent attachment of a palmitoyl group to the N-terminal end of the peptide. bA: beta-Alanine. FG-den3: sequence corresponding to the FG hairpin of domain III of the envelope protein from DV3, two cysteins bound by disulfide bridge are added at the N- and C-terminal ends of the segment.

TABLE 2

Design of chimerical peptides according to the topology [I]-[L3]-[P]-[L4]-[T]

| SEQ ID NO. | No | [I] | [L3] | [P] | [L4] | | Virus | Penetrating Peptide | Target domain |
|---|---|---|---|---|---|---|---|---|---|
| 158 | 1 | **SSPILSITISEDG** | **GGG** | **YGRKKRRQRRRPPQ** | | | dengue2 | TAT | C-terminal |
| 159 | 2 | **SSPILSITISEDG** | **GGG** | **RRRRRRRRRR** | | | dengue2 | R10 | C-terminal |
| 167 | 3 | **SSPILSITISEDG** | **GGG** | **RRRRRRRRRR** | **GG** | **KDEL*** | dengue2 | R10 | C-terminal |
| 175 | 4 | **SSPILSITISEDG** | **GGG** | **YGRKKRRQRRRPPQ** | **GG** | **KDEL*** | dengue2 | TAT | C-terminal |
| 183 | 5 | **ASHNILVEVQDDG** | **GGG** | **YGRKKRRQRRRPPQ** | | | dengue1 | TAT | C-terminal |
| 184 | 6 | **VSHNLMITVDDDG** | **GGG** | **YGRKKRRQRRRPPQ** | | | dengue3 | TAT | C-terminal |
| 185 | 7 | **SSPIIEVKQDEDG** | **GGG** | **YGRKKRRQRRRPPQ** | | | dengue4 | TAT | C-terminal |
| 182 | 8 | **SSERVDVRLDDDG** | **GGG** | **YGRKKRRQRRRPPQ** | | | WNV | TAT | C-terminal |
| 190 | 9 | **DLELERAADVKWE** | **GGG** | **YGRKKRRQRRRPPQ** | | | dengue2 | TAT | N-terminal |
| 200 | 10 | **DLELERAADVKWE** | **GGG** | **YGRKKRRQRRRPPQ** | **GG** | **KDEL*** | dengue2 | TAT | N-terminal |
| 210 | 11 | **DLELERAADVKWE** | **GGG** | **RRRRRRRRRR** | | | dengue2 | R10 | N-terminal |
| 211 | 12 | **DLELERAADVKWE** | **GGG** | **RRRRRRRRRR** | **GG** | **KDEL*** | dengue2 | R10 | N-terminal |
| 221 | 13 | **DLSLEKAAEVSWE** | **GGG** | **RRRRRRRRRR** | | | Dengue1 | R10 | N-terminal |
| 222 | 14 | **DLTVEKAADVTWE** | **GGG** | **RRRRRRRRRR** | | | Dengue3 | R10 | N-terminal |
| 223 | 15 | **DLSLEKAANVQWD** | **GGG** | **RRRRRRRRRR** | | | Dengue4 | R10 | N-terminal |
| 224 | 16 | **DMWIERTADITWE** | **GGG** | **RRRRRRRRRR** | | | WNV | R10 | N-terminal |
| 230 | 17 | **SSPILSITISEDG** | **bA** | **LRRRRLbALRRRRL** | **bA** | **KDEL*** | dengue2 | 2(LR4L) | C-terminal |
| 238 | 18 | **SSPILSITISEDG** | **bA** | **LRRRRLbALRRRRL** | | | dengue2 | 2(LR4L) | C-terminal |
| 246 | 19 | **SSPILSITISEDG** | **bA** | **LRRRRLRRRRL** | | | dengue2 | 2(LR4L) | C-terminal |
| 254 | 20 | **myr-SSPILSITISEDG** | **bA** | **LRRRRLRRRRL** | | | dengue2 | 2(LR4L) | C-terminal |
| 254 | 21 | **pal-SSPILSITISEDG** | **bA** | **LRRRRLRRRRL** | | | dengue2 | 2(LR4L) | C-terminal |
| 262 | 22 | **myr-SSPILSITISEDG** | **bA** | **LRRRRLbALRRRRL** | **bA** | **KDEL*** | dengue2 | 2(LR4L) | C-terminal |
| 270 | 23 | **myr-SSPILSITISEDG** | **bA** | **LRRRRLbALRRRRL** | | | dengue2 | 2(LR4L) | C-terminal |
| 262 | 24 | **pal-SSPILSITISEDG** | **bA** | **LRRRRLbALRRRRL** | **bA** | **KDEL*** | dengue2 | 2(LR4L) | C-terminal |
| 270 | 25 | **pal-SSPILSITISEDG** | **bA** | **LRRRRLbALRRRRL** | | | dengue2 | 2(LR4L) | C-terminal |

TABLE 2 -continued

Design of chimerical peptides according to the topology [I]-[L3]-[P]-[L4]-[T]

| SEQ ID NO. | No | [I] | [L3] | [P] | [L4] | | Virus | Penetrating Peptide | Target domain |
|---|---|---|---|---|---|---|---|---|---|
| 278 | 26 | DLELERAADVKWE | bA | LRRRRLbALRRRRL | bA | KDEL* | dengue2 | 2(LR4L) | N-terminal |
| 288 | 27 | myr-DLELERAADVKWE | bA | LRRRRLbALRRRRL | bA | KDEL* | dengue2 | 2(LR4L) | N-terminal |
| 288 | 28 | pal-DLELERAADVKWE | bA | LRRRRLbALRRRRL | bA | KDEL* | dengue2 | 2(LR4L) | N-terminal |
| 298 | 29 | DLELERAADVKWE | bA | LRRRRLRRRRL | | | dengue2 | 2(LR4L) | N-terminal |
| 299 | 30 | myr-DLELERAADVKWE | bA | LRRRRLRRRRL | | | dengue2 | 2(LR4L) | N-terminal |
| 299 | 31 | pal-DLELERAADVKWE | bA | LRRRRLRRRRL | | | dengue2 | 2(LR4L) | N-terminal |
| 309 | 32 | DLSLEKAAEVSWE | bA | LRRRRLRRRRL | | | Dengue1 | 2(LR4L) | N-terminal |
| 310 | 33 | DLTVEKAADVTWE | bA | LRRRRLRRRRL | | | Dengue3 | 2(LR4L) | N-terminal |
| 311 | 34 | DLSLEKAANVQWD | bA | LRRRRLRRRRL | | | Dengue4 | 2(LR4L) | N-terminal |
| 318 | 35 | DLELERAADVKWE | bA | CSNIVIGIGDKALKINWC | | | dengue2 | FG-den3 | N-terminal |
| 328 | 36 | myr-DLELERAADVKWE | bA | CSNIVIGIGDKALKINWC | bA | LRRRRL | dengue2 | FG-den3 | N-terminal |
| 328 | 37 | pal-DLELERAADVKWE | bA | CSNIVIGIGDKALKINWC | bA | LRRRRL | dengue2 | FG-den3 | N-terminal |
| 338 | 38 | myr-DLELERAADVKWE | bA | CSNIVIGIGDKALKINWC | bA | LRRRRLKDEL* | dengue2 | FG-den3 | N-terminal |
| 338 | 39 | pal-DLELERAADVKWE | bA | CSNIVIGIGDKALKINWC | bA | LRRRRLKDEL* | dengue2 | FG-den3 | N-terminal |
| 339 | 40 | SSPILSITISEDG | bA | CSNIVIGIGDKALKINWC | | | dengue2 | FG-den3 | C-terminal |
| 347 | 41 | myr-SSPILSITISEDG | bA | CSNIVIGIGDKALKINWC | bA | LRRRRL | dengue2 | FG-den3 | C-terminal |
| 347 | 42 | pal-SSPILSITISEDG | bA | CSNIVIGIGDKALKINWC | bA | LRRRRL | dengue2 | FG-den3 | C-terminal |
| 355 | 43 | myr-SSPILSITISEDG | bA | CSNIVIGIGDKALKINWC | bA | LRRRRLKDEL* | dengue2 | FG-den3 | C-terminal |
| 355 | 44 | pal-SSPILSITISEDG | bA | CSNIVIGIGDKALKINWC | bA | LRRRRLKDEL* | dengue2 | FG-den3 | C-terminal |

*: carboxilic C-terminal end. Myr-: covalent attachment of a myristoyl group to the N-terminal end of the peptide. Pal-: covalent attachment of a palmitoyl group to the N-terminal end of the peptide. bA: beta-Alanine. FG-den3: sequence corresponding to the FG hairpin of domain III of the envelope protein from DV3, two cysteins bound by disulfide bridge are added at the N- and C-terminal ends of the segment.

The present invention concerns also the design of antiviral chimerical peptides against the other members of the Flaviviridae family. Peptide inhibitors against other Flaviviridae include as [I] segments, the analogous segments from the corresponding NS2B protein sequence (in Flavivirus) or NS4A (in hapacivirus). In the list of sequences of the present invention we include additional chimerical peptides analogous to those shown on tables 1 and 2, whose [I] segment corresponds to other Flavivirus (YFV, JEV, TBE, WNV) and the Hepacivirus HCV.

As [P] segments we consider the TAT peptide, R10, penetratin, the cationic sequences LRRRRLRRRRL (SEQ ID NO: 366) and LRRRRL-bAla-RRRRL (SEQ ID NO: 365) and the segment 5376-W391 of the envelope protein of DV3 (loop FG of domain III). The later segment includes cysteines at its N- and C-terminal ends, which form a disulfide bridge and stabilize the beta hairpin conformation observed in the three dimensional structure of the envelope protein.

As terminal [T] segments we include the ER retention signals LRRRRL (SEQ ID NO: 367), KDEL and their combination LRRRRLKDEL (SEQ ID NO: 368). The presence of these signals enhances the effective localization of peptides in the ER, which affect favorably their antiviral activity. We also include as [T] segment the sequence GRR, linked by the tripeptide GGG to the [I] segment of sequence $S_{70}$-$I_{86}$. As shown in FIG. 1C, peptides with this primary structure bind to the C-terminal domain of NS3pro protein and the GRR segment localizes at the protease active site, blocking its interaction with substrates. As linker segments we include in table 1 and 2 the tripeptide GGG, the dipeptide GG and the amino acid beta-Alanine.

Peptides myristoylated and palmitoylated at the N-terminal end are also included. The lipidation of these peptides increases the efficiency of the adhesion to the plasma membrane, cell entry and the final localization in the RE membrane. Lipidation is carried out by chemical methods. In the table 1 and 2, the lipids are attached directly to the N-terminal ends or to an N-terminal beta-Alanine residue.

Various peptides segments included in table 1 and 2 display more than one single function. The segments LRRRRLR-RRRL (SEQ ID NO: 365) and LRRRRL-bAla-RRRRL (SEQ ID NO: 366) besides being cell penetrating peptides comprise two consecutive ER retention signals.

The [P] segment corresponding to the sequence of the region S376-W391 of the envelope protein from DV3, besides being a cell penetrating peptide, is also an inhibitor of the virus entry into the cells. Therefore the use of this segment in peptides of the present invention increases the inhibitory effect of these peptides.

The peptides of the present invention could be obtained by chemical synthesis o by recombinant DNA technology, alone or as part of fusion proteins. Expression as fusion proteins can increase the expression levels and stability of peptides against degradation by host proteases. These peptide sequences could be joined to the fusion proteins through linkers corresponding to substrate sequences of specific proteases, and thus the peptides can be isolated by successive proteolysis and purification.

Peptide Synthesis

Solid phase peptide synthesis was performed on an Fmoc-AM-MBHA resin, using the Fmoc/tBu strategy (Barany, G. and Merrifield, R. B. *J Am Chem. Soc.* 99 (1977) 7363-7365). The synthesis was carried out manually in 10 ml syringes equipped with porous frit and all reactive and solvents were discarded by vacuum filtration. The amino acids were coupled by activation with DIC/HOBt, monitoring the completion of the coupling reaction by the ninhydrin assay (Kaiser, E., Colescott, R. L., Bossinger, C. D., Cook, P. I. Anal Biochem. 34 (1970) 595-598).

The synthesized peptides were detached from the resin by treatment with a solution of TFA/EDT/H2O/TIS (94%/2.5%/2.5%/1%), precipitated with ether, and lyophilized during 72 h. Peptide cyclization by forming a disulphide bridge was achieved by oxidation with DMSO (Andreu, D., Albericio, F., Sol, N. A., Munson, M. C., Ferrer, M. and Barany, G., Pennington, M. W. and Dunn, B. M. (Eds), Peptide Synthesis Protocols, Methods in Molecular Biology, Totowa, N.J., 1994, pp. 91-169). In all cases, the peptides were purified by RP-HPLC and the collected fractions were analyzed again by analytical RP-HPLC. The final preparation of each peptide was obtained by pooling the fractions with a chromatographic purity equal to or higher than 99%. The mass of the peptide on each final preparation was verified by ESI-MS mass spectrometry.

The mass spectra were acquired with a hybrid mass spectrometer with octagonal geometry QTOF-2™ (Micromass, UK), equipped with a Z-spray electronebulization ionization source.

The software used for the acquisition and processing of the spectra was MassLinx, ver. 3.5 (Waters, USA).

Example 2

Inhibition of Viral Infection in Vero Cells

In order to prove the antiviral activity in vitro of chimerical peptides described on the present invention, the peptides were tested in plaque reduction neutralization assay in Vero cells (PRNT). Vero cells were grown in 24-well plates to approximately 90% confluence, and washed twice with MEM medium without FCS. Peptide dilutions were added according to the particular assay and incubated typically during 1 h at 37° C. After the incubation, the virus was added at a multiplicity of infection of 0.1, followed by a subsequent incubation for 1 hour at 37 C. In certain experiments the peptides were added simultaneously with the virus (without preincubation) or the peptide preincubation time was modified. At the end of the second incubation, the unbound virus was eliminated by washing, and the cells were incubated for 5 days at 37 C in high density medium (MEM supplemented with non essential amino acids, 1% FCS, 1% carboxymethylcellulose) in order to propitiate the appearance of lytic plaques. The plaques were visualized by staining with 0.1% Naphtol Blue Black in 0.15 Mol/L sodium acetate. Two replicates were used per experimental point in each assay, and three independent determinations were performed. The inhibition percentage was calculated according to the expression:

$$100x\left[1-\frac{No.plaques}{No.Plaques.virus.control.}\right]$$

Figure 2:
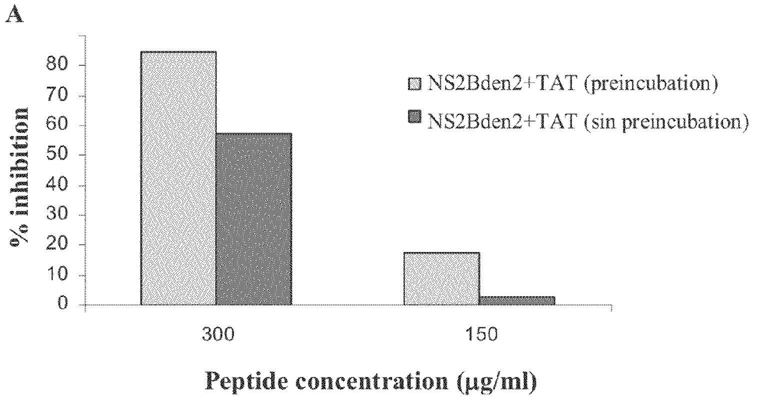
FIG. 2: Assay of inhibition of infection by dengue 2 virus in Vero cells. A: Percentage of reduction in the number of plaques due to the presence of peptide NS2Bden2+TAT with and without preincubation before addition of the virus to the cells. B: Assay of the antiviral activity of peptides TAT and NS2Bden2+TAT at different concentrations, with (pre) and without preincubation (no pre).
Figure 2:
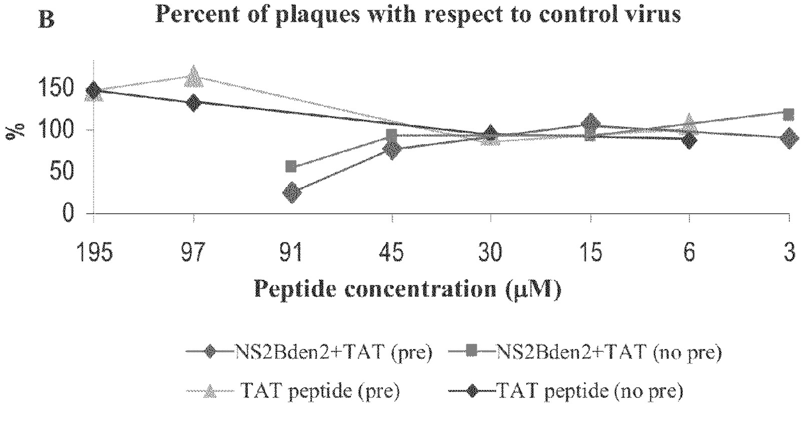

The FIG. 2 shows that peptide NS2Bden2+TAT (peptide 1 of the table 1) inhibit the infection by DV2, in a dose dependent manner, with a 1050 of approximately 50-60 μM. The peptides showed no signs of toxicity on the cells at the assayed conditions. The sequence of peptide NS2Bden2+TAT contains two essential modules: the cell penetrating segment TAT and the protease NS3pro activation inhibitor segment, which targets the C-terminal domain of the protease. The TAT peptide did not show antiviral activity and caused an increase in the number of plaques (FIG. 2B). This result is consistent with the peptide design: the antiviral activity residing on the segment specifically related to the VD2 (strain S16803). The observed enhancement of the virus infection in presence of the TAT peptide could be related to an increase in the entry of the virus into the cells facilitated by the PTD property of this peptide. Increasing cell penetration of viruses mediated by PTD has been previously observed in other systems (Gratton J P, Yu J, Griffith J W, et al. *Cell-permeable peptides improve cellular uptake and therapeutic gene delivery of replication-deficient viruses in cells and in vivo. Nat Med* 2003; 9: 357-63).

Figure 5:
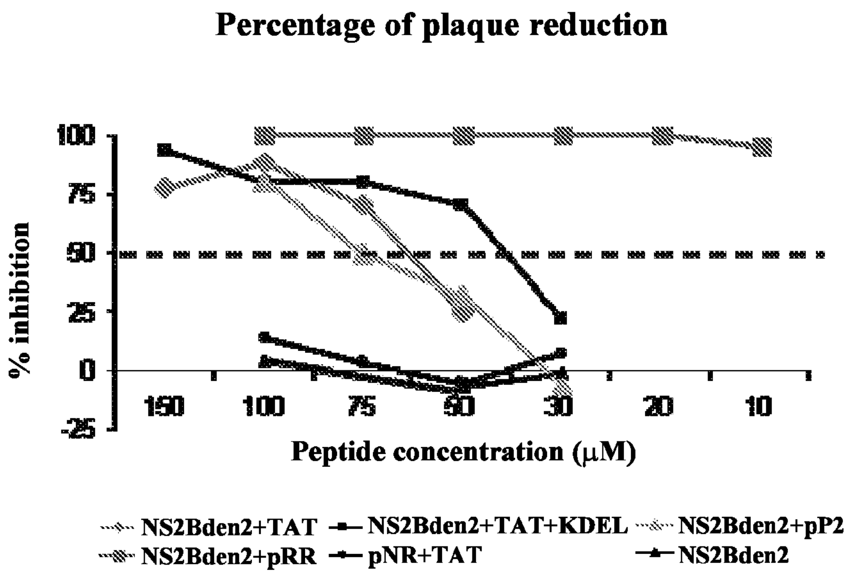
FIG. 5: Effect of penetrating peptide identity and ER retention signal on the antiviral activity of peptides. NS2Bden2+

The presence of the TAT peptide segment in the sequence of peptide NS2Bden2+TAT is necessary for its antiviral activity, because the NS3pro protease activation inhibitor segment [I] per se does not show antiviral activity in vitro (FIG. 5).

The FIG. 2 shows that the antiviral activity of the chimerical peptide NS2Bden2+TAT increases if the peptide is preincubated with cells 1 h before the addition of the virus. This result is consistent with the fact that the target for the antiviral activity of the peptide is an intracellular event, and preincubation allows a higher amount of peptide to penetrate into the cells and localize at the ER membrane, previously to the beginning of the virus replication.

Figure 3:
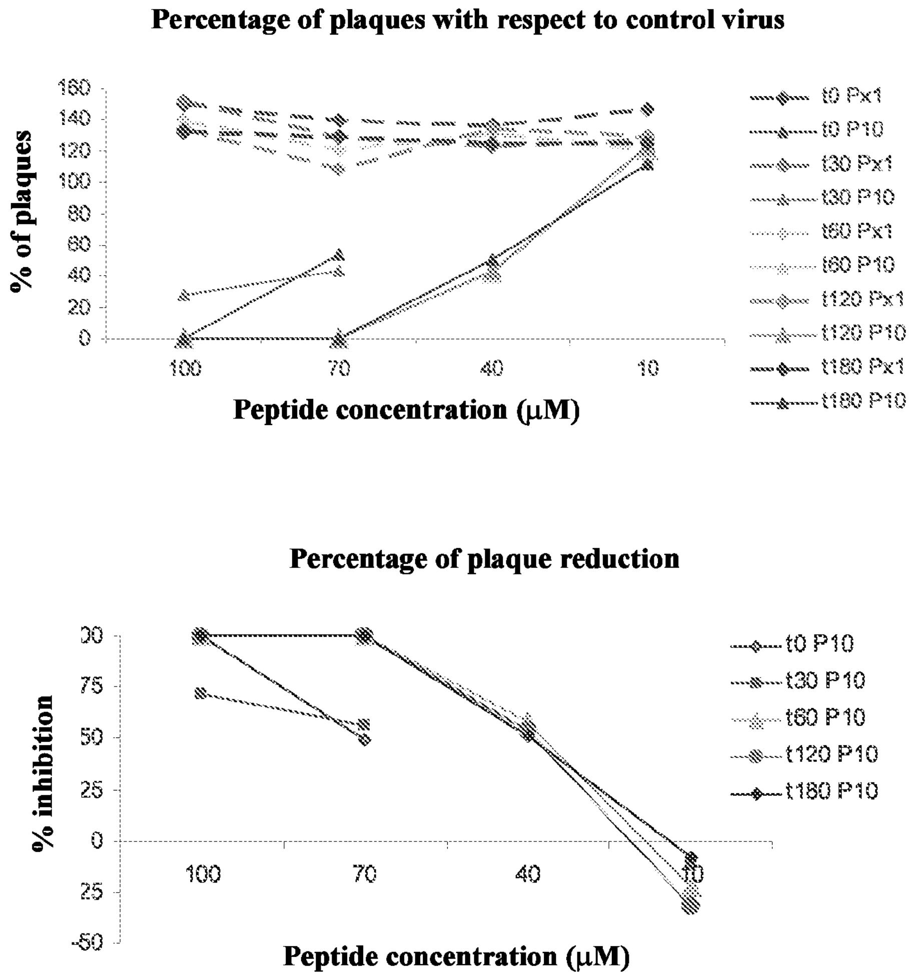
FIG. 3: Effect of incubation time on the antiviral activity of peptide NS2Bden2+TAT. PX1: not related negative control peptide (TAT peptide fusion to a not related sequence); P10: peptide NS2Bden2+TAT (TAT fusion to a peptide from NS2B of DV, peptide No. 1 of table 1). The assayed preincubation times were 0, 30, 60 and 180 minutes.

In order to characterize the effect of preincubation on the antiviral activity of peptide NS2Bden2+TAT we studied the relationship between plaque reduction neutralization, preincubation time and peptide dose. As negative control we used a non related chimerical peptide displaying an structure similar to NS2Bden2+TAT. This peptide contains at the N-terminal end the sequence of the TAT peptide and at its C-terminal end a sequence which have been shown to bind to the protein E7 from human papilloma virus. The FIG. 3 shows that for peptide concentrations less than 100 μM, preincubation is necessary for the antiviral activity and this activity increases with the time of preincubation between 0 and 1 hour. This result is consistent with the intracellular localization of the target for the antiviral effect and the need for peptide transport from the extracellular space to the cytosol.

However, between 1 and 3 hours of preincubation, we do not observe more differences. One possible explanation could be that at these times equilibrium is reached between the kinetics of accumulation of peptide in the cytosol and the intracellular degradation of the peptide.

The negative control peptide does not show antiviral activity at any of the assayed conditions indicating that the antiviral effect of the peptide NS2Bden2+TAT is due specifically to the sequence of the segment corresponding to the NS2B protein.

Figure 4:
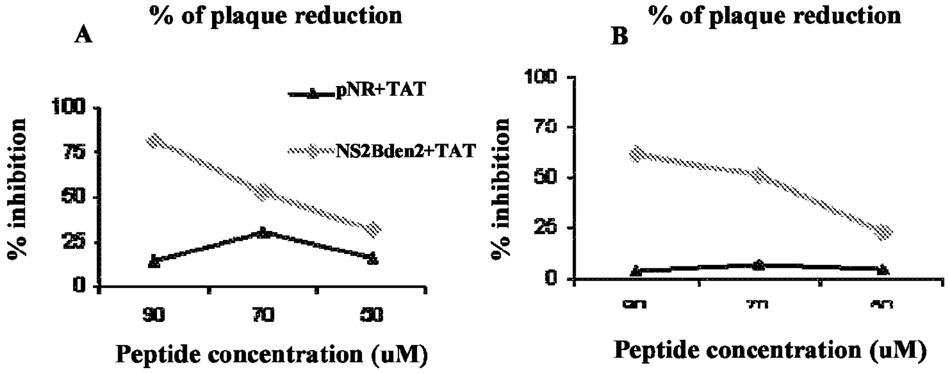
FIG. 4: Role of internalization on the antiviral activity of peptide NS2Bden2+TAT. A: After preincubation with peptides, they remain present in the media at the time of virus addition to the cells. B: The peptides are retired from the media, through various washing before virus addition to the cells. pNR+TAT: peptide No. 18 of table 1. The pNR+TAT peptide is a negative control of the experiment. Its primary structure is analog to peptide NS2Bden2+TAT, the [I] segment have an amino acid composition identical to peptide NS2Bden2+TAT but the sequence was permutated (peptide 18 of table 1).

FIG. 4 shows additional evidence indicating that the antiviral activity of the peptide NS2Bden2+TAT is related to an intracellular effect. In this case, besides the previously described usual assay conditions (FIG. 4A), the antiviral activity of the peptide was also determined when the peptide was retired from the media by successive washing of cells previous to the addition of the virus (FIG. 4B). In both conditions of the assay, the antiviral activity of the peptide was very similar, indicating that the antiviral effect depends on previously internalized peptide. In these assays, the peptide 18 of table 1 was used as negative control. This peptide has a design similar to the peptide NS2Bden2+TAT, but the C-terminal segment consists of a sequence of the same length and amino acid composition as the NS3pro protease activation inhibitor [I] segment of NS2Bden2+TAT, but the original sequence was randomized. This peptide did not show antiviral activity in any condition, indicating that the antiviral activity of NS2Bden2+TAT depends on the selected sequence fragment of NS2B.

Example 3

Effect of the Nature of the Cell Penetrating Peptide and the ER Retention Signal on the Antiviral Activity of Peptides In order to determine the role of the cell penetrating peptide and the ER retention signal on the antiviral activity of peptides of the present invention we tested peptides No 1, 2, 3 and 4 of table 1 for inhibition of the viral infection by VD2 in Vero cells, using the assay described in the example 2.

The peptides 2 and 3 have a primary structure similar to the peptide NS2Bden2+TAT (péptido 1), but displaying penetratin and decarginine respectively as cell penetrating segments. The peptide 4 consists on the addition of the KDEL signal at the C-terminal end of peptide NS2Bden2+TAT. The C-terminal group of peptide 4 is carboxylic in order to make functional the ER retention signal.

The FIG. 5 and the table 3 show that the peptide NS2Bden2-pRR (peptide 3 on table 1) displays the higher antiviral activity, almost an order more potent than the peptide NS2Bden2+TAT. One possible explanation is that decaarginine peptide is more resistant to proteolysis in the intracellular environment of the cell ((Fischer, R., Kohler, K., Fotin-Mleczek, M., and Brock, R. 2004. *A stepwise dissection of the intracellular fate of cationic cell-penetrating peptides. J. Biol. Chem.* 279, 12625-35). The peptide NS2Bden2-pP2 (peptide 2) shows an antiviral activity similar to NS2Bden2+TAT, however it displays significant cytotoxicity. The addition of the KDEL signal increase slightly the antiviral activity of the peptide, suggesting that the peptide NS2Bden2+TAT uses at least partially the retrograde transport to get access into the cytosol.

The peptide NS2Bden2 which lacks the cell penetrating segment does not inhibit the antiviral infection, showing that the inclusion of this kind of segment is required in the peptides of the present invention.

TABLE 3

PRNT50 and cytotoxicity (CTE) of peptides in Vero cells

| Peptide | PRNT50 | CTE |
|---|---|---|
| NS2Bden2 + TAT | 60 μM | 150 μM |
| NS2Bden2 + TAT + KDEL | 40 μM | >150 μM |
| NS2Bden2-pRR | <10 μM | >50 μM |
| NS2Bden2-pP2 | 75 μM | 50 μM |
| NS2Bden2 | — | — |

CTE: cytotoxic effect, the values indicate peptide concentrations causing damage to 50% of the monolayer.

Example 4

Antiviral Activity of Peptides Against Homologous and Heterologous Virus

An expected property of antiviral agents is to possess a wide spectrum of antiviral activity, at least against the related most similar viruses. This is also the case in the development of antiviral molecules against dengue virus: 1) dengue is actually a complex of four different viruses, 2) there are difficulties for an early specific diagnosis and 3) in the affected countries, dengue is frequently endemic, occurring the cocirculation of more that one serotype.

The four dengue serotypes are related viruses with similar amino acid sequences (70-80% identity) of their structural and non structural proteins. Therefore, it is reasonable that differences in the amino acid sequences of NS2B and/or NS3pro could affect the infection inhibitory capacity of peptides of the present invention against the heterologous viruses.

In order to evaluate the cross-reactivity or serotype specificity of the antiviral activity of peptides of the present invention, we tested peptides 1, 3 and 6 of the table 1 for inhibition of the viral infection by DV1-3 in Vero cells, using the assay described in the example 2. The tested viral strains were West Pac 74 of DV1, S16803 of DV2 and CH53489 of DV3. The peptide 6 (NS2Bden1+TAT) has a primary structure similar to NS2Bden2+TAT, but it has a NS3 activation inhibitor segment corresponding the protein NS2B from DV1. We also included in the analysis the peptide 5, designed by computational methods.

The FIG. 6 shows that the peptide NS2Bden2+pRR (peptide 3 on table 1) is equally potent against the three serotypes. The peptide NS2Bden2+TAT also inhibits the serotypes 1-3 although with a lower antiviral activity. The peptide NS2Bden1+TAT (peptide 6) however shows only partial inhibition against serotypes 1 and 3. This result is consistent with the fact that serotypes 1 and 3 are phylogenetically closer to each other and their proteins are more similar.

INCORPORATION OF SEQUENCE LISTING

Incorporated herein by reference in its entirety is the Sequence Listing for the application. The Sequence Listing is disclosed on a computer-readable ASCII text file titled, “sequence_listing.txt”, created on May 3, 2013. The sequence_listing.txt file is 384 kb in size.

SEQUENCE LISTING

<160> NUMBER OF SEQ ID NOS: 382

<210> SEQ ID NO 1
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker sequence
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the virus DV2

<400> SEQUENCE: 1

```
Tyr Gly Arg Lys Lys Arg Arg Gln Arg Arg Arg Pro Pro Gln Gly Gly
  1               5                  10                  15

Gly Ser Ser Pro Ile Leu Ser Ile Thr Ile Ser Glu Asp Gly
             20                  25                  30
```

<210> SEQ ID NO 2
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the YFV

<400> SEQUENCE: 2

```
Tyr Gly Arg Lys Lys Arg Arg Gln Arg Arg Arg Pro Pro Gln Gly Gly
  1               5                  10                  15

Gly Ser Ser Ala Arg Tyr Asp Val Ala Leu Ser Glu Gln Gly
             20                  25                  30
```

<210> SEQ ID NO 3
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the JEV

<400> SEQUENCE: 3

```
Tyr Gly Arg Lys Lys Arg Arg Gln Arg Arg Arg Pro Pro Gln Gly Gly
  1               5                  10                  15

Gly Ser Ser Arg Arg Leu Asp Val Lys Leu Asp Asp Asp Gly
             20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the Tick-Borne
Encephalitis virus

<400> SEQUENCE: 4

```
Tyr Gly Arg Lys Lys Arg Arg Gln Arg Arg Arg Pro Pro Gln Gly Gly
  1               5                  10                  15

Gly Gly Glu Val Ser Leu Arg Val Arg Gln Asp Ala Met Gly
             20                  25                  30
```

<210> SEQ ID NO 5
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(16)
<223> OTHER INFORMATION: cell penetrating peptide penetratin
<220> FEATURE:
<221> NAME/KEY: DOMAIN
<222> LOCATION: (17)..(19)
<223> OTHER INFORMATION: linker segment
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the virus DV2

<400> SEQUENCE: 5

```
Arg Gln Ile Lys Ile Trp Phe Gln Asn Arg Arg Met Lys Trp Lys Lys
  1               5                  10                  15

Gly Gly Gly Ser Ser Pro Ile Leu Ser Ile Thr Ile Ser Glu Asp Gly
```

-continued 20 25 30

<210> SEQ ID NO 6
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro C-terminal domain binding segment,
segment of NS2B from the virus DV2

<400> SEQUENCE: 6

Arg Arg Arg Arg Arg Arg Arg Arg Arg Arg Gly Gly Gly Ser Ser Pro
1 5 10 15

Ile Leu Ser Ile Thr Ile Ser Glu Asp Gly
20 25

<210> SEQ ID NO 7
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro C-terminal domain binding segment,
segment of NS2B from the YFV

<400> SEQUENCE: 7

Arg Arg Arg Arg Arg Arg Arg Arg Arg Arg Gly Gly Gly Ser Ser Ala
1 5 10 15

Arg Tyr Asp Val Ala Leu Ser Glu Gln Gly
20 25

<210> SEQ ID NO 8
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment -continued
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the JEV

<400> SEQUENCE: 8

```
Arg Arg Arg Arg Arg Arg Arg Arg Arg Arg Gly Gly Gly Ser Ser Arg
  1               5                  10                  15

Arg Leu Asp Val Lys Leu Asp Asp Asp Gly
             20                  25
```

<210> SEQ ID NO 9
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the Thick-Borne
      Encephalitis virus

<400> SEQUENCE: 9

```
Arg Arg Arg Arg Arg Arg Arg Arg Arg Arg Gly Gly Gly Gly Glu Val
  1               5                  10                  15

Ser Leu Arg Val Arg Gln Asp Ala Met Gly
             20                  25
```

<210> SEQ ID NO 10
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the WNV

<400> SEQUENCE: 10

```
Arg Arg Arg Arg Arg Arg Arg Arg Arg Arg Gly Gly Gly Ser Ser Glu
  1               5                  10                  15

Arg Val Asp Val Arg Leu Asp Asp Asp Gly
             20                  25
```

<210> SEQ ID NO 11

-continued

<211> LENGTH: 25
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(25)
<223> OTHER INFORMATION: NS3pro activation inhibitor segment, NS3pro N-terminal domain binding segment, segment of NS4A from the HCV

<400> SEQUENCE: 11

Arg Arg Arg Arg Arg Arg Arg Arg Arg Arg Gly Gly Gly Thr Gly Ser
1 5 10 15

Val Val Ile Val Gly Arg Ile Ile Leu
20 25

<210> SEQ ID NO 12
<211> LENGTH: 25
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(25)
<223> OTHER INFORMATION: NS3pro activation inhibitor segment, NS3pro N-terminal domain binding segment, segment of NS4A from the HCV, mutated at R22 by Q

<400> SEQUENCE: 12

Arg Arg Arg Arg Arg Arg Arg Arg Arg Arg Gly Gly Gly Thr Gly Ser
1 5 10 15

Val Val Ile Val Gly Gln Ile Ile Leu
20 25

<210> SEQ ID NO 13
<211> LENGTH: 26
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)

<223> OTHER INFORMATION: NS3pro activation inhibitor segment,
NS3pro C-terminal domain binding segment,
segment of NS2B from the virus dengue 1

<400> SEQUENCE: 13

Arg Arg Arg Arg Arg Arg Arg Arg Arg Arg Gly Gly Gly Ala Ser His
1 5 10 15

Asn Ile Leu Val Glu Val Gln Asp Asp Gly
20 25

<210> SEQ ID NO 14
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro C-terminal domain binding segment,
segment of NS2B from the virus dengue 3

<400> SEQUENCE: 14

Arg Arg Arg Arg Arg Arg Arg Arg Arg Arg Gly Gly Gly Val Ser His
1 5 10 15

Asn Leu Met Ile Thr Val Asp Asp Asp Gly
20 25

<210> SEQ ID NO 15
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro C-terminal domain binding segment,
segment of NS2B from the virus dengue 4

<400> SEQUENCE: 15

Arg Arg Arg Arg Arg Arg Arg Arg Arg Arg Gly Gly Gly Ser Ser Pro
1 5 10 15

Ile Ile Glu Val Lys Gln Asp Glu Asp Gly
20 25

<210> SEQ ID NO 16
<211> LENGTH: 36
<212> TYPE: PRT
<213> ORGANISM: Artificial Sequence
<220> FEATURE:

<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the virus DV2
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 16

```
Tyr Gly Arg Lys Lys Arg Arg Gln Arg Arg Arg Pro Pro Gln Gly Gly
  1               5                  10                  15

Gly Ser Ser Pro Ile Leu Ser Ile Thr Ile Ser Glu Asp Gly Gly Gly
             20                  25                  30

Lys Asp Glu Leu
         35
```

<210> SEQ ID NO 17
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the YFV
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 17

```
Tyr Gly Arg Lys Lys Arg Arg Gln Arg Arg Arg Pro Pro Gln Gly Gly
  1               5                  10                  15

Gly Ser Ser Ala Arg Tyr Asp Val Ala Leu Ser Glu Gln Gly Gly Gly
             20                  25                  30

Lys Asp Glu Leu
```

35

<210> SEQ ID NO 18
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 18

Tyr Gly Arg Lys Lys Arg Arg Gln Arg Arg Arg Pro Pro Gln Gly Gly
1 5 10 15

Gly Ser Ser Arg Arg Leu Asp Val Lys Leu Asp Asp Asp Gly Gly Gly
20 25 30

Lys Asp Glu Leu
35

<210> SEQ ID NO 19
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the Thick-Borne
Encephalitis virus
<220> FEATURE:
<221> NAME/KEY: DOMAIN
<222> LOCATION: (31)..(33)
<223> OTHER INFORMATION: linker segment
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL

<400> SEQUENCE: 19

```
Tyr Gly Arg Lys Lys Arg Arg Gln Arg Arg Arg Pro Pro Gln Gly Gly
  1               5                  10                  15

Gly Gly Glu Val Ser Leu Arg Val Arg Gln Asp Ala Met Gly Gly Gly
             20                  25                  30

Lys Asp Glu Leu
         35
```

<210> SEQ ID NO 20
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment, NS3pro C-terminal domain binding segment, segment of NS2B from the WNV
<220> FEATURE:
<221> NAME/KEY: DOMAIN
<222> LOCATION: (31)..(32)
<223> OTHER INFORMATION: linker segment
<220> FEATURE:
<221> NAME/KEY: DOMAIN
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 20

```
Tyr Gly Arg Lys Lys Arg Arg Gln Arg Arg Arg Pro Pro Gln Gly Gly
  1               5                  10                  15

Gly Ser Ser Glu Arg Val Asp Val Arg Leu Asp Asp Asp Gly Gly Gly
             20                  25                  30

Lys Asp Glu Leu
         35
```

<210> SEQ ID NO 21
<211> LENGTH: 35
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(29)
<223> OTHER INFORMATION: NS3pro activation inhibitor segment, NS3pro N-terminal domain binding segment, segment NS4A from HCV
<220> FEATURE:
<221> NAME/KEY: DOMAIN
<222> LOCATION: (30)..(31)
<223> OTHER INFORMATION: linker segment
<220> FEATURE:
<221> NAME/KEY: SIGNAL
<222> LOCATION: (32)..(35)
<223> OTHER INFORMATION: ER Retention signal KDEL
<220> FEATURE:
<223> OTHER INFORMATION: Carboxylic C-terminal end

<400> SEQUENCE: 21

```
Tyr Gly Arg Lys Lys Arg Arg Gln Arg Arg Arg Pro Pro Gln Gly Gly
  1               5                  10                  15

Gly Thr Gly Ser Val Val Ile Val Gly Arg Ile Ile Leu Gly Gly Lys
             20                  25                  30

Asp Glu Leu
         35
```

<210> SEQ ID NO 22
<211> LENGTH: 35
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(29)
<223> OTHER INFORMATION: NS3pro activation inhibitor segment, NS3pro N-terminal domain binding segment, segment NS4A from HCV, mutation of R28 by Q
<220> FEATURE:
<221> NAME/KEY: DOMAIN
<222> LOCATION: (30)..(31)
<223> OTHER INFORMATION: linker segment
<220> FEATURE:
<221> NAME/KEY: SIGNAL
<222> LOCATION: (32)..(35)
<223> OTHER INFORMATION: ER Retention signal KDEL
<220> FEATURE:
<223> OTHER INFORMATION: Carboxylic C-terminal end

<400> SEQUENCE: 22

```
Tyr Gly Arg Lys Lys Arg Arg Gln Arg Arg Arg Pro Pro Gln Gly Gly
  1               5                  10                  15

Gly Thr Gly Ser Val Val Ile Val Gly Gln Ile Ile Leu Gly Gly Lys
             20                  25                  30

Asp Glu Leu
         35
```

<210> SEQ ID NO 23
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:

-continued

<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment, NS3pro C-terminal domain binding segment, segment of NS2B from the virus dengue 1
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 23

```
Tyr Gly Arg Lys Lys Arg Arg Gln Arg Arg Arg Pro Pro Gln Gly Gly
  1               5                  10                  15

Gly Ala Ser His Asn Ile Leu Val Glu Val Gln Asp Asp Gly Gly Gly
             20                  25                  30

Lys Asp Glu Leu
         35
```

<210> SEQ ID NO 24
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment, NS3pro C-terminal domain binding segment, segment of NS2B from the virus dengue 3
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 24

```
Tyr Gly Arg Lys Lys Arg Arg Gln Arg Arg Arg Pro Pro Gln Gly Gly
  1               5                  10                  15

Gly Val Ser His Asn Leu Met Ile Thr Val Asp Asp Asp Gly Gly Gly
             20                  25                  30

Lys Asp Glu Leu
         35
```

<210> SEQ ID NO 25
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro C-terminal domain binding segment,
segment of NS2B from the virus dengue 4
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 25

```
Tyr Gly Arg Lys Lys Arg Arg Gln Arg Arg Arg Pro Pro Gln Gly Gly
  1               5                  10                  15

Gly Ser Ser Pro Ile Ile Glu Val Lys Gln Asp Glu Asp Gly Gly Gly
             20                  25                  30

Lys Asp Glu Leu
         35
```

<210> SEQ ID NO 26
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro N-terminal domain binding segment,
secuencia disenada computacionalmente

<400> SEQUENCE: 26

```
Tyr Gly Arg Lys Lys Arg Arg Gln Arg Arg Arg Pro Pro Gln Gly Gly
  1               5                  10                  15

Gly Gln Trp Pro Ala Leu Pro Lys Ile Glu Ala Gln Asp Gly
             20                  25                  30
```

<210> SEQ ID NO 27
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN

```
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro C-terminal domain binding segment,
      segment of NS2B from the virus dengue 1

<400> SEQUENCE: 27

Tyr Gly Arg Lys Lys Arg Arg Gln Arg Arg Arg Pro Pro Gln Gly Gly
  1               5                  10                  15

Gly Ala Ser His Asn Ile Leu Val Glu Val Gln Asp Asp Gly
             20                  25                  30


<210> SEQ ID NO 28
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro C-terminal domain binding segment,
      segment of NS2B from the virus dengue 3

<400> SEQUENCE: 28

Tyr Gly Arg Lys Lys Arg Arg Gln Arg Arg Arg Pro Pro Gln Gly Gly
  1               5                  10                  15

Gly Val Ser His Asn Leu Met Ile Thr Val Asp Asp Asp Gly
             20                  25                  30


<210> SEQ ID NO 29
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro C-terminal domain binding segment,
      segment of NS2B from the virus dengue 4

<400> SEQUENCE: 29

Tyr Gly Arg Lys Lys Arg Arg Gln Arg Arg Arg Pro Pro Gln Gly Gly
  1               5                  10                  15
```

```
Gly Ser Ser Pro Ile Ile Glu Val Lys Gln Asp Glu Asp Gly
            20                  25                  30


<210> SEQ ID NO 30
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro C-terminal domain binding segment,
      segment of NS2B from the WNV

<400> SEQUENCE: 30

Tyr Gly Arg Lys Lys Arg Arg Gln Arg Arg Arg Pro Pro Gln Gly Gly
  1               5                  10                  15

Gly Ser Ser Glu Arg Val Asp Val Arg Leu Asp Asp Asp Gly
            20                  25                  30


<210> SEQ ID NO 31
<211> LENGTH: 38
<212> TYPE: PRT
<213> ORGANISM: Artificial Sequence
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment,
      NS3pro C-terminal domain binding segment,
      segment of NS2B from the virus DV2
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
      protease NS3pro
<220> FEATURE:
<223> OTHER INFORMATION: Description of the Artificial Sequence:
      chimerical peptide
<220> FEATURE:
<223> OTHER INFORMATION: Carboxylic C-terminal end

<400> SEQUENCE: 31

Tyr Gly Arg Lys Lys Arg Arg Gln Arg Arg Arg Pro Pro Gln Ala Ser
  1               5                  10                  15

Ser Pro Ile Leu Ser Ile Thr Ile Ser Glu Asp Gly Ser Met Ser Ile
            20                  25                  30

Gly Gly Gly Gly Arg Arg
        35
```

<210> SEQ ID NO 32
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment,
NS3pro C-terminal domain binding segment,
segment of NS2B from the YFV
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
protease NS3pro
<220> FEATURE:
<223> OTHER INFORMATION: Carboxylic C-terminal end

<400> SEQUENCE: 32

Tyr Gly Arg Lys Lys Arg Arg Gln Arg Arg Arg Pro Pro Gln Ala Ser
1 5 10 15

Ser Ala Arg Tyr Asp Val Ala Leu Ser Glu Gln Gly Glu Phe Lys Leu
20 25 30

Gly Gly Gly Gly Arg Arg
35

<210> SEQ ID NO 33
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
protease NS3pro
<220> FEATURE:
<223> OTHER INFORMATION: Carboxylic C-terminal end

<400> SEQUENCE: 33

Tyr Gly Arg Lys Lys Arg Arg Gln Arg Arg Arg Pro Pro Gln Ala Ser
1 5 10 15

Ser Arg Arg Leu Asp Val Lys Leu Asp Asp Asp Gly Asp Phe His Leu
20 25 30

Gly Gly Gly Gly Arg Arg
35

<210> SEQ ID NO 34
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment, NS3pro C-terminal domain binding segment, segment of NS2B from the Thick-Borne Encephalitis virus
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral protease NS3pro
<220> FEATURE:
<223> OTHER INFORMATION: Carboxylic C-terminal end

<400> SEQUENCE: 34

Tyr Gly Arg Lys Lys Arg Arg Gln Arg Arg Arg Pro Pro Gln Ala Gly
1 5 10 15

Glu Val Ser Leu Arg Val Arg Gln Asp Ala Met Gly Asn Leu His Leu
20 25 30

Gly Gly Gly Gly Arg Arg
35

<210> SEQ ID NO 35
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment, NS3pro C-terminal domain binding segment, segment of NS2B from the WNV
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
protease NS3pro
<220> FEATURE:
<223> OTHER INFORMATION: Carboxylic C-terminal end

<400> SEQUENCE: 35

```
Tyr Gly Arg Lys Lys Arg Arg Gln Arg Arg Arg Pro Pro Gln Ala Ser
  1               5                  10                  15

Ser Glu Arg Val Asp Val Arg Leu Asp Asp Asp Gly Asn Phe Gln Leu
             20                  25                  30

Gly Gly Gly Gly Arg Arg
         35
```

<210> SEQ ID NO 36
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment,
NS3pro C-terminal domain binding segment,
segment of NS2B from the virus dengue 1
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
protease NS3pro
<220> FEATURE:
<223> OTHER INFORMATION: Carboxylic C-terminal end

<400> SEQUENCE: 36

```
Tyr Gly Arg Lys Lys Arg Arg Gln Arg Arg Arg Pro Pro Gln Ala Ala
  1               5                  10                  15

Ser His Asn Ile Leu Val Glu Val Gln Asp Asp Gly Thr Met Lys Ile
             20                  25                  30

Gly Gly Gly Gly Arg Arg
         35
```

<210> SEQ ID NO 37
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment,
NS3pro C-terminal domain binding segment,
segment of NS2B from the virus dengue 3
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
protease NS3pro
<220> FEATURE:
<223> OTHER INFORMATION: Carboxylic C-terminal end

<400> SEQUENCE: 37

```
Tyr Gly Arg Lys Lys Arg Arg Gln Arg Arg Arg Pro Pro Gln Ala Val
  1               5                  10                  15

Ser His Asn Leu Met Ile Thr Val Asp Asp Asp Gly Thr Met Arg Ile
             20                  25                  30

Gly Gly Gly Gly Arg Arg
         35
```

<210> SEQ ID NO 38
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: MOD_RES
<222> LOCATION: (15)
<223> OTHER INFORMATION: Linker residue beta-Alanine ; bAla
<220> FEATURE:
<221> NAME/KEY: DOMAIN
<222> LOCATION: (16)..(32)
<223> OTHER INFORMATION: NS3pro activation inhibitor segment,
NS3pro C-terminal domain binding segment,
segment of NS2B from the virus dengue 4
<220> FEATURE:
<221> NAME/KEY: DOMAIN
<222> LOCATION: (33)..(35)
<223> OTHER INFORMATION: linker segment
<220> FEATURE:
<221> NAME/KEY: DOMAIN
<222> LOCATION: (36)..(38)
<223> OTHER INFORMATION: segment bound to the active site of the viral
protease NS3pro
<220> FEATURE:
<223> OTHER INFORMATION: Carboxylic C-terminal end

<400> SEQUENCE: 38

```
Tyr Gly Arg Lys Lys Arg Arg Gln Arg Arg Arg Pro Pro Gln Ala Ser
  1               5                  10                  15

Ser Pro Ile Ile Glu Val Lys Gln Asp Glu Asp Gly Ser Phe Ser Ile
             20                  25                  30

Gly Gly Gly Gly Arg Arg
         35
```

<210> SEQ ID NO 39
<211> LENGTH: 30
<212> TYPE: PRT

-continued

<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro N-terminal domain binding segment,
segment of NS2B from the virus DV2

<400> SEQUENCE: 39

```
Tyr Gly Arg Lys Lys Arg Arg Gln Arg Arg Arg Pro Pro Gln Gly Gly
  1               5                  10                  15

Gly Asp Leu Glu Leu Glu Arg Ala Ala Asp Val Lys Trp Glu
             20                  25                  30
```

<210> SEQ ID NO 40
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro N-terminal domain binding segment,
segment of NS2B from the virus dengue 1
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 40

```
Tyr Gly Arg Lys Lys Arg Arg Gln Arg Arg Arg Pro Pro Gln Gly Gly
  1               5                  10                  15

Gly Asp Leu Ser Leu Glu Lys Ala Ala Glu Val Ser Trp Glu Gly Gly
             20                  25                  30

Lys Asp Glu Leu
         35
```

<210> SEQ ID NO 41
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:

```
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 41

Tyr Gly Arg Lys Lys Arg Arg Gln Arg Arg Arg Pro Pro Gln Gly Gly
  1               5                  10                  15

Gly Asp Leu Thr Val Glu Lys Ala Ala Asp Val Thr Trp Glu Gly Gly
             20                  25                  30

Lys Asp Glu Leu
         35


<210> SEQ ID NO 42
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the virus dengue 4
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 42

Tyr Gly Arg Lys Lys Arg Arg Gln Arg Arg Arg Pro Pro Gln Gly Gly
  1               5                  10                  15

Gly Asp Leu Ser Leu Glu Lys Ala Ala Asn Val Gln Trp Asp Gly Gly
             20                  25                  30

Lys Asp Glu Leu
         35
```

<210> SEQ ID NO 43
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the WNV
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 43

```
Tyr Gly Arg Lys Lys Arg Arg Gln Arg Arg Arg Pro Pro Gln Gly Gly
  1               5                  10                  15

Gly Asp Met Trp Ile Glu Arg Thr Ala Asp Ile Thr Trp Glu Gly Gly
             20                  25                  30

Lys Asp Glu Leu
         35
```

<210> SEQ ID NO 44
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the YFV
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 44

```
Tyr Gly Arg Lys Lys Arg Arg Gln Arg Arg Arg Pro Pro Gln Gly Gly
  1               5                  10                  15
```

Gly Gly Leu Glu Leu Lys Lys Leu Gly Glu Val Ser Trp Glu Gly Gly
20 25 30

Lys Asp Glu Leu
35

<210> SEQ ID NO 45
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment, NS3pro N-terminal domain binding segment, segment of NS2B from the Japanese Encephalitis virus
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 45

Tyr Gly Arg Lys Lys Arg Arg Gln Arg Arg Arg Pro Pro Gln Gly Gly
1 5 10 15

Gly Asp Met Trp Leu Glu Arg Ala Ala Asp Ile Ser Trp Glu Gly Gly
20 25 30

Lys Asp Glu Leu
35

<210> SEQ ID NO 46
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment, NS3pro N-terminal domain binding segment, segment of NS2B from the Thick-Borne Encephalitis virus
<220> FEATURE:
<221> NAME/KEY: DOMAIN
<222> LOCATION: (31)..(32)
<223> OTHER INFORMATION: linker segment
<220> FEATURE:

```
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 46

Tyr Gly Arg Lys Lys Arg Arg Gln Arg Arg Arg Pro Pro Gln Gly Gly
1               5                   10                  15

Gly Gln Leu Val Ala Glu Trp Ser Gly Cys Val Glu Trp His Gly Gly
            20                  25                  30

Lys Asp Glu Leu
        35


<210> SEQ ID NO 47
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro N-terminal domain binding segment,
      segment of NS2B from the virus DV2

<400> SEQUENCE: 47

Arg Arg Arg Arg Arg Arg Arg Arg Arg Arg Gly Gly Gly Asp Leu Glu
1               5                   10                  15

Leu Glu Arg Ala Ala Asp Val Lys Trp Glu
            20                  25


<210> SEQ ID NO 48
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro N-terminal domain binding segment,
      segment of NS2B from the virus dengue 1

<400> SEQUENCE: 48

Arg Arg Arg Arg Arg Arg Arg Arg Arg Arg Gly Gly Gly Asp Leu Ser
1               5                   10                  15

Leu Glu Lys Ala Ala Glu Val Ser Trp Glu
            20                  25
```

-continued

<210> SEQ ID NO 49
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro N-terminal domain binding segment,
segment of NS2B from the virus dengue 3

<400> SEQUENCE: 49

Arg Arg Arg Arg Arg Arg Arg Arg Arg Arg Gly Gly Gly Asp Leu Thr
1 5 10 15

Val Glu Lys Ala Ala Asp Val Thr Trp Glu
20 25

<210> SEQ ID NO 50
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro N-terminal domain binding segment,
segment of NS2B from the virus dengue 4

<400> SEQUENCE: 50

Arg Arg Arg Arg Arg Arg Arg Arg Arg Arg Gly Gly Gly Asp Leu Ser
1 5 10 15

Leu Glu Lys Ala Ala Asn Val Gln Trp Asp
20 25

<210> SEQ ID NO 51
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)

<223> OTHER INFORMATION: NS3pro activation inhibitor segment,
NS3pro N-terminal domain binding segment,
segment of NS2B from the WNV

<400> SEQUENCE: 51

Arg Arg Arg Arg Arg Arg Arg Arg Arg Arg Gly Gly Gly Asp Met Trp
1 5 10 15

Ile Glu Arg Thr Ala Asp Ile Thr Trp Glu
20 25

<210> SEQ ID NO 52
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro N-terminal domain binding segment,
segment of NS2B from the YFV

<400> SEQUENCE: 52

Arg Arg Arg Arg Arg Arg Arg Arg Arg Arg Gly Gly Gly Gly Leu Glu
1 5 10 15

Leu Lys Lys Leu Gly Glu Val Ser Trp Glu
20 25

<210> SEQ ID NO 53
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro N-terminal domain binding segment,
segment of NS2B from the Japanese Encephalitis
virus

<400> SEQUENCE: 53

Arg Arg Arg Arg Arg Arg Arg Arg Arg Arg Gly Gly Gly Asp Met Trp
1 5 10 15

Leu Glu Arg Ala Ala Asp Ile Ser Trp Glu
20 25

<210> SEQ ID NO 54
<211> LENGTH: 26
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro N-terminal domain binding segment,
segment of NS2B from the Thick-Borne
Encephalitis virus

<400> SEQUENCE: 54

```
Arg Arg Arg Arg Arg Arg Arg Arg Arg Arg Gly Gly Gly Gln Leu Val
  1               5                  10                  15

Ala Glu Trp Ser Gly Cys Val Glu Trp His
             20                  25
```

<210> SEQ ID NO 55
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro N-terminal domain binding segment,
segment of NS2B from the virus DV2
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 55

```
Tyr Gly Arg Lys Lys Arg Arg Gln Arg Arg Arg Pro Pro Gln Gly Gly
  1               5                  10                  15

Gly Asp Leu Glu Leu Glu Arg Ala Ala Asp Val Lys Trp Glu Gly Gly
             20                  25                  30

Lys Asp Glu Leu
         35
```

<210> SEQ ID NO 56
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:

```
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the virus dengue 1

<400> SEQUENCE: 56

Tyr Gly Arg Lys Lys Arg Arg Gln Arg Arg Arg Pro Pro Gln Gly Gly
  1               5                  10                  15

Gly Asp Leu Ser Leu Glu Lys Ala Ala Glu Val Ser Trp Glu
             20                  25                  30


<210> SEQ ID NO 57
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the virus dengue 3

<400> SEQUENCE: 57

Tyr Gly Arg Lys Lys Arg Arg Gln Arg Arg Arg Pro Pro Gln Gly Gly
  1               5                  10                  15

Gly Asp Leu Thr Val Glu Lys Ala Ala Asp Val Thr Trp Glu
             20                  25                  30


<210> SEQ ID NO 58
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the virus dengue 4

<400> SEQUENCE: 58

Tyr Gly Arg Lys Lys Arg Arg Gln Arg Arg Arg Pro Pro Gln Gly Gly
  1               5                  10                  15
```

```
Gly Asp Leu Ser Leu Glu Lys Ala Ala Asn Val Gln Trp Asp
            20                  25                  30


<210> SEQ ID NO 59
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the WNV

<400> SEQUENCE: 59

Tyr Gly Arg Lys Lys Arg Arg Gln Arg Arg Arg Pro Pro Gln Gly Gly
  1               5                  10                  15

Gly Asp Met Trp Ile Glu Arg Thr Ala Asp Ile Thr Trp Glu
            20                  25                  30


<210> SEQ ID NO 60
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
      NS3pro N-terminal domain binding segment,
      segment of NS2B from the YFV

<400> SEQUENCE: 60

Tyr Gly Arg Lys Lys Arg Arg Gln Arg Arg Arg Pro Pro Gln Gly Gly
  1               5                  10                  15

Gly Gly Leu Glu Leu Lys Lys Leu Gly Glu Val Ser Trp Glu
            20                  25                  30


<210> SEQ ID NO 61
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
```

<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro N-terminal domain binding segment,
segment of NS2B from the Japanese Encephalitis
virus

<400> SEQUENCE: 61

```
Tyr Gly Arg Lys Lys Arg Arg Gln Arg Arg Arg Pro Pro Gln Gly Gly
  1               5                  10                  15

Gly Asp Met Trp Leu Glu Arg Ala Ala Asp Ile Ser Trp Glu
             20                  25                  30
```

<210> SEQ ID NO 62
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: NS3pro activation inhibitor segment,
NS3pro N-terminal domain binding segment,
segment of NS2B from the Thick-Borne
Encephalitis virus

<400> SEQUENCE: 62

```
Tyr Gly Arg Lys Lys Arg Arg Gln Arg Arg Arg Pro Pro Gln Gly Gly
  1               5                  10                  15

Gly Gln Leu Val Ala Glu Trp Ser Gly Cys Val Glu Trp His
             20                  25                  30
```

<210> SEQ ID NO 63
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(30)
<223> OTHER INFORMATION: segment with amino acid composition identical
to the NS2B peptide involved in binding to the NS3pro
protease from the virus dengue 2
but with permutated sequence, Negative Control

<400> SEQUENCE: 63

```
Tyr Gly Arg Lys Lys Arg Arg Gln Arg Arg Arg Pro Pro Gln Gly Gly
1               5                  10                  15

Gly Leu Glu Gly Ser Asp Ile Ser Pro Ser Thr Ile Ser Ile
```

20 25 30

<210> SEQ ID NO 64
<211> LENGTH: 14
<212> TYPE: PRT
<213> ORGANISM: Artificial Sequence
<220> FEATURE:
<223> OTHER INFORMATION: Description of the Artificial Sequence: chimerical peptide
<220> FEATURE:
<223> OTHER INFORMATION: cell penetrating TAT peptide; Negative Control

<400> SEQUENCE: 64

Tyr Gly Arg Lys Lys Arg Arg Gln Arg Arg Arg Pro Pro Gln
1 5 10

<210> SEQ ID NO 65
<211> LENGTH: 29
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(29)
<223> OTHER INFORMATION: NS3pro activation inhibitor segment, NS3pro N-terminal domain binding segment, segment NS4A from HCV

<400> SEQUENCE: 65

Tyr Gly Arg Lys Lys Arg Arg Gln Arg Arg Arg Pro Pro Gln Gly Gly
1 5 10 15

Gly Thr Gly Ser Val Val Ile Val Gly Arg Ile Ile Leu
20 25

<210> SEQ ID NO 66
<211> LENGTH: 29
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(14)
<223> OTHER INFORMATION: cell penetrating TAT peptide
<220> FEATURE:
<221> NAME/KEY: DOMAIN
<222> LOCATION: (15)..(17)
<223> OTHER INFORMATION: linker segment
<220> FEATURE:
<221> NAME/KEY: DOMAIN
<222> LOCATION: (18)..(29)
<223> OTHER INFORMATION: NS3pro activation inhibitor segment, NS3pro N-terminal domain binding segment, segment NS4A from HCV, mutation of R28 by Q

<400> SEQUENCE: 66

Tyr Gly Arg Lys Lys Arg Arg Gln Arg Arg Arg Pro Pro Gln Gly Gly
1 5 10 15

Gly Thr Gly Ser Val Val Ile Val Gly Gln Ile Ile Leu
20 25

<210> SEQ ID NO 67
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro C-terminal domain binding segment, segment of NS2B from the virus DV2

<400> SEQUENCE: 67

```
Cys Ser Asn Ile Val Ile Gly Ile Gly Asp Lys Ala Leu Lys Ile Asn
  1               5                  10                  15

Trp Cys Ala Ser Ser Pro Ile Leu Ser Ile Thr Ile Ser Glu Asp Gly
             20                  25                  30
```

<210> SEQ ID NO 68
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro C-terminal domain binding segment, segment of NS2B from the YFV

<400> SEQUENCE: 68

```
Cys Ser Asn Ile Val Ile Gly Ile Gly Asp Lys Ala Leu Lys Ile Asn
  1               5                  10                  15

Trp Cys Ala Ser Ser Ala Arg Tyr Asp Val Ala Leu Ser Glu Gln Gly
             20                  25                  30
```

<210> SEQ ID NO 69
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES

```
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
      NS3pro C-terminal domain binding segment,
      segment of NS2B from the Japanese Encephalitis
      virus

<400> SEQUENCE: 69

Cys Ser Asn Ile Val Ile Gly Ile Gly Asp Lys Ala Leu Lys Ile Asn
  1               5                  10                  15

Trp Cys Ala Ser Ser Arg Arg Leu Asp Val Lys Leu Asp Asp Asp Gly
             20                  25                  30


<210> SEQ ID NO 70
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(18)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
      NS3pro C-terminal domain binding segment,
      segment of NS2B from the Thick-Borne
      Encephalitis virus

<400> SEQUENCE: 70

Cys Ser Asn Ile Val Ile Gly Ile Gly Asp Lys Ala Leu Lys Ile Asn
  1               5                  10                  15

Trp Cys Ala Gly Glu Val Ser Leu Arg Val Arg Gln Asp Ala Met Gly
             20                  25                  30


<210> SEQ ID NO 71
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(18)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
      NS3pro C-terminal domain binding segment,
      segment of NS2B from the WNV

<400> SEQUENCE: 71

Cys Ser Asn Ile Val Ile Gly Ile Gly Asp Lys Ala Leu Lys Ile Asn
  1               5                  10                  15
```

Trp Cys Ala Ser Ser Glu Arg Val Asp Val Arg Leu Asp Asp Asp Gly
20 25 30

<210> SEQ ID NO 72
<211> LENGTH: 31
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(31)
<223> OTHER INFORMATION: NS3pro activation inhibitor segment, NS3pro N-terminal domain binding segment, segment NS4A from HCV

<400> SEQUENCE: 72

Cys Ser Asn Ile Val Ile Gly Ile Gly Asp Lys Ala Leu Lys Ile Asn
1 5 10 15

Trp Cys Ala Thr Gly Ser Val Val Ile Val Gly Arg Ile Ile Leu
20 25 30

<210> SEQ ID NO 73
<211> LENGTH: 31
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(31)
<223> OTHER INFORMATION: NS3pro activation inhibitor segment, NS3pro N-terminal domain binding segment, segment NS4A from HCV, mutation of R28 by Q

<400> SEQUENCE: 73

Cys Ser Asn Ile Val Ile Gly Ile Gly Asp Lys Ala Leu Lys Ile Asn
1 5 10 15

Trp Cys Ala Thr Gly Ser Val Val Ile Val Gly Gln Ile Ile Leu
20 25 30

<210> SEQ ID NO 74
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the virus dengue 1

<400> SEQUENCE: 74

```
Cys Ser Asn Ile Val Ile Gly Ile Gly Asp Lys Ala Leu Lys Ile Asn
1               5                   10                  15

Trp Cys Ala Ala Ser His Asn Ile Leu Val Glu Val Gln Asp Asp Gly
            20                  25                  30
```

<210> SEQ ID NO 75
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the virus dengue 3

<400> SEQUENCE: 75

```
Cys Ser Asn Ile Val Ile Gly Ile Gly Asp Lys Ala Leu Lys Ile Asn
1               5                   10                  15

Trp Cys Ala Val Ser His Asn Leu Met Ile Thr Val Asp Asp Asp Gly
            20                  25                  30
```

<210> SEQ ID NO 76
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the virus dengue 4

<400> SEQUENCE: 76

```
Cys Ser Asn Ile Val Ile Gly Ile Gly Asp Lys Ala Leu Lys Ile Asn
1               5                   10                  15
```

Trp Cys Ala Ser Ser Pro Ile Ile Glu Val Lys Gln Asp Glu Asp Gly
20 25 30

<210> SEQ ID NO 77
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the virus DV2

<400> SEQUENCE: 77

Cys Ser Asn Ile Val Ile Gly Ile Gly Asp Lys Ala Leu Lys Ile Asn
1 5 10 15

Trp Cys Ala Asp Leu Glu Leu Glu Arg Ala Ala Asp Val Lys Trp Glu
20 25 30

<210> SEQ ID NO 78
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the virus dengue 1

<400> SEQUENCE: 78

Cys Ser Asn Ile Val Ile Gly Ile Gly Asp Lys Ala Leu Lys Ile Asn
1 5 10 15

Trp Cys Ala Asp Leu Ser Leu Glu Lys Ala Ala Glu Val Ser Trp Glu
20 25 30

<210> SEQ ID NO 79
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the virus dengue 3

<400> SEQUENCE: 79

Cys Ser Asn Ile Val Ile Gly Ile Gly Asp Lys Ala Leu Lys Ile Asn
1 5 10 15

Trp Cys Ala Asp Leu Thr Val Glu Lys Ala Ala Asp Val Thr Trp Glu
20 25 30

<210> SEQ ID NO 80
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the virus dengue 4

<400> SEQUENCE: 80

Cys Ser Asn Ile Val Ile Gly Ile Gly Asp Lys Ala Leu Lys Ile Asn
1 5 10 15

Trp Cys Ala Asp Leu Ser Leu Glu Lys Ala Ala Asn Val Gln Trp Asp
20 25 30

<210> SEQ ID NO 81
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the WNV

<400> SEQUENCE: 81

Cys Ser Asn Ile Val Ile Gly Ile Gly Asp Lys Ala Leu Lys Ile Asn
1 5 10 15

Trp Cys Ala Asp Met Trp Ile Glu Arg Thr Ala Asp Ile Thr Trp Glu
20 25 30

<210> SEQ ID NO 82
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the YFV

<400> SEQUENCE: 82

Cys Ser Asn Ile Val Ile Gly Ile Gly Asp Lys Ala Leu Lys Ile Asn
1 5 10 15

Trp Cys Ala Gly Leu Glu Leu Lys Lys Leu Gly Glu Val Ser Trp Glu
20 25 30

<210> SEQ ID NO 83
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the Japanese Encephalitis virus

<400> SEQUENCE: 83

Cys Ser Asn Ile Val Ile Gly Ile Gly Asp Lys Ala Leu Lys Ile Asn
1 5 10 15

Trp Cys Ala Asp Met Trp Leu Glu Arg Ala Ala Asp Ile Ser Trp Glu
20 25 30

<210> SEQ ID NO 84
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)

<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
      NS3pro N-terminal domain binding segment,
      segment of NS2B from the Thick-Borne
      Encephalitis virus

<400> SEQUENCE: 84

```
Cys Ser Asn Ile Val Ile Gly Ile Gly Asp Lys Ala Leu Lys Ile Asn
  1               5                  10                  15

Trp Cys Ala Gln Leu Val Ala Glu Trp Ser Gly Cys Val Glu Trp His
             20                  25                  30
```

<210> SEQ ID NO 85
<211> LENGTH: 42
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(18)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment,
      NS3pro C-terminal domain binding segment,
      segment of NS2B from the virus DV2
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
      protease NS3pro
<220> FEATURE:
<223> OTHER INFORMATION: Carboxylic C-terminal end

<400> SEQUENCE: 85

```
Cys Ser Asn Ile Val Ile Gly Ile Gly Asp Lys Ala Leu Lys Ile Asn
  1               5                  10                  15

Trp Cys Ala Ser Ser Pro Ile Leu Ser Ile Thr Ile Ser Glu Asp Gly
             20                  25                  30

Ser Met Ser Ile Gly Gly Gly Gly Arg Arg
         35                  40
```

<210> SEQ ID NO 86
<211> LENGTH: 42
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(18)
<223> OTHER INFORMATION: cell penetrating peptide based on the FG

```
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment,
      NS3pro C-terminal domain binding segment,
      segment of NS2B from the YFV
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
      protease NS3pro
<220> FEATURE:
<223> OTHER INFORMATION: Carboxylic C-terminal end

<400> SEQUENCE: 86

Cys Ser Asn Ile Val Ile Gly Ile Gly Asp Lys Ala Leu Lys Ile Asn
  1               5                  10                  15

Trp Cys Ala Ser Ser Ala Arg Tyr Asp Val Ala Leu Ser Glu Gln Gly
             20                  25                  30

Glu Phe Lys Leu Gly Gly Gly Gly Arg Arg
         35                  40


<210> SEQ ID NO 87
<211> LENGTH: 42
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(18)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment,
      NS3pro C-terminal domain binding segment,
      segment of NS2B from the Japanese Encephalitis
      virus
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
      protease NS3pro
<220> FEATURE:
<223> OTHER INFORMATION: Carboxylic C-terminal end

<400> SEQUENCE: 87

Cys Ser Asn Ile Val Ile Gly Ile Gly Asp Lys Ala Leu Lys Ile Asn
  1               5                  10                  15

Trp Cys Ala Ser Ser Arg Arg Leu Asp Val Lys Leu Asp Asp Asp Gly
             20                  25                  30

Asp Phe His Leu Gly Gly Gly Gly Arg Arg
         35                  40
```

<210> SEQ ID NO 88
<211> LENGTH: 42
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment,
NS3pro C-terminal domain binding segment,
segment of NS2B from the Thick-Borne
Encephalitis virus
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
protease NS3pro
<220> FEATURE:
<223> OTHER INFORMATION: Carboxylic C-terminal end

<400> SEQUENCE: 88

Cys Ser Asn Ile Val Ile Gly Ile Gly Asp Lys Ala Leu Lys Ile Asn
1 5 10 15

Trp Cys Ala Gly Glu Val Ser Leu Arg Val Arg Gln Asp Ala Met Gly
20 25 30

Asn Leu His Leu Gly Gly Gly Gly Arg Arg
35 40

<210> SEQ ID NO 89
<211> LENGTH: 42
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment,
NS3pro C-terminal domain binding segment,
segment of NS2B from the WNV
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
protease NS3pro <220> FEATURE:
<223> OTHER INFORMATION: Carboxylic C-terminal end

<400> SEQUENCE: 89

Cys Ser Asn Ile Val Ile Gly Ile Gly Asp Lys Ala Leu Lys Ile Asn
1 5 10 15

Trp Cys Ala Ser Ser Glu Arg Val Asp Val Arg Leu Asp Asp Asp Gly
20 25 30

Asn Phe Gln Leu Gly Gly Gly Gly Arg Arg
35 40

<210> SEQ ID NO 90
<211> LENGTH: 42
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment, NS3pro C-terminal domain binding segment, segment of NS2B from the virus dengue 1
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral protease NS3pro
<220> FEATURE:
<223> OTHER INFORMATION: Carboxylic C-terminal end

<400> SEQUENCE: 90

Cys Ser Asn Ile Val Ile Gly Ile Gly Asp Lys Ala Leu Lys Ile Asn
1 5 10 15

Trp Cys Ala Ala Ser His Asn Ile Leu Val Glu Val Gln Asp Asp Gly
20 25 30

Thr Met Lys Ile Gly Gly Gly Gly Arg Arg
35 40

<210> SEQ ID NO 91
<211> LENGTH: 42
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)

<223> OTHER INFORMATION: NS3pro activation inhibitor segment,
NS3pro C-terminal domain binding segment,
segment of NS2B from the virus dengue 3
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
protease NS3pro
<220> FEATURE:
<223> OTHER INFORMATION: Carboxylic C-terminal end

<400> SEQUENCE: 91

Cys Ser Asn Ile Val Ile Gly Ile Gly Asp Lys Ala Leu Lys Ile Asn
1 5 10 15

Trp Cys Ala Val Ser His Asn Leu Met Ile Thr Val Asp Asp Asp Gly
20 25 30

Thr Met Arg Ile Gly Gly Gly Gly Arg Arg
35 40

<210> SEQ ID NO 92
<211> LENGTH: 42
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(36)
<223> OTHER INFORMATION: NS3pro activation inhibitor segment,
NS3pro C-terminal domain binding segment,
segment of NS2B from the virus dengue 4
<220> FEATURE:
<221> NAME/KEY: DOMAIN
<222> LOCATION: (37)..(39)
<223> OTHER INFORMATION: linker segment
<220> FEATURE:
<221> NAME/KEY: DOMAIN
<222> LOCATION: (40)..(42)
<223> OTHER INFORMATION: segment bound to the active site of the viral
protease NS3pro
<220> FEATURE:
<223> OTHER INFORMATION: Carboxylic C-terminal end

<400> SEQUENCE: 92

Cys Ser Asn Ile Val Ile Gly Ile Gly Asp Lys Ala Leu Lys Ile Asn
1 5 10 15

Trp Cys Ala Ser Ser Pro Ile Ile Glu Val Lys Gln Asp Glu Asp Gly
20 25 30

Ser Phe Ser Ile Gly Gly Gly Gly Arg Arg
35 40

<210> SEQ ID NO 93
<211> LENGTH: 38
<212> TYPE: PRT
<213> ORGANISM: Artificial Sequence
<220> FEATURE:
<223> OTHER INFORMATION: Description of the Artificial Sequence:
chimerical peptide

```
<220> FEATURE:
<221> NAME/KEY: DOMAIN
<222> LOCATION: (1)..(18)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
      NS3pro C-terminal domain binding segment,
      segment of NS2B from the virus DV2
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 93

Cys Ser Asn Ile Val Ile Gly Ile Gly Asp Lys Ala Leu Lys Ile Asn
  1               5                  10                  15

Trp Cys Ala Ser Ser Pro Ile Leu Ser Ile Thr Ile Ser Glu Asp Gly
             20                  25                  30

Gly Gly Lys Asp Glu Leu
         35


<210> SEQ ID NO 94
<211> LENGTH: 38
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(18)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
      NS3pro C-terminal domain binding segment,
      segment of NS2B from the YFV
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 94

Cys Ser Asn Ile Val Ile Gly Ile Gly Asp Lys Ala Leu Lys Ile Asn
  1               5                  10                  15

Trp Cys Ala Ser Ser Ala Arg Tyr Asp Val Ala Leu Ser Glu Gln Gly
             20                  25                  30

Gly Gly Lys Asp Glu Leu
```

35

<210> SEQ ID NO 95
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 95

Cys Ser Asn Ile Val Ile Gly Ile Gly Asp Lys Ala Leu Lys Ile Asn
1 5 10 15

Trp Cys Ala Ser Ser Arg Arg Leu Asp Val Lys Leu Asp Asp Asp Gly
20 25 30

Gly Gly Lys Asp Glu Leu
35

<210> SEQ ID NO 96
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the Thick-Borne
Encephalitis virus
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 96

Cys Ser Asn Ile Val Ile Gly Ile Gly Asp Lys Ala Leu Lys Ile Asn
1 5 10 15

Trp Cys Ala Gly Glu Val Ser Leu Arg Val Arg Gln Asp Ala Met Gly
20 25 30

Gly Gly Lys Asp Glu Leu
35

<210> SEQ ID NO 97
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the WNV
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 97

Cys Ser Asn Ile Val Ile Gly Ile Gly Asp Lys Ala Leu Lys Ile Asn
1 5 10 15

Trp Cys Ala Ser Ser Glu Arg Val Asp Val Arg Leu Asp Asp Asp Gly
20 25 30

Gly Gly Lys Asp Glu Leu
35

<210> SEQ ID NO 98
<211> LENGTH: 37
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(31)
<223> OTHER INFORMATION: NS3pro activation inhibitor segment, NS3pro N-terminal domain binding segment,
segment NS4A from HCV
<220> FEATURE:
<221> NAME/KEY: DOMAIN
<222> LOCATION: (32)..(33)
<223> OTHER INFORMATION: linker segment
<220> FEATURE:
<221> NAME/KEY: SIGNAL
<222> LOCATION: (34)..(37)
<223> OTHER INFORMATION: ER Retention signal KDEL
<220> FEATURE:
<223> OTHER INFORMATION: Carboxylic C-terminal end

<400> SEQUENCE: 98

```
Cys Ser Asn Ile Val Ile Gly Ile Gly Asp Lys Ala Leu Lys Ile Asn
  1               5                  10                  15

Trp Cys Ala Thr Gly Ser Val Val Ile Val Gly Arg Ile Ile Leu Gly
             20                  25                  30

Gly Lys Asp Glu Leu
         35
```

<210> SEQ ID NO 99
<211> LENGTH: 37
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(31)
<223> OTHER INFORMATION: NS3pro activation inhibitor segment,
NS3pro N-terminal domain binding segment,
segment NS4A from HCV,
mutation of R28 by Q
<220> FEATURE:
<221> NAME/KEY: DOMAIN
<222> LOCATION: (32)..(33)
<223> OTHER INFORMATION: linker segment
<220> FEATURE:
<221> NAME/KEY: SIGNAL
<222> LOCATION: (34)..(37)
<223> OTHER INFORMATION: ER Retention signal KDEL
<220> FEATURE:
<223> OTHER INFORMATION: Carboxylic C-terminal end

<400> SEQUENCE: 99

```
Cys Ser Asn Ile Val Ile Gly Ile Gly Asp Lys Ala Leu Lys Ile Asn
  1               5                  10                  15

Trp Cys Ala Thr Gly Ser Val Val Ile Val Gly Gln Ile Ile Leu Gly
             20                  25                  30

Gly Lys Asp Glu Leu
         35
```

<210> SEQ ID NO 100
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro C-terminal domain binding segment, segment of NS2B from the virus dengue 1
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 100

```
Cys Ser Asn Ile Val Ile Gly Ile Gly Asp Lys Ala Leu Lys Ile Asn
  1               5                  10                  15

Trp Cys Ala Ala Ser His Asn Ile Leu Val Glu Val Gln Asp Asp Gly
             20                  25                  30

Gly Gly Lys Asp Glu Leu
         35
```

<210> SEQ ID NO 101
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro C-terminal domain binding segment, segment of NS2B from the virus dengue 3
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end

<400> SEQUENCE: 101

```
Cys Ser Asn Ile Val Ile Gly Ile Gly Asp Lys Ala Leu Lys Ile Asn
  1               5                  10                  15

Trp Cys Ala Val Ser His Asn Leu Met Ile Thr Val Asp Asp Asp Gly
             20                  25                  30

Gly Gly Lys Asp Glu Leu
         35
```

<210> SEQ ID NO 102
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro C-terminal domain binding segment,
segment of NS2B from the virus dengue 4
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 102

```
Cys Ser Asn Ile Val Ile Gly Ile Gly Asp Lys Ala Leu Lys Ile Asn
  1               5                  10                  15

Trp Cys Ala Ser Ser Pro Ile Ile Glu Val Lys Gln Asp Glu Asp Gly
            20                  25                  30

Gly Gly Lys Asp Glu Leu
        35
```

<210> SEQ ID NO 103
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro N-terminal domain binding segment,
segment of NS2B from the virus DV2
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:

<223> OTHER INFORMATION: Carboxylic C-terminal end
<220> FEATURE:
<221> NAME/KEY: DISULFID
<222> LOCATION: (1)..(18)

<400> SEQUENCE: 103

```
Cys Ser Asn Ile Val Ile Gly Ile Gly Asp Lys Ala Leu Lys Ile Asn
  1               5                  10                  15

Trp Cys Ala Asp Leu Glu Leu Glu Arg Ala Ala Asp Val Lys Trp Glu
             20                  25                  30

Gly Gly Lys Asp Glu Leu
         35
```

<210> SEQ ID NO 104
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the virus dengue 1
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 104

```
Cys Ser Asn Ile Val Ile Gly Ile Gly Asp Lys Ala Leu Lys Ile Asn
  1               5                  10                  15

Trp Cys Ala Asp Leu Ser Leu Glu Lys Ala Ala Glu Val Ser Trp Glu
             20                  25                  30

Gly Gly Lys Asp Glu Leu
         35
```

<210> SEQ ID NO 105
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)

<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro N-terminal domain binding segment,
segment of NS2B from the virus dengue 3
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 105

```
Cys Ser Asn Ile Val Ile Gly Ile Gly Asp Lys Ala Leu Lys Ile Asn
1               5                   10                  15

Trp Cys Ala Asp Leu Thr Val Glu Lys Ala Ala Asp Val Thr Trp Glu
            20                  25                  30

Gly Gly Lys Asp Glu Leu
        35
```

<210> SEQ ID NO 106
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro N-terminal domain binding segment,
segment of NS2B from the virus dengue 4
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 106

```
Cys Ser Asn Ile Val Ile Gly Ile Gly Asp Lys Ala Leu Lys Ile Asn
1               5                   10                  15

Trp Cys Ala Asp Leu Ser Leu Glu Lys Ala Ala Asn Val Gln Trp Asp
            20                  25                  30

Gly Gly Lys Asp Glu Leu
        35
```

<210> SEQ ID NO 107
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro N-terminal domain binding segment,
segment of NS2B from the WNV
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 107

```
Cys Ser Asn Ile Val Ile Gly Ile Gly Asp Lys Ala Leu Lys Ile Asn
  1               5                  10                  15

Trp Cys Ala Asp Met Trp Ile Glu Arg Thr Ala Asp Ile Thr Trp Glu
             20                  25                  30

Gly Gly Lys Asp Glu Leu
         35
```

<210> SEQ ID NO 108
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(18)
<223> OTHER INFORMATION: cell penetrating peptide based on the FG
hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro N-terminal domain binding segment,
segment of NS2B from the YFV
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:

-continued

<223> OTHER INFORMATION: Carboxylic C-terminal end
<220> FEATURE:
<221> NAME/KEY: DISULFID
<222> LOCATION: (1)..(18)

<400> SEQUENCE: 108

Cys Ser Asn Ile Val Ile Gly Ile Gly Asp Lys Ala Leu Lys Ile Asn
1 5 10 15

Trp Cys Ala Gly Leu Glu Leu Lys Lys Leu Gly Glu Val Ser Trp Glu
20 25 30

Gly Gly Lys Asp Glu Leu
35

<210> SEQ ID NO 109
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment, NS3pro N-terminal domain binding segment, segment of NS2B from the Japanese Encephalitis virus
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 109

Cys Ser Asn Ile Val Ile Gly Ile Gly Asp Lys Ala Leu Lys Ile Asn
1 5 10 15

Trp Cys Ala Asp Met Trp Leu Glu Arg Ala Ala Asp Ile Ser Trp Glu
20 25 30

Gly Gly Lys Asp Glu Leu
35

<210> SEQ ID NO 110
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(18)
<223> OTHER INFORMATION: cell penetrating peptide based on the FG hairpin of domain III from the envelope protein of DV3
<220> FEATURE:
<221> NAME/KEY: MOD_RES
<222> LOCATION: (19)
<223> OTHER INFORMATION: Linker residue beta-Alanine ; bAla
<220> FEATURE:
<221> NAME/KEY: DOMAIN
<222> LOCATION: (20)..(32)
<223> OTHER INFORMATION: NS3pro activation inhibitor segment,
NS3pro N-terminal domain binding segment,
segment of NS2B from the Thick-Borne
Encephalitis virus
<220> FEATURE:
<221> NAME/KEY: DOMAIN
<222> LOCATION: (33)..(34)
<223> OTHER INFORMATION: linker segment
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (1)..(18)

<400> SEQUENCE: 110

```
Cys Ser Asn Ile Val Ile Gly Ile Gly Asp Lys Ala Leu Lys Ile Asn
  1               5                  10                  15

Trp Cys Ala Gln Leu Val Ala Glu Trp Ser Gly Cys Val Glu Trp His
             20                  25                  30

Gly Gly Lys Asp Glu Leu
         35
```

<210> SEQ ID NO 111
<211> LENGTH: 40
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the virus DV2
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: DISULFID
<222> LOCATION: (2)..(19)

<400> SEQUENCE: 111

Ala Cys Ser Asn Ile Val Ile Gly Ile Gly Asp Lys Ala Leu Lys Ile
1 5 10 15

Asn Trp Cys Ala Ser Ser Pro Ile Leu Ser Ile Thr Ile Ser Glu Asp
20 25 30

Gly Ala Leu Arg Arg Arg Arg Leu
35 40

<210> SEQ ID NO 112
<211> LENGTH: 40
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE ; MYRISTATE bound to the N terminal end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the YFV
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: DISULFID
<222> LOCATION: (2)..(19)

<400> SEQUENCE: 112

Ala Cys Ser Asn Ile Val Ile Gly Ile Gly Asp Lys Ala Leu Lys Ile
1 5 10 15

Asn Trp Cys Ala Ser Ser Ala Arg Tyr Asp Val Ala Leu Ser Glu Gln
20 25 30

Gly Ala Leu Arg Arg Arg Arg Leu
35 40

<210> SEQ ID NO 113
<211> LENGTH: 40
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE ; MYRISTATE bound to the N terminal end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: DISULFID
<222> LOCATION: (2)..(19)

<400> SEQUENCE: 113

```
Ala Cys Ser Asn Ile Val Ile Gly Ile Gly Asp Lys Ala Leu Lys Ile
  1               5                  10                  15

Asn Trp Cys Ala Ser Ser Arg Arg Leu Asp Val Lys Leu Asp Asp Asp
             20                  25                  30

Gly Ala Leu Arg Arg Arg Arg Leu
         35                  40
```

<210> SEQ ID NO 114
<211> LENGTH: 40
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the Thick-Borne
Encephalitis virus

```
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 114

Ala Cys Ser Asn Ile Val Ile Gly Ile Gly Asp Lys Ala Leu Lys Ile
  1               5                  10                  15

Asn Trp Cys Ala Gly Glu Val Ser Leu Arg Val Arg Gln Asp Ala Met
             20                  25                  30

Gly Ala Leu Arg Arg Arg Arg Leu
         35                  40


<210> SEQ ID NO 115
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE  ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the WNV
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 115

Ala Cys Ser Asn Ile Val Ile Gly Ile Gly Asp Lys Ala Leu Lys Ile
  1               5                  10                  15

Asn Trp Cys Ala Ser Ser Glu Arg Val Asp Val Arg Leu Asp Asp Asp
             20                  25                  30

Gly Ala Leu Arg Arg Arg Arg Leu
         35                  40
```

```
<210> SEQ ID NO 116
<211> LENGTH: 39
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE  ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(32)
<223> OTHER INFORMATION: NS3pro activation inhibitor segment,
      NS3pro N-terminal domain binding segment,
      segment NS4A from HCV
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 116

Ala Cys Ser Asn Ile Val Ile Gly Ile Gly Asp Lys Ala Leu Lys Ile
  1               5                  10                  15

Asn Trp Cys Ala Thr Gly Ser Val Val Ile Val Gly Arg Ile Ile Leu
             20                  25                  30

Ala Leu Arg Arg Arg Arg Leu
         35


<210> SEQ ID NO 117
<211> LENGTH: 39
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
```

hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(32)
<223> OTHER INFORMATION: NS3pro activation inhibitor segment,
NS3pro N-terminal domain binding segment,
segment NS4A from HCV,
mutation of R28 by Q
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (2)..(19)

<400> SEQUENCE: 117

```
Ala Cys Ser Asn Ile Val Ile Gly Ile Gly Asp Lys Ala Leu Lys Ile
  1               5                  10                  15

Asn Trp Cys Ala Thr Gly Ser Val Val Ile Val Gly Gln Ile Ile Leu
             20                  25                  30

Ala Leu Arg Arg Arg Arg Leu
         35
```

<210> SEQ ID NO 118
<211> LENGTH: 40
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the virus dengue 1
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: DISULFID

```
<222> LOCATION: (2)..(19)

<400> SEQUENCE: 118

Ala Cys Ser Asn Ile Val Ile Gly Ile Gly Asp Lys Ala Leu Lys Ile
  1               5                  10                  15

Asn Trp Cys Ala Ala Ser His Asn Ile Leu Val Glu Val Gln Asp Asp
             20                  25                  30

Gly Ala Leu Arg Arg Arg Arg Leu
         35                  40


<210> SEQ ID NO 119
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the virus dengue 3
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 119

Ala Cys Ser Asn Ile Val Ile Gly Ile Gly Asp Lys Ala Leu Lys Ile
  1               5                  10                  15

Asn Trp Cys Ala Val Ser His Asn Leu Met Ile Thr Val Asp Asp Asp
             20                  25                  30

Gly Ala Leu Arg Arg Arg Arg Leu
         35                  40


<210> SEQ ID NO 120
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
```

```
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 120

Ala Cys Ser Asn Ile Val Ile Gly Ile Gly Asp Lys Ala Leu Lys Ile
  1               5                  10                  15

Asn Trp Cys Ala Ser Ser Pro Ile Ile Glu Val Lys Gln Asp Glu Asp
             20                  25                  30

Gly Ala Leu Arg Arg Arg Arg Leu
         35                  40


<210> SEQ ID NO 121
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the virus DV2
```

<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: DISULFID
<222> LOCATION: (2)..(19)

<400> SEQUENCE: 121

```
Ala Cys Ser Asn Ile Val Ile Gly Ile Gly Asp Lys Ala Leu Lys Ile
  1               5                  10                  15

Asn Trp Cys Ala Asp Leu Glu Leu Glu Arg Ala Ala Asp Val Lys Trp
             20                  25                  30

Glu Ala Leu Arg Arg Arg Arg Leu
         35                  40
```

<210> SEQ ID NO 122
<211> LENGTH: 40
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro N-terminal domain binding segment,
segment of NS2B from the virus dengue 1
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: DISULFID
<222> LOCATION: (2)..(19)

<400> SEQUENCE: 122

```
Ala Cys Ser Asn Ile Val Ile Gly Ile Gly Asp Lys Ala Leu Lys Ile
  1               5                  10                  15

Asn Trp Cys Ala Asp Leu Ser Leu Glu Lys Ala Ala Glu Val Ser Trp
             20                  25                  30

Glu Ala Leu Arg Arg Arg Arg Leu
         35                  40
```

```
<210> SEQ ID NO 123
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 123

Ala Cys Ser Asn Ile Val Ile Gly Ile Gly Asp Lys Ala Leu Lys Ile
  1               5                  10                  15

Asn Trp Cys Ala Asp Leu Thr Val Glu Lys Ala Ala Asp Val Thr Trp
             20                  25                  30

Glu Ala Leu Arg Arg Arg Arg Leu
         35                  40


<210> SEQ ID NO 124
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
```

```
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the virus dengue 4
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 124

Ala Cys Ser Asn Ile Val Ile Gly Ile Gly Asp Lys Ala Leu Lys Ile
  1               5                  10                  15

Asn Trp Cys Ala Asp Leu Ser Leu Glu Lys Ala Ala Asn Val Gln Trp
             20                  25                  30

Asp Ala Leu Arg Arg Arg Arg Leu
         35                  40


<210> SEQ ID NO 125
<211> LENGTH: 40
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the WNV
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)
```

<400> SEQUENCE: 125

Ala Cys Ser Asn Ile Val Ile Gly Ile Gly Asp Lys Ala Leu Lys Ile
1 5 10 15

Asn Trp Cys Ala Asp Met Trp Ile Glu Arg Thr Ala Asp Ile Thr Trp
20 25 30

Glu Ala Leu Arg Arg Arg Arg Leu
35 40

<210> SEQ ID NO 126
<211> LENGTH: 40
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE ; MYRISTATE bound to the N terminal end of the chimerical peptide PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment, NS3pro N-terminal domain binding segment, segment of NS2B from the YFV
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal ER is the Endoplasmic Reticulum
<220> FEATURE:
<221> NAME/KEY: DISULFID
<222> LOCATION: (2)..(19)

<400> SEQUENCE: 126

Ala Cys Ser Asn Ile Val Ile Gly Ile Gly Asp Lys Ala Leu Lys Ile
1 5 10 15

Asn Trp Cys Ala Gly Leu Glu Leu Lys Lys Leu Gly Glu Val Ser Trp
20 25 30

Glu Ala Leu Arg Arg Arg Arg Leu
35 40

<210> SEQ ID NO 127
<211> LENGTH: 40
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)

<223> OTHER INFORMATION: MYRISTATE ; MYRISTATE bound to the N terminal end of the chimerical peptide PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment, NS3pro N-terminal domain binding segment, segment of NS2B from the Japanese Encephalitis virus
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal ER is the Endoplasmic Reticulum
<220> FEATURE:
<221> NAME/KEY: DISULFID
<222> LOCATION: (2)..(19)

<400> SEQUENCE: 127

```
Ala Cys Ser Asn Ile Val Ile Gly Ile Gly Asp Lys Ala Leu Lys Ile
  1               5                  10                  15

Asn Trp Cys Ala Asp Met Trp Leu Glu Arg Ala Ala Asp Ile Ser Trp
             20                  25                  30

Glu Ala Leu Arg Arg Arg Arg Leu
         35                  40
```

<210> SEQ ID NO 128
<211> LENGTH: 40
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE; MYRISTATE bound to the N terminal end of the chimerical peptide PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment, NS3pro N-terminal domain binding segment, segment of NS2B from the Thick-Borne

```
      Encephalitis virus
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: DISULFID
<222> LOCATION: (2)..(19)

<400> SEQUENCE: 128

Ala Cys Ser Asn Ile Val Ile Gly Ile Gly Asp Lys Ala Leu Lys Ile
  1               5                  10                  15

Asn Trp Cys Ala Gln Leu Val Ala Glu Trp Ser Gly Cys Val Glu Trp
             20                  25                  30

His Ala Leu Arg Arg Arg Arg Leu
         35                  40


<210> SEQ ID NO 129
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE  ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the virus DV2
<220> FEATURE:
<221> NAME/KEY: DISULFID
<222> LOCATION: (2)..(19)

<400> SEQUENCE: 129

Ala Cys Ser Asn Ile Val Ile Gly Ile Gly Asp Lys Ala Leu Lys Ile
  1               5                  10                  15

Asn Trp Cys Ala Ser Ser Pro Ile Leu Ser Ile Thr Ile Ser Glu Asp
             20                  25                  30

Gly


<210> SEQ ID NO 130
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
```

```
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the YFV
<220> FEATURE:
<221> NAME/KEY: DISULFID
<222> LOCATION: (2)..(19)

<400> SEQUENCE: 130

Ala Cys Ser Asn Ile Val Ile Gly Ile Gly Asp Lys Ala Leu Lys Ile
  1               5                  10                  15

Asn Trp Cys Ala Ser Ser Ala Arg Tyr Asp Val Ala Leu Ser Glu Gln
             20                  25                  30

Gly


<210> SEQ ID NO 131
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the Japanese Encephalitis
      virus
<220> FEATURE:
<221> NAME/KEY: DISULFID
<222> LOCATION: (2)..(19)

<400> SEQUENCE: 131

Ala Cys Ser Asn Ile Val Ile Gly Ile Gly Asp Lys Ala Leu Lys Ile
```

-continued

```
  1               5                  10                  15

Asn Trp Cys Ala Ser Ser Arg Arg Leu Asp Val Lys Leu Asp Asp Asp
             20                  25                  30

Gly


<210> SEQ ID NO 132
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: DISULFID
<222> LOCATION: (2)..(19)

<400> SEQUENCE: 132

Ala Cys Ser Asn Ile Val Ile Gly Ile Gly Asp Lys Ala Leu Lys Ile
  1               5                  10                  15

Asn Trp Cys Ala Gly Glu Val Ser Leu Arg Val Arg Gln Asp Ala Met
             20                  25                  30

Gly


<210> SEQ ID NO 133
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE  ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
```

```
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the WNV
<220> FEATURE:
<221> NAME/KEY: DISULFID
<222> LOCATION: (2)..(19)

<400> SEQUENCE: 133

Ala Cys Ser Asn Ile Val Ile Gly Ile Gly Asp Lys Ala Leu Lys Ile
  1               5                  10                  15

Asn Trp Cys Ala Ser Ser Glu Arg Val Asp Val Arg Leu Asp Asp Asp
             20                  25                  30

Gly


<210> SEQ ID NO 134
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(32)
<223> OTHER INFORMATION: NS3pro activation inhibitor segment,
      NS3pro N-terminal domain binding segment,
      segment NS4A from HCV
<220> FEATURE:
<221> NAME/KEY: DISULFID
<222> LOCATION: (2)..(19)

<400> SEQUENCE: 134

Ala Cys Ser Asn Ile Val Ile Gly Ile Gly Asp Lys Ala Leu Lys Ile
  1               5                  10                  15

Asn Trp Cys Ala Thr Gly Ser Val Val Ile Val Gly Arg Ile Ile Leu
             20                  25                  30


<210> SEQ ID NO 135
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
```

```
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(32)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: DISULFID
<222> LOCATION: (2)..(19)

<400> SEQUENCE: 135

Ala Cys Ser Asn Ile Val Ile Gly Ile Gly Asp Lys Ala Leu Lys Ile
  1               5                  10                  15

Asn Trp Cys Ala Thr Gly Ser Val Val Ile Val Gly Gln Ile Ile Leu
             20                  25                  30


<210> SEQ ID NO 136
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: DISULFID
<222> LOCATION: (2)..(19)

<400> SEQUENCE: 136

Ala Cys Ser Asn Ile Val Ile Gly Ile Gly Asp Lys Ala Leu Lys Ile
  1               5                  10                  15

Asn Trp Cys Ala Ala Ser His Asn Ile Leu Val Glu Val Gln Asp Asp
             20                  25                  30

Gly
```

<210> SEQ ID NO 137
<211> LENGTH: 33
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the virus dengue 3
<220> FEATURE:
<221> NAME/KEY: DISULFID
<222> LOCATION: (2)..(19)

<400> SEQUENCE: 137

```
Ala Cys Ser Asn Ile Val Ile Gly Ile Gly Asp Lys Ala Leu Lys Ile
  1               5                  10                  15

Asn Trp Cys Ala Val Ser His Asn Leu Met Ile Thr Val Asp Asp Asp
             20                  25                  30

Gly
```

<210> SEQ ID NO 138
<211> LENGTH: 33
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro C-terminal domain binding segment,
segment of NS2B from the virus dengue 4

<220> FEATURE:
<221> NAME/KEY: DISULFID
<222> LOCATION: (2)..(19)

<400> SEQUENCE: 138

Ala Cys Ser Asn Ile Val Ile Gly Ile Gly Asp Lys Ala Leu Lys Ile
1 5 10 15

Asn Trp Cys Ala Ser Ser Pro Ile Ile Glu Val Lys Gln Asp Glu Asp
20 25 30

Gly

<210> SEQ ID NO 139
<211> LENGTH: 33
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro N-terminal domain binding segment,
segment of NS2B from the virus DV2
<220> FEATURE:
<221> NAME/KEY: DISULFID
<222> LOCATION: (2)..(19)

<400> SEQUENCE: 139

Ala Cys Ser Asn Ile Val Ile Gly Ile Gly Asp Lys Ala Leu Lys Ile
1 5 10 15

Asn Trp Cys Ala Asp Leu Glu Leu Glu Arg Ala Ala Asp Val Lys Trp
20 25 30

Glu

<210> SEQ ID NO 140
<211> LENGTH: 33
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:

<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the virus dengue 1
<220> FEATURE:
<221> NAME/KEY: DISULFID
<222> LOCATION: (2)..(19)

<400> SEQUENCE: 140

```
Ala Cys Ser Asn Ile Val Ile Gly Ile Gly Asp Lys Ala Leu Lys Ile
  1               5                  10                  15

Asn Trp Cys Ala Asp Leu Ser Leu Glu Lys Ala Ala Glu Val Ser Trp
             20                  25                  30

Glu
```

<210> SEQ ID NO 141
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: DISULFID
<222> LOCATION: (2)..(19)

<400> SEQUENCE: 141

```
Ala Cys Ser Asn Ile Val Ile Gly Ile Gly Asp Lys Ala Leu Lys Ile
  1               5                  10                  15

Asn Trp Cys Ala Asp Leu Thr Val Glu Lys Ala Ala Asp Val Thr Trp
             20                  25                  30

Glu
```

<210> SEQ ID NO 142
<211> LENGTH: 33
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro N-terminal domain binding segment,
segment of NS2B from the virus dengue 4
<220> FEATURE:
<221> NAME/KEY: DISULFID
<222> LOCATION: (2)..(19)

<400> SEQUENCE: 142

Ala Cys Ser Asn Ile Val Ile Gly Ile Gly Asp Lys Ala Leu Lys Ile
1 5 10 15

Asn Trp Cys Ala Asp Leu Ser Leu Glu Lys Ala Ala Asn Val Gln Trp
20 25 30

Asp

<210> SEQ ID NO 143
<211> LENGTH: 33
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro N-terminal domain binding segment,
segment of NS2B from the WNV
<220> FEATURE:
<221> NAME/KEY: DISULFID
<222> LOCATION: (2)..(19)

<400> SEQUENCE: 143

```
Ala Cys Ser Asn Ile Val Ile Gly Ile Gly Asp Lys Ala Leu Lys Ile
  1               5                  10                  15

Asn Trp Cys Ala Asp Met Trp Ile Glu Arg Thr Ala Asp Ile Thr Trp
            20                  25                  30

Glu


<210> SEQ ID NO 144
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the YFV
<220> FEATURE:
<221> NAME/KEY: DISULFID
<222> LOCATION: (2)..(19)

<400> SEQUENCE: 144

Ala Cys Ser Asn Ile Val Ile Gly Ile Gly Asp Lys Ala Leu Lys Ile
  1               5                  10                  15

Asn Trp Cys Ala Gly Leu Glu Leu Lys Lys Leu Gly Glu Val Ser Trp
            20                  25                  30

Glu


<210> SEQ ID NO 145
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
```

```
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the Japanese Encephalitis
      virus
<220> FEATURE:
<221> NAME/KEY: DISULFID
<222> LOCATION: (2)..(19)

<400> SEQUENCE: 145

Ala Cys Ser Asn Ile Val Ile Gly Ile Gly Asp Lys Ala Leu Lys Ile
  1               5                  10                  15

Asn Trp Cys Ala Asp Met Trp Leu Glu Arg Ala Ala Asp Ile Ser Trp
             20                  25                  30

Glu


<210> SEQ ID NO 146
<211> LENGTH: 33
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro N-terminal domain binding segment,
      segment of NS2B from the Thick-Borne
      Encephalitis virus
<220> FEATURE:
<221> NAME/KEY: DISULFID
<222> LOCATION: (2)..(19)

<400> SEQUENCE: 146

Ala Cys Ser Asn Ile Val Ile Gly Ile Gly Asp Lys Ala Leu Lys Ile
  1               5                  10                  15

Asn Trp Cys Ala Gln Leu Val Ala Glu Trp Ser Gly Cys Val Glu Trp
             20                  25                  30

His


<210> SEQ ID NO 147
<211> LENGTH: 44
<212> TYPE: PRT
<213> ORGANISM: Artificial Sequence
<220> FEATURE:
<223> OTHER INFORMATION: Description of the Artificial Sequence:
      chimerical peptide
```

<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
      NS3pro C-terminal domain binding segment,
      segment of NS2B from the virus DV2
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
      ER is the Endoplasmic Reticulum
<220> FEATURE:
<221> NAME/KEY: SIGNAL
<222> LOCATION: (41)..(44)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: ()..(19)

<400> SEQUENCE: 147

```
Ala Cys Ser Asn Ile Val Ile Gly Ile Gly Asp Lys Ala Leu Lys Ile
  1               5                  10                  15

Asn Trp Cys Ala Ser Ser Pro Ile Leu Ser Ile Thr Ile Ser Glu Asp
             20                  25                  30

Gly Ala Leu Arg Arg Arg Arg Leu Lys Asp Glu Leu
         35                  40
```

<210> SEQ ID NO 148
<211> LENGTH: 44
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: MOD_RES
<222> LOCATION: (1)
<223> OTHER INFORMATION: Linker residue beta-Alanine ; bAla
<220> FEATURE:
<221> NAME/KEY: DOMAIN
<222> LOCATION: (2)..(19)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: DOMAIN
<222> LOCATION: (21)..(33)
<223> OTHER INFORMATION: NS3pro activation inhibitor segment,
NS3pro N-terminal domain binding segment,
segment of NS2B from the virus DV2
<220> FEATURE:
<221> NAME/KEY: MOD_RES
<222> LOCATION: (34)
<223> OTHER INFORMATION: Linker residue beta-Alanine ; bAla
<220> FEATURE:
<221> NAME/KEY: SIGNAL
<222> LOCATION: (35)..(40)
<223> OTHER INFORMATION: ER cytosolic retention signal
ER is the Endoplasmic Reticulum
<220> FEATURE:
<221> NAME/KEY: SIGNAL
<222> LOCATION: (41)..(44)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: ()..(19)

<400> SEQUENCE: 148

```
Ala Cys Ser Asn Ile Val Ile Gly Ile Gly Asp Lys Ala Leu Lys Ile
  1               5                  10                  15

Asn Trp Cys Ala Asp Leu Glu Leu Glu Arg Ala Ala Asp Val Lys Trp
             20                  25                  30

Glu Ala Leu Arg Arg Arg Arg Leu Lys Asp Glu Leu
         35                  40
```

<210> SEQ ID NO 149
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
NS3pro C-terminal domain binding segment,
segment of NS2B from the YFV
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 149

```
Arg Arg Arg Arg Arg Arg Arg Arg Arg Arg Gly Gly Gly Ser Ser Ala
  1               5                  10                  15

Arg Tyr Asp Val Ala Leu Ser Glu Gln Gly Gly Gly Lys Asp Glu Leu
             20                  25                  30
```

-continued

```
<210> SEQ ID NO 150
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the Japanese Encephalitis
      virus
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 150

Arg Arg Arg Arg Arg Arg Arg Arg Arg Arg Gly Gly Gly Ser Ser Arg
  1               5                  10                  15

Arg Leu Asp Val Lys Leu Asp Asp Asp Gly Gly Gly Lys Asp Glu Leu
             20                  25                  30


<210> SEQ ID NO 151
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 151

Arg Arg Arg Arg Arg Arg Arg Arg Arg Arg Gly Gly Gly Gly Glu Val
  1               5                  10                  15
```

Ser Leu Arg Val Arg Gln Asp Ala Met Gly Gly Gly Lys Asp Glu Leu
20 25 30

<210> SEQ ID NO 152
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment, NS3pro C-terminal domain binding segment, segment of NS2B from the WNV
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 152

Arg Arg Arg Arg Arg Arg Arg Arg Arg Arg Gly Gly Gly Ser Ser Glu
1 5 10 15

Arg Val Asp Val Arg Leu Asp Asp Asp Gly Gly Gly Lys Asp Glu Leu
20 25 30

<210> SEQ ID NO 153
<211> LENGTH: 31
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(25)
<223> OTHER INFORMATION: NS3pro activation inhibitor segment, NS3pro N-terminal domain binding segment, segment NS4A from HCV
<220> FEATURE:
<221> NAME/KEY: DOMAIN
<222> LOCATION: (26)..(27)
<223> OTHER INFORMATION: linker segment
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 153

Arg Arg Arg Arg Arg Arg Arg Arg Arg Arg Gly Gly Gly Thr Gly Ser

-continued

```
 1               5                  10                  15

Val Val Ile Val Gly Arg Ile Ile Leu Gly Gly Lys Asp Glu Leu
             20                  25                  30


<210> SEQ ID NO 154
<211> LENGTH: 31
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(25)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: DOMAIN
<222> LOCATION: (26)..(27)
<223> OTHER INFORMATION: linker segment
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 154

Arg Arg Arg Arg Arg Arg Arg Arg Arg Arg Gly Gly Gly Thr Gly Ser
 1               5                  10                  15

Val Val Ile Val Gly Gln Ile Ile Leu Gly Gly Lys Asp Glu Leu
             20                  25                  30


<210> SEQ ID NO 155
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end
```

<400> SEQUENCE: 155

Arg Arg Arg Arg Arg Arg Arg Arg Arg Arg Gly Gly Gly Ala Ser His
1 5 10 15

Asn Ile Leu Val Glu Val Gln Asp Asp Gly Gly Gly Lys Asp Glu Leu
20 25 30

<210> SEQ ID NO 156
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment, NS3pro C-terminal domain binding segment, segment of NS2B from the virus dengue 3
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 156

Arg Arg Arg Arg Arg Arg Arg Arg Arg Arg Gly Gly Gly Val Ser His
1 5 10 15

Asn Leu Met Ile Thr Val Asp Asp Asp Gly Gly Gly Lys Asp Glu Leu
20 25 30

<210> SEQ ID NO 157
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment, NS3pro C-terminal domain binding segment, segment of NS2B from the virus dengue 4
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:

<223> OTHER INFORMATION: Carboxylic C-terminal end

<400> SEQUENCE: 157

Arg Arg Arg Arg Arg Arg Arg Arg Arg Arg Gly Gly Gly Ser Ser Pro
1 5 10 15

Ile Ile Glu Val Lys Gln Asp Glu Asp Gly Gly Gly Lys Asp Glu Leu
20 25 30

<210> SEQ ID NO 158
<211> LENGTH: 30
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus DV2
<220> FEATURE:
<221> NAME/KEY: DOMAIN
<222> LOCATION: (14)..(17)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 158

Ser Ser Pro Ile Leu Ser Ile Thr Ile Ser Glu Asp Gly Gly Gly Gly
1 5 10 15

Tyr Gly Arg Lys Lys Arg Arg Gln Arg Arg Arg Pro Pro Gln
20 25 30

<210> SEQ ID NO 159
<211> LENGTH: 26
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus DV2
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 159

Ser Ser Pro Ile Leu Ser Ile Thr Ile Ser Glu Asp Gly Gly Gly Gly
1 5 10 15

Arg Arg Arg Arg Arg Arg Arg Arg Arg Arg
20 25

<210> SEQ ID NO 160
<211> LENGTH: 26
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 160

Ala Ser His Asn Ile Leu Val Glu Val Gln Asp Asp Gly Gly Gly Gly
1 5 10 15

Arg Arg Arg Arg Arg Arg Arg Arg Arg Arg
20 25

<210> SEQ ID NO 161
<211> LENGTH: 26
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 161

Val Ser His Asn Leu Met Ile Thr Val Asp Asp Asp Gly Gly Gly Gly
1 5 10 15

Arg Arg Arg Arg Arg Arg Arg Arg Arg Arg
20 25

<210> SEQ ID NO 162
<211> LENGTH: 26
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 162

Ser Ser Pro Ile Ile Glu Val Lys Gln Asp Glu Asp Gly Gly Gly Gly

-continued

```
  1               5                   10                  15

Arg Arg Arg Arg Arg Arg Arg Arg Arg Arg
             20                  25


<210> SEQ ID NO 163
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 163

Ser Ser Ala Arg Tyr Asp Val Ala Leu Ser Glu Gln Gly Gly Gly Gly
  1               5                   10                  15

Arg Arg Arg Arg Arg Arg Arg Arg Arg Arg
             20                  25


<210> SEQ ID NO 164
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Japanese Encephalitis
      virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 164

Ser Ser Arg Arg Leu Asp Val Lys Leu Asp Asp Asp Gly Gly Gly Gly
  1               5                   10                  15

Arg Arg Arg Arg Arg Arg Arg Arg Arg Arg
             20                  25


<210> SEQ ID NO 165
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
```

```
      NS3pro C-terminal domain binding segment,
      segment of NS2B from the Thick-Borne
      Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 165

Gly Glu Val Ser Leu Arg Val Arg Gln Asp Ala Met Gly Gly Gly Gly
  1               5                  10                  15

Arg Arg Arg Arg Arg Arg Arg Arg Arg Arg
             20                  25


<210> SEQ ID NO 166
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 166

Ser Ser Glu Arg Val Asp Val Arg Leu Asp Asp Asp Gly Gly Gly Gly
  1               5                  10                  15

Arg Arg Arg Arg Arg Arg Arg Arg Arg Arg
             20                  25


<210> SEQ ID NO 167
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
```

<223> OTHER INFORMATION: ER Retention signal KDEL
<220> FEATURE:
<223> OTHER INFORMATION: Carboxylic C-terminal end

<400> SEQUENCE: 167

Ser Ser Pro Ile Leu Ser Ile Thr Ile Ser Glu Asp Gly Gly Gly Gly
1 5 10 15

Arg Arg Arg Arg Arg Arg Arg Arg Arg Arg Gly Gly Lys Asp Glu Leu
20 25 30

<210> SEQ ID NO 168
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 168

Ala Ser His Asn Ile Leu Val Glu Val Gln Asp Asp Gly Gly Gly Gly
1 5 10 15

Arg Arg Arg Arg Arg Arg Arg Arg Arg Arg Gly Gly Lys Asp Glu Leu
20 25 30

<210> SEQ ID NO 169
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:

```
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 169

Val Ser His Asn Leu Met Ile Thr Val Asp Asp Asp Gly Gly Gly Gly
  1               5                  10                  15

Arg Arg Arg Arg Arg Arg Arg Arg Arg Arg Gly Gly Lys Asp Glu Leu
             20                  25                  30


<210> SEQ ID NO 170
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 170

Ser Ser Pro Ile Ile Glu Val Lys Gln Asp Glu Asp Gly Gly Gly Gly
  1               5                  10                  15

Arg Arg Arg Arg Arg Arg Arg Arg Arg Arg Gly Gly Lys Asp Glu Leu
             20                  25                  30


<210> SEQ ID NO 171
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
```

<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 171

```
Ser Ser Ala Arg Tyr Asp Val Ala Leu Ser Glu Gln Gly Gly Gly Gly
  1               5                  10                  15

Arg Arg Arg Arg Arg Arg Arg Arg Arg Arg Gly Gly Lys Asp Glu Leu
             20                  25                  30
```

<210> SEQ ID NO 172
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Japanese Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 172

```
Ser Ser Arg Arg Leu Asp Val Lys Leu Asp Asp Asp Gly Gly Gly Gly
  1               5                  10                  15

Arg Arg Arg Arg Arg Arg Arg Arg Arg Arg Gly Gly Lys Asp Glu Leu
             20                  25                  30
```

<210> SEQ ID NO 173
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Thick-Borne Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)

```
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 173

Gly Glu Val Ser Leu Arg Val Arg Gln Asp Ala Met Gly Gly Gly Gly
  1               5                  10                  15

Arg Arg Arg Arg Arg Arg Arg Arg Arg Arg Gly Gly Lys Asp Glu Leu
             20                  25                  30


<210> SEQ ID NO 174
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 174

Ser Ser Glu Arg Val Asp Val Arg Leu Asp Asp Asp Gly Gly Gly Gly
  1               5                  10                  15

Arg Arg Arg Arg Arg Arg Arg Arg Arg Arg Gly Gly Lys Asp Glu Leu
             20                  25                  30


<210> SEQ ID NO 175
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: DOMAIN
<222> LOCATION: (14)..(16)
<223> OTHER INFORMATION: linker segment
<220> FEATURE:
```

-continued

```
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 175

Ser Ser Pro Ile Leu Ser Ile Thr Ile Ser Glu Asp Gly Gly Gly Gly
  1               5                  10                  15

Tyr Gly Arg Lys Lys Arg Arg Gln Arg Arg Arg Pro Pro Gln Gly Gly
            20                  25                  30

Lys Asp Glu Leu
        35


<210> SEQ ID NO 176
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 176

Ala Ser His Asn Ile Leu Val Glu Val Gln Asp Asp Gly Gly Gly Gly
  1               5                  10                  15

Tyr Gly Arg Lys Lys Arg Arg Gln Arg Arg Arg Pro Pro Gln Gly Gly
            20                  25                  30

Lys Asp Glu Leu
        35


<210> SEQ ID NO 177
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
```

<223> OTHER INFORMATION: NS3pro activation inhibitor segment,
      NS3pro C-terminal domain binding segment,
      segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 177

```
Val Ser His Asn Leu Met Ile Thr Val Asp Asp Asp Gly Gly Gly Gly
  1               5                  10                  15

Tyr Gly Arg Lys Lys Arg Arg Gln Arg Arg Arg Pro Pro Gln Gly Gly
             20                  25                  30

Lys Asp Glu Leu
         35
```

<210> SEQ ID NO 178
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 178

```
Ser Ser Pro Ile Ile Glu Val Lys Gln Asp Glu Asp Gly Gly Gly Gly
  1               5                  10                  15

Tyr Gly Arg Lys Lys Arg Arg Gln Arg Arg Arg Pro Pro Gln Gly Gly
             20                  25                  30

Lys Asp Glu Leu
         35
```

<210> SEQ ID NO 179
<211> LENGTH: 36

<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 179

```
Ser Ser Ala Arg Tyr Asp Val Ala Leu Ser Glu Gln Gly Gly Gly Gly
  1               5                  10                  15

Tyr Gly Arg Lys Lys Arg Arg Gln Arg Arg Arg Pro Pro Gln Gly Gly
            20                  25                  30

Lys Asp Glu Leu
        35
```

<210> SEQ ID NO 180
<211> LENGTH: 36
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 180

```
Ser Ser Arg Arg Leu Asp Val Lys Leu Asp Asp Asp Gly Gly Gly Gly
  1               5                  10                  15
```

Tyr Gly Arg Lys Lys Arg Arg Gln Arg Arg Arg Pro Pro Gln Gly Gly
20 25 30

Lys Asp Glu Leu
35

<210> SEQ ID NO 181
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Thick-Borne Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 181

Gly Glu Val Ser Leu Arg Val Arg Gln Asp Ala Met Gly Gly Gly Gly
1 5 10 15

Tyr Gly Arg Lys Lys Arg Arg Gln Arg Arg Arg Pro Pro Gln Gly Gly
20 25 30

Lys Asp Glu Leu
35

<210> SEQ ID NO 182
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)

<223> OTHER INFORMATION: ER Retention signal KDEL
<220> FEATURE:
<223> OTHER INFORMATION: Carboxylic C-terminal end

<400> SEQUENCE: 182

Ser Ser Glu Arg Val Asp Val Arg Leu Asp Asp Asp Gly Gly Gly Gly
1 5 10 15

Tyr Gly Arg Lys Lys Arg Arg Gln Arg Arg Arg Pro Pro Gln Gly Gly
20 25 30

Lys Asp Glu Leu
35

<210> SEQ ID NO 183
<211> LENGTH: 30
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 183

Ala Ser His Asn Ile Leu Val Glu Val Gln Asp Asp Gly Gly Gly Gly
1 5 10 15

Tyr Gly Arg Lys Lys Arg Arg Gln Arg Arg Arg Pro Pro Gln
20 25 30

<210> SEQ ID NO 184
<211> LENGTH: 30
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 184

Val Ser His Asn Leu Met Ile Thr Val Asp Asp Asp Gly Gly Gly Gly
1 5 10 15

Tyr Gly Arg Lys Lys Arg Arg Gln Arg Arg Arg Pro Pro Gln
20 25 30

<210> SEQ ID NO 185
<211> LENGTH: 30

<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 185

```
Ser Ser Pro Ile Ile Glu Val Lys Gln Asp Glu Asp Gly Gly Gly Gly
  1               5                  10                  15

Tyr Gly Arg Lys Lys Arg Arg Gln Arg Arg Arg Pro Pro Gln
             20                  25                  30
```

<210> SEQ ID NO 186
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 186

```
Ser Ser Glu Arg Val Asp Val Arg Leu Asp Asp Asp Gly Gly Gly Gly
  1               5                  10                  15

Tyr Gly Arg Lys Lys Arg Arg Gln Arg Arg Arg Pro Pro Gln
             20                  25                  30
```

<210> SEQ ID NO 187
<211> LENGTH: 30
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)

<223> OTHER INFORMATION: cell penetrating TAT peptide

<400> SEQUENCE: 187

Ser Ser Ala Arg Tyr Asp Val Ala Leu Ser Glu Gln Gly Gly Gly Gly
1 5 10 15

Tyr Gly Arg Lys Lys Arg Arg Gln Arg Arg Arg Pro Pro Gln
20 25 30

<210> SEQ ID NO 188
<211> LENGTH: 30
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Japanese Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 188

Ser Ser Arg Arg Leu Asp Val Lys Leu Asp Asp Asp Gly Gly Gly Gly
1 5 10 15

Tyr Gly Arg Lys Lys Arg Arg Gln Arg Arg Arg Pro Pro Gln
20 25 30

<210> SEQ ID NO 189
<211> LENGTH: 30
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Thick-Borne Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 189

Gly Glu Val Ser Leu Arg Val Arg Gln Asp Ala Met Gly Gly Gly Gly
1 5 10 15

Tyr Gly Arg Lys Lys Arg Arg Gln Arg Arg Arg Pro Pro Gln
20 25 30

<210> SEQ ID NO 190
<211> LENGTH: 30
<212> TYPE: PRT
<213> ORGANISM: Artificial Sequence
<220> FEATURE:

<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus DV2
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 190

Asp Leu Glu Leu Glu Arg Ala Ala Asp Val Lys Trp Glu Gly Gly Gly
1               5                   10                  15

Tyr Gly Arg Lys Lys Arg Arg Gln Arg Arg Arg Pro Pro Gln
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 191

Asp Leu Ser Leu Glu Lys Ala Ala Glu Val Ser Trp Glu Gly Gly Gly
1               5                   10                  15

Tyr Gly Arg Lys Lys Arg Arg Gln Arg Arg Arg Pro Pro Gln
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 192

```
Asp Leu Thr Val Glu Lys Ala Ala Asp Val Thr Trp Glu Gly Gly Gly
  1               5                  10                  15

Tyr Gly Arg Lys Lys Arg Arg Gln Arg Arg Arg Pro Pro Gln
             20                  25                  30


<210> SEQ ID NO 193
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 193

Asp Leu Ser Leu Glu Lys Ala Ala Asn Val Gln Trp Asp Gly Gly Gly
  1               5                  10                  15

Tyr Gly Arg Lys Lys Arg Arg Gln Arg Arg Arg Pro Pro Gln
             20                  25                  30


<210> SEQ ID NO 194
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 194

Asp Met Trp Ile Glu Arg Thr Ala Asp Ile Thr Trp Glu Gly Gly Gly
  1               5                  10                  15

Tyr Gly Arg Lys Lys Arg Arg Gln Arg Arg Arg Pro Pro Gln
             20                  25                  30


<210> SEQ ID NO 195
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
```

```
<223> OTHER INFORMATION: NS3pro activation inhibitor segment,
      NS3pro N-terminal domain binding segment,
      segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 195

Gly Leu Glu Leu Lys Lys Leu Gly Glu Val Ser Trp Glu Gly Gly Gly
  1               5                  10                  15

Tyr Gly Arg Lys Lys Arg Arg Gln Arg Arg Arg Pro Pro Gln
             20                  25                  30


<210> SEQ ID NO 196
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Japanese Encephalitis
      virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 196

Asp Met Trp Leu Glu Arg Ala Ala Asp Ile Ser Trp Glu Gly Gly Gly
  1               5                  10                  15

Tyr Gly Arg Lys Lys Arg Arg Gln Arg Arg Arg Pro Pro Gln
             20                  25                  30


<210> SEQ ID NO 197
<211> LENGTH: 30
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Thick-Borne
      Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide

<400> SEQUENCE: 197

Gln Leu Val Ala Glu Trp Ser Gly Cys Val Glu Trp His Gly Gly Gly
  1               5                  10                  15
```

```
Tyr Gly Arg Lys Lys Arg Arg Gln Arg Arg Arg Pro Pro Gln
             20                  25                  30


<210> SEQ ID NO 198
<211> LENGTH: 29
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(29)
<223> OTHER INFORMATION: cell penetrating TAT peptide

<400> SEQUENCE: 198

Thr Gly Ser Val Val Ile Val Gly Arg Ile Ile Leu Gly Gly Gly Tyr
  1               5                  10                  15

Gly Arg Lys Lys Arg Arg Gln Arg Arg Arg Pro Pro Gln
             20                  25


<210> SEQ ID NO 199
<211> LENGTH: 29
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(29)
<223> OTHER INFORMATION: cell penetrating TAT peptide

<400> SEQUENCE: 199

Thr Gly Ser Val Val Ile Val Gly Gln Ile Ile Leu Gly Gly Gly Tyr
  1               5                  10                  15

Gly Arg Lys Lys Arg Arg Gln Arg Arg Arg Pro Pro Gln
             20                  25


<210> SEQ ID NO 200
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
```

```
      segment of NS2B from the virus DV2
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 200

Asp Leu Glu Leu Glu Arg Ala Ala Asp Val Lys Trp Glu Gly Gly Gly
  1               5                  10                  15

Tyr Gly Arg Lys Lys Arg Arg Gln Arg Arg Arg Pro Pro Gln Gly Gly
             20                  25                  30

Lys Asp Glu Leu
         35


<210> SEQ ID NO 201
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 201

Asp Leu Ser Leu Glu Lys Ala Ala Glu Val Ser Trp Glu Gly Gly Gly
  1               5                  10                  15

Tyr Gly Arg Lys Lys Arg Arg Gln Arg Arg Arg Pro Pro Gln Gly Gly
             20                  25                  30

Lys Asp Glu Leu
         35


<210> SEQ ID NO 202
<211> LENGTH: 36
<212> TYPE: PRT
<213> ORGANISM: Artificial Sequence
```

```
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 202

Asp Leu Thr Val Glu Lys Ala Ala Asp Val Thr Trp Glu Gly Gly Gly
  1               5                  10                  15

Tyr Gly Arg Lys Lys Arg Arg Gln Arg Arg Arg Pro Pro Gln Gly Gly
             20                  25                  30

Lys Asp Glu Leu
         35


<210> SEQ ID NO 203
<211> LENGTH: 36
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 203

Asp Leu Ser Leu Glu Lys Ala Ala Asn Val Gln Trp Asp Gly Gly Gly
  1               5                  10                  15

Tyr Gly Arg Lys Lys Arg Arg Gln Arg Arg Arg Pro Pro Gln Gly Gly
             20                  25                  30
```

Lys Asp Glu Leu
35

<210> SEQ ID NO 204
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 204

Asp Met Trp Ile Glu Arg Thr Ala Asp Ile Thr Trp Glu Gly Gly Gly
1 5 10 15

Tyr Gly Arg Lys Lys Arg Arg Gln Arg Arg Arg Pro Pro Gln Gly Gly
20 25 30

Lys Asp Glu Leu
35

<210> SEQ ID NO 205
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 205

Gly Leu Glu Leu Lys Lys Leu Gly Glu Val Ser Trp Glu Gly Gly Gly
1 5 10 15

Tyr Gly Arg Lys Lys Arg Arg Gln Arg Arg Arg Pro Pro Gln Gly Gly
20 25 30

Lys Asp Glu Leu
35

<210> SEQ ID NO 206
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the Japanese Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:
<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 206

Asp Met Trp Leu Glu Arg Ala Ala Asp Ile Ser Trp Glu Gly Gly Gly
1 5 10 15

Tyr Gly Arg Lys Lys Arg Arg Gln Arg Arg Arg Pro Pro Gln Gly Gly
20 25 30

Lys Asp Glu Leu
35

<210> SEQ ID NO 207
<211> LENGTH: 36
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the Thick-Borne Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(30)
<223> OTHER INFORMATION: cell penetrating TAT peptide
<220> FEATURE:

<221> NAME/KEY: DOMAIN
<222> LOCATION: (31)..(32)
<223> OTHER INFORMATION: linker segment
<220> FEATURE:
<221> NAME/KEY: SIGNAL
<222> LOCATION: (33)..(36)
<223> OTHER INFORMATION: ER Retention signal KDEL
<220> FEATURE:
<223> OTHER INFORMATION: Carboxylic C-terminal end

<400> SEQUENCE: 207

Gln Leu Val Ala Glu Trp Ser Gly Cys Val Glu Trp His Gly Gly Gly
1 5 10 15

Tyr Gly Arg Lys Lys Arg Arg Gln Arg Arg Arg Pro Pro Gln Gly Gly
20 25 30

Lys Asp Glu Leu
35

<210> SEQ ID NO 208
<211> LENGTH: 35
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(12)
<223> OTHER INFORMATION: NS3pro activation inhibitor segment, NS3pro N-terminal domain binding segment, segment NS4A from HCV
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(29)
<223> OTHER INFORMATION: cell penetrating TAT peptide
<220> FEATURE:
<221> NAME/KEY: DOMAIN
<222> LOCATION: (30)..(31)
<223> OTHER INFORMATION: linker segment
<220> FEATURE:
<221> NAME/KEY: SIGNAL
<222> LOCATION: (32)..(35)
<223> OTHER INFORMATION: ER Retention signal KDEL
<220> FEATURE:
<223> OTHER INFORMATION: Carboxylic C-terminal end

<400> SEQUENCE: 208

Thr Gly Ser Val Val Ile Val Gly Arg Ile Ile Leu Gly Gly Gly Tyr
1 5 10 15

Gly Arg Lys Lys Arg Arg Gln Arg Arg Arg Pro Pro Gln Gly Gly Lys
20 25 30

Asp Glu Leu
35

<210> SEQ ID NO 209
<211> LENGTH: 35
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(12)
<223> OTHER INFORMATION: NS3pro activation inhibitor segment, NS3pro N-terminal domain binding segment, segment NS4A from HCV, mutation of R28 by Q -continued
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(29)
<223> OTHER INFORMATION: cell penetrating TAT peptide
<220> FEATURE:
<221> NAME/KEY: DOMAIN
<222> LOCATION: (30)..(31)
<223> OTHER INFORMATION: linker segment
<220> FEATURE:
<221> NAME/KEY: SIGNAL
<222> LOCATION: (32)..(35)
<223> OTHER INFORMATION: ER Retention signal KDEL
<220> FEATURE:
<223> OTHER INFORMATION: Carboxylic C-terminal end

<400> SEQUENCE: 209

```
Thr Gly Ser Val Val Ile Val Gly Gln Ile Ile Leu Gly Gly Gly Tyr
  1               5                  10                  15

Gly Arg Lys Lys Arg Arg Gln Arg Arg Arg Pro Pro Gln Gly Gly Lys
             20                  25                  30

Asp Glu Leu
         35
```

<210> SEQ ID NO 210
<211> LENGTH: 26
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the virus DV2
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 210

```
Asp Leu Glu Leu Glu Arg Ala Ala Asp Val Lys Trp Glu Gly Gly Gly
  1               5                  10                  15

Arg Arg Arg Arg Arg Arg Arg Arg Arg Arg
             20                  25
```

<210> SEQ ID NO 211
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the virus DV2
<220> FEATURE:
<221> NAME/KEY: DOMAIN
<222> LOCATION: (14)..(16)
<223> OTHER INFORMATION: linker segment
<220> FEATURE:

<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 211

Asp Leu Glu Leu Glu Arg Ala Ala Asp Val Lys Trp Glu Gly Gly Gly
1 5 10 15

Arg Arg Arg Arg Arg Arg Arg Arg Arg Arg Gly Gly Lys Asp Glu Leu
20 25 30

<210> SEQ ID NO 212
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 212

Asp Leu Ser Leu Glu Lys Ala Ala Glu Val Ser Trp Glu Gly Gly Gly
1 5 10 15

Arg Arg Arg Arg Arg Arg Arg Arg Arg Arg Gly Gly Lys Asp Glu Leu
20 25 30

<210> SEQ ID NO 213
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 3
<220> FEATURE:
<221> NAME/KEY: DOMAIN
<222> LOCATION: (14)..(16)

<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 213

```
Asp Leu Thr Val Glu Lys Ala Ala Asp Val Thr Trp Glu Gly Gly Gly
  1               5                  10                  15

Arg Arg Arg Arg Arg Arg Arg Arg Arg Arg Gly Gly Lys Asp Glu Leu
             20                  25                  30
```

<210> SEQ ID NO 214
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 214

```
Asp Leu Ser Leu Glu Lys Ala Ala Asn Val Gln Trp Asp Gly Gly Gly
  1               5                  10                  15

Arg Arg Arg Arg Arg Arg Arg Arg Arg Arg Gly Gly Lys Asp Glu Leu
             20                  25                  30
```

<210> SEQ ID NO 215
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the WNV
<220> FEATURE:

<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 215

Asp Met Trp Ile Glu Arg Thr Ala Asp Ile Thr Trp Glu Gly Gly Gly
1 5 10 15

Arg Arg Arg Arg Arg Arg Arg Arg Arg Arg Gly Gly Lys Asp Glu Leu
20 25 30

<210> SEQ ID NO 216
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 216

Gly Leu Glu Leu Lys Lys Leu Gly Glu Val Ser Trp Glu Gly Gly Gly
1 5 10 15

Arg Arg Arg Arg Arg Arg Arg Arg Arg Arg Gly Gly Lys Asp Glu Leu
20 25 30

<210> SEQ ID NO 217
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the Japanese Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 217

```
Asp Met Trp Leu Glu Arg Ala Ala Asp Ile Ser Trp Glu Gly Gly Gly
  1               5                  10                  15

Arg Arg Arg Arg Arg Arg Arg Arg Arg Arg Gly Gly Lys Asp Glu Leu
             20                  25                  30
```

<210> SEQ ID NO 218
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the Thick-Borne Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 218

```
Gln Leu Val Ala Glu Trp Ser Gly Cys Val Glu Trp His Gly Gly Gly
  1               5                  10                  15

Arg Arg Arg Arg Arg Arg Arg Arg Arg Arg Gly Gly Lys Asp Glu Leu
             20                  25                  30
```

<210> SEQ ID NO 219
<211> LENGTH: 31
<212> TYPE: PRT
<213> ORGANISM: Artificial Sequence
<220> FEATURE:
<223> OTHER INFORMATION: Description of the Artificial Sequence: chimerical peptide
<220> FEATURE:

```
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(25)
<223> OTHER INFORMATION: cell penetrating peptide R10
<220> FEATURE:
<221> NAME/KEY: DOMAIN
<222> LOCATION: (26)..(27)
<223> OTHER INFORMATION: linker segment
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 219

Thr Gly Ser Val Val Ile Val Gly Arg Ile Ile Leu Gly Gly Gly Arg
  1               5                  10                  15

Arg Arg Arg Arg Arg Arg Arg Arg Arg Gly Gly Lys Asp Glu Leu
             20                  25                  30


<210> SEQ ID NO 220
<211> LENGTH: 31
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(25)
<223> OTHER INFORMATION: cell penetrating peptide R10
<220> FEATURE:
<221> NAME/KEY: DOMAIN
<222> LOCATION: (26)..(27)
<223> OTHER INFORMATION: linker segment
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 220

Thr Gly Ser Val Val Ile Val Gly Gln Ile Ile Leu Gly Gly Gly Arg
  1               5                  10                  15

Arg Arg Arg Arg Arg Arg Arg Arg Arg Gly Gly Lys Asp Glu Leu
             20                  25                  30


<210> SEQ ID NO 221
<211> LENGTH: 26
<212> TYPE: PRT
<213> ORGANISM: Artificial Sequence
<220> FEATURE:
```

<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 1
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 221

Asp Leu Ser Leu Glu Lys Ala Ala Glu Val Ser Trp Glu Gly Gly Gly
1               5                   10                  15

Arg Arg Arg Arg Arg Arg Arg Arg Arg Arg
            20                  25

<210> SEQ ID NO 222
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 222

Asp Leu Thr Val Glu Lys Ala Ala Asp Val Thr Trp Glu Gly Gly Gly
1               5                   10                  15

Arg Arg Arg Arg Arg Arg Arg Arg Arg Arg
            20                  25

<210> SEQ ID NO 223
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 4
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 223

```
Asp Leu Ser Leu Glu Lys Ala Ala Asn Val Gln Trp Asp Gly Gly Gly
  1               5                  10                  15

Arg Arg Arg Arg Arg Arg Arg Arg Arg Arg
             20                  25


<210> SEQ ID NO 224
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the WNV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 224

Asp Met Trp Ile Glu Arg Thr Ala Asp Ile Thr Trp Glu Gly Gly Gly
  1               5                  10                  15

Arg Arg Arg Arg Arg Arg Arg Arg Arg Arg
             20                  25


<210> SEQ ID NO 225
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the YFV
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 225

Gly Leu Glu Leu Lys Lys Leu Gly Glu Val Ser Trp Glu Gly Gly Gly
  1               5                  10                  15

Arg Arg Arg Arg Arg Arg Arg Arg Arg Arg
             20                  25


<210> SEQ ID NO 226
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
```

<223> OTHER INFORMATION: NS3pro activation inhibitor segment,
      NS3pro N-terminal domain binding segment,
      segment of NS2B from the Japanese Encephalitis
      virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 226

```
Asp Met Trp Leu Glu Arg Ala Ala Asp Ile Ser Trp Glu Gly Gly Gly
  1               5                  10                  15

Arg Arg Arg Arg Arg Arg Arg Arg Arg Arg
             20                  25
```

<210> SEQ ID NO 227
<211> LENGTH: 26
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Thick-Borne
      Encephalitis virus
<220> FEATURE:
<221> NAME/KEY: DOMAIN
<222> LOCATION: (14)..(16)
<223> OTHER INFORMATION: linker segment
<220> FEATURE:
<221> NAME/KEY: DOMAIN
<222> LOCATION: (17)..(26)
<223> OTHER INFORMATION: cell penetrating peptide R10

<400> SEQUENCE: 227

```
Gln Leu Val Ala Glu Trp Ser Gly Cys Val Glu Trp His Gly Gly Gly
  1               5                  10                  15

Arg Arg Arg Arg Arg Arg Arg Arg Arg Arg
             20                  25
```

<210> SEQ ID NO 228
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(25)
<223> OTHER INFORMATION: cell penetrating peptide R10

<400> SEQUENCE: 228

```
Thr Gly Ser Val Val Ile Val Gly Arg Ile Ile Leu Gly Gly Gly Arg
  1               5                  10                  15
```

```
Arg Arg Arg Arg Arg Arg Arg Arg Arg
            20                  25


<210> SEQ ID NO 229
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: DOMAIN
<222> LOCATION: (13)..(15)
<223> OTHER INFORMATION: linker segment
<220> FEATURE:
<221> NAME/KEY: DOMAIN
<222> LOCATION: (16)..(25)
<223> OTHER INFORMATION: cell penetrating peptide R10

<400> SEQUENCE: 229

Thr Gly Ser Val Val Ile Val Gly Gln Ile Ile Leu Gly Gly Gly Arg
  1               5                  10                  15

Arg Arg Arg Arg Arg Arg Arg Arg Arg
            20                  25


<210> SEQ ID NO 230
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 230
```

Ser Ser Pro Ile Leu Ser Ile Thr Ile Ser Glu Asp Gly Ala Leu Arg
1 5 10 15

Arg Arg Arg Leu Ala Leu Arg Arg Arg Arg Leu Ala Lys Asp Glu Leu
20 25 30

<210> SEQ ID NO 231
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 231

Ala Ser His Asn Ile Leu Val Glu Val Gln Asp Asp Gly Ala Leu Arg
1 5 10 15

Arg Arg Arg Leu Ala Leu Arg Arg Arg Arg Leu Ala Lys Asp Glu Leu
20 25 30

<210> SEQ ID NO 232
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 232

Val Ser His Asn Leu Met Ile Thr Val Asp Asp Asp Gly Ala Leu Arg
1 5 10 15

Arg Arg Arg Leu Ala Leu Arg Arg Arg Arg Leu Ala Lys Asp Glu Leu
20 25 30

<210> SEQ ID NO 233
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 233

Ser Ser Pro Ile Ile Glu Val Lys Gln Asp Glu Asp Gly Ala Leu Arg
1 5 10 15

Arg Arg Arg Leu Ala Leu Arg Arg Arg Arg Leu Ala Lys Asp Glu Leu
20 25 30

<210> SEQ ID NO 234
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 234

```
Ser Ser Ala Arg Tyr Asp Val Ala Leu Ser Glu Gln Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 235
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:

<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 235

```
Ser Ser Arg Arg Leu Asp Val Lys Leu Asp Asp Asp Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 236
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 236

```
Gly Glu Val Ser Leu Arg Val Arg Gln Asp Ala Met Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 237
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 237

```
Ser Ser Glu Arg Val Asp Val Arg Leu Asp Asp Asp Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 238
<211> LENGTH: 27
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum

<400> SEQUENCE: 238

```
Ser Ser Pro Ile Leu Ser Ile Thr Ile Ser Glu Asp Gly Ala Leu Arg
  1               5                  10                  15

Arg Arg Arg Leu Ala Leu Arg Arg Arg Arg Leu
            20                  25


<210> SEQ ID NO 239
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 239

Ala Ser His Asn Ile Leu Val Glu Val Gln Asp Asp Gly Ala Leu Arg
  1               5                  10                  15

Arg Arg Arg Leu Ala Leu Arg Arg Arg Arg Leu
            20                  25


<210> SEQ ID NO 240
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
```

```
<400> SEQUENCE: 240

Val Ser His Asn Leu Met Ile Thr Val Asp Asp Asp Gly Ala Leu Arg
  1               5                  10                  15

Arg Arg Arg Leu Ala Leu Arg Arg Arg Arg Leu
             20                  25


<210> SEQ ID NO 241
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 241

Ser Ser Pro Ile Ile Glu Val Lys Gln Asp Glu Asp Gly Ala Leu Arg
  1               5                  10                  15

Arg Arg Arg Leu Ala Leu Arg Arg Arg Arg Leu
             20                  25


<210> SEQ ID NO 242
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
```

<223> OTHER INFORMATION: ER cytosolic retention signal
ER is the Endoplasmic Reticulum

<400> SEQUENCE: 242

```
Ser Ser Ala Arg Tyr Asp Val Ala Leu Ser Glu Gln Gly Ala Leu Arg
  1               5                  10                  15

Arg Arg Arg Leu Ala Leu Arg Arg Arg Arg Leu
             20                  25
```

<210> SEQ ID NO 243
<211> LENGTH: 27
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Japanese Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum

<400> SEQUENCE: 243

```
Ser Ser Arg Arg Leu Asp Val Lys Leu Asp Asp Asp Gly Ala Leu Arg
  1               5                  10                  15

Arg Arg Arg Leu Ala Leu Arg Arg Arg Arg Leu
             20                  25
```

<210> SEQ ID NO 244
<211> LENGTH: 27
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Thick-Borne Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)

```
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 244

Gly Glu Val Ser Leu Arg Val Arg Gln Asp Ala Met Gly Ala Leu Arg
 1               5                  10                  15

Arg Arg Arg Leu Ala Leu Arg Arg Arg Arg Leu
            20                  25

<210> SEQ ID NO 245
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 245

Ser Ser Glu Arg Val Asp Val Arg Leu Asp Asp Gly Ala Leu Arg
 1               5                  10                  15

Arg Arg Arg Leu Ala Leu Arg Arg Arg Arg Leu
            20                  25

<210> SEQ ID NO 246
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide
```

<400> SEQUENCE: 246

Ser Ser Pro Ile Leu Ser Ile Thr Ile Ser Glu Asp Gly Ala Leu Arg
1 5 10 15

Arg Arg Arg Leu Arg Arg Arg Arg Leu
20 25

<210> SEQ ID NO 247
<211> LENGTH: 25
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(20)
<223> OTHER INFORMATION: ER cytosolic retention signal Cell penetrating peptide

<400> SEQUENCE: 247

Ala Ser His Asn Ile Leu Val Glu Val Gln Asp Asp Gly Ala Leu Arg
1 5 10 15

Arg Arg Arg Leu Arg Arg Arg Arg Leu
20 25

<210> SEQ ID NO 248
<211> LENGTH: 25
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal Cell penetrating peptide

<400> SEQUENCE: 248

Val Ser His Asn Leu Met Ile Thr Val Asp Asp Asp Gly Ala Leu Arg
1 5 10 15

Arg Arg Arg Leu Arg Arg Arg Arg Leu
20 25

<210> SEQ ID NO 249
<211> LENGTH: 25
<212> TYPE: PRT
<213> ORGANISM: Artificial Sequence
<220> FEATURE:
<223> OTHER INFORMATION: Description of the Artificial Sequence: chimerical peptide

```
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(20)
<223> OTHER INFORMATION: ER cytosolic retention signal
      Cell penetrating peptide

<400> SEQUENCE: 249

Ser Ser Pro Ile Ile Glu Val Lys Gln Asp Glu Asp Gly Ala Leu Arg
  1               5                  10                  15

Arg Arg Arg Leu Arg Arg Arg Arg Leu
             20                  25


<210> SEQ ID NO 250
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 250

Ser Ser Ala Arg Tyr Asp Val Ala Leu Ser Glu Gln Gly Ala Leu Arg
  1               5                  10                  15

Arg Arg Arg Leu Arg Arg Arg Arg Leu
             20                  25


<210> SEQ ID NO 251
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Japanese Encephalitis
      virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(20)
<223> OTHER INFORMATION: ER cytosolic retention signal
      Cell penetrating peptide
```

```
<400> SEQUENCE: 251

Ser Ser Arg Arg Leu Asp Val Lys Leu Asp Asp Asp Gly Ala Leu Arg
1               5                   10                  15

Arg Arg Arg Leu Arg Arg Arg Arg Leu
            20                  25


<210> SEQ ID NO 252
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(20)
<223> OTHER INFORMATION: ER cytosolic retention signal
      Cell penetrating peptide

<400> SEQUENCE: 252

Gly Glu Val Ser Leu Arg Val Arg Gln Asp Ala Met Gly Ala Leu Arg
  1               5                   10                  15

Arg Arg Arg Leu Arg Arg Arg Arg Leu
              20                  25


<210> SEQ ID NO 253
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(20)
<223> OTHER INFORMATION: ER cytosolic retention signal
      Cell penetrating peptide

<400> SEQUENCE: 253

Ser Ser Glu Arg Val Asp Val Arg Leu Asp Asp Asp Gly Ala Leu Arg
  1               5                   10                  15

Arg Arg Arg Leu Arg Arg Arg Arg Leu
              20                  25


<210> SEQ ID NO 254
<211> LENGTH: 25
<212> TYPE: PRT
<213> ORGANISM: Artificial Sequence
<220> FEATURE:
```

```
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 254

Ser Ser Pro Ile Leu Ser Ile Thr Ile Ser Glu Asp Gly Ala Leu Arg
  1               5                  10                  15

Arg Arg Arg Leu Arg Arg Arg Arg Leu
             20                  25


<210> SEQ ID NO 255
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 255

Ala Ser His Asn Ile Leu Val Glu Val Gln Asp Asp Gly Ala Leu Arg
  1               5                  10                  15

Arg Arg Arg Leu Arg Arg Arg Arg Leu
             20                  25


<210> SEQ ID NO 256
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
```

<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 256

Val Ser His Asn Leu Met Ile Thr Val Asp Asp Asp Gly Ala Leu Arg
1               5                   10                  15

Arg Arg Arg Leu Arg Arg Arg Arg Leu
            20                  25

<210> SEQ ID NO 257
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 257

Ser Ser Pro Ile Ile Glu Val Lys Gln Asp Glu Asp Gly Ala Leu Arg
1               5                   10                  15

Arg Arg Arg Leu Arg Arg Arg Arg Leu
            20                  25

<210> SEQ ID NO 258
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used <220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal Cell penetrating peptide

<400> SEQUENCE: 258

```
Ser Ser Ala Arg Tyr Asp Val Ala Leu Ser Glu Gln Gly Ala Leu Arg
  1               5                  10                  15

Arg Arg Arg Leu Arg Arg Arg Arg Leu
             20                  25
```

<210> SEQ ID NO 259
<211> LENGTH: 25
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE ; MYRISTATE bound to the N terminal end of the chimerical peptide PALMITATE could also be used
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Japanese Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal Cell penetrating peptide

<400> SEQUENCE: 259

```
Ser Ser Arg Arg Leu Asp Val Lys Leu Asp Asp Asp Gly Ala Leu Arg
  1               5                  10                  15

Arg Arg Arg Leu Arg Arg Arg Arg Leu
             20                  25
```

<210> SEQ ID NO 260
<211> LENGTH: 25
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE ; MYRISTATE bound to the N terminal end of the chimerical peptide PALMITATE could also be used could also be used
<220> FEATURE:
<221> NAME/KEY: DOMAIN
<222> LOCATION: (1)..(13)

```
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 260

Gly Glu Val Ser Leu Arg Val Arg Gln Asp Ala Met Gly Ala Leu Arg
  1               5                  10                  15

Arg Arg Arg Leu Arg Arg Arg Arg Leu
             20                  25


<210> SEQ ID NO 261
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 261

Ser Ser Glu Arg Val Asp Val Arg Leu Asp Asp Asp Gly Ala Leu Arg
  1               5                  10                  15

Arg Arg Arg Leu Arg Arg Arg Arg Leu
             20                  25


<210> SEQ ID NO 262
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
```

<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 262

```
Ser Ser Pro Ile Leu Ser Ile Thr Ile Ser Glu Asp Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 263
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:

<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 263

```
Ala Ser His Asn Ile Leu Val Glu Val Gln Asp Asp Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 264
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: LIPID
<222> LOCATION: (1)
<223> OTHER INFORMATION: MYRISTATE ; MYRISTATE bound to the N terminal end of the chimerical peptide PALMITATE could also be used
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 264

```
Val Ser His Asn Leu Met Ile Thr Val Asp Asp Asp Gly Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 265
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:

<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 265

Ser Ser Pro Ile Ile Glu Val Lys Gln Asp Glu Asp Gly Ala Leu Arg
1               5                   10                  15

Arg Arg Arg Leu Ala Leu Arg Arg Arg Arg Leu Ala Lys Asp Glu Leu
            20                  25                  30

<210> SEQ ID NO 266
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)

<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 266

Ser Ser Ala Arg Tyr Asp Val Ala Leu Ser Glu Gln Gly Ala Leu Arg
1 5 10 15

Arg Arg Arg Leu Ala Leu Arg Arg Arg Arg Leu Ala Lys Asp Glu Leu
20 25 30

<210> SEQ ID NO 267
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 267

Ser Ser Arg Arg Leu Asp Val Lys Leu Asp Asp Asp Gly Ala Leu Arg
1 5 10 15

```
Arg Arg Arg Leu Ala Leu Arg Arg Arg Arg Leu Ala Lys Asp Glu Leu
            20                  25                  30


<210> SEQ ID NO 268
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 268

Gly Glu Val Ser Leu Arg Val Arg Gln Asp Ala Met Gly Ala Leu Arg
  1               5                  10                  15

Arg Arg Arg Leu Ala Leu Arg Arg Arg Arg Leu Ala Lys Asp Glu Leu
            20                  25                  30


<210> SEQ ID NO 269
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
```

```
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 269

Ser Ser Glu Arg Val Asp Val Arg Leu Asp Asp Asp Gly Ala Leu Arg
  1               5                  10                  15

Arg Arg Arg Leu Ala Leu Arg Arg Arg Arg Leu Ala Lys Asp Glu Leu
             20                  25                  30


<210> SEQ ID NO 270
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 270

Ser Ser Pro Ile Leu Ser Ile Thr Ile Ser Glu Asp Gly Ala Leu Arg
```

```
  1               5                   10                  15

Arg Arg Arg Leu Ala Leu Arg Arg Arg Arg Leu
             20                  25


<210> SEQ ID NO 271
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 271

Ala Ser His Asn Ile Leu Val Glu Val Gln Asp Asp Gly Ala Leu Arg
  1               5                   10                  15

Arg Arg Arg Leu Ala Ala Arg Arg Arg Arg Leu
             20                  25


<210> SEQ ID NO 272
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
```

ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum

<400> SEQUENCE: 272

Val Ser His Asn Leu Met Ile Thr Val Asp Asp Asp Gly Ala Leu Arg
1 5 10 15

Arg Arg Arg Leu Ala Leu Arg Arg Arg Arg Leu
20 25

<210> SEQ ID NO 273
<211> LENGTH: 27
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum

<400> SEQUENCE: 273

Ser Ser Pro Ile Ile Glu Val Lys Gln Asp Glu Asp Gly Ala Leu Arg
1 5 10 15

Arg Arg Arg Leu Ala Leu Arg Arg Arg Arg Leu
20 25

<210> SEQ ID NO 274
<211> LENGTH: 27
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used <220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum

<400> SEQUENCE: 274

Ser Ser Ala Arg Tyr Asp Val Ala Leu Ser Glu Gln Gly Ala Leu Arg
1 5 10 15

Arg Arg Arg Leu Ala Leu Arg Arg Arg Arg Leu
20 25

<210> SEQ ID NO 275
<211> LENGTH: 27
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum

<400> SEQUENCE: 275

Ser Ser Arg Arg Leu Asp Val Lys Leu Asp Asp Asp Gly Ala Leu Arg
1 5 10 15

Arg Arg Arg Leu Ala Leu Arg Arg Arg Arg Leu
20 25

```
<210> SEQ ID NO 276
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 276

Gly Glu Val Ser Leu Arg Val Arg Gln Asp Ala Met Gly Ala Leu Arg
  1               5                  10                  15

Arg Arg Arg Leu Ala Leu Arg Arg Arg Arg Leu
             20                  25


<210> SEQ ID NO 277
<211> LENGTH: 27
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
```

```
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum

<400> SEQUENCE: 277

Ser Ser Glu Arg Val Asp Val Arg Leu Asp Asp Asp Gly Ala Leu Arg
  1               5                  10                  15

Arg Arg Arg Leu Ala Leu Arg Arg Arg Arg Leu
             20                  25


<210> SEQ ID NO 278
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 278

Asp Leu Glu Leu Glu Arg Ala Ala Asp Val Lys Trp Glu Ala Leu Arg
  1               5                  10                  15

Arg Arg Arg Leu Ala Leu Arg Arg Arg Arg Leu Ala Lys Asp Glu Leu
             20                  25                  30


<210> SEQ ID NO 279
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
```

segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 279

```
Asp Leu Ser Leu Glu Lys Ala Ala Glu Val Ser Trp Glu Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 280
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 280

Asp Leu Thr Val Glu Lys Ala Ala Asp Val Thr Trp Glu Ala Leu Arg
1 5 10 15

Arg Arg Arg Leu Ala Leu Arg Arg Arg Arg Leu Ala Lys Asp Glu Leu
20 25 30

<210> SEQ ID NO 281
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 281

Asp Leu Ser Leu Glu Lys Ala Ala Asn Val Gln Trp Asp Ala Leu Arg
1 5 10 15

Arg Arg Arg Leu Ala Leu Arg Arg Arg Arg Leu Ala Lys Asp Glu Leu
20 25 30

<210> SEQ ID NO 282
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 282

Asp Met Trp Ile Glu Arg Thr Ala Asp Ile Thr Trp Glu Ala Leu Arg
1               5                   10                  15

Arg Arg Arg Leu Ala Leu Arg Arg Arg Arg Leu Ala Lys Asp Glu Leu
            20                  25                  30

<210> SEQ ID NO 283
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 283

Gly Leu Glu Leu Lys Lys Leu Gly Glu Val Ser Trp Glu Ala Leu Arg
1               5                   10                  15

Arg Arg Arg Leu Ala Leu Arg Arg Arg Arg Leu Ala Lys Asp Glu Leu 20 25 30

<210> SEQ ID NO 284
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 284

Asp Met Trp Leu Glu Arg Ala Ala Asp Ile Ser Trp Glu Ala Leu Arg
1 5 10 15

Arg Arg Arg Leu Ala Leu Arg Arg Arg Arg Leu Ala Lys Asp Glu Leu
20 25 30

<210> SEQ ID NO 285
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Thick-Borne
Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 285

Gln Leu Val Ala Glu Trp Ser Gly Cys Val Glu Trp His Ala Leu Arg
1 5 10 15

Arg Arg Arg Leu Ala Leu Arg Arg Arg Arg Leu Ala Lys Asp Glu Leu
20 25 30

<210> SEQ ID NO 286
<211> LENGTH: 31
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(12)
<223> OTHER INFORMATION: NS3pro activation inhibitor segment,
NS3pro N-terminal domain binding segment,
segment NS4A from HCV
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: SIGNAL
<222> LOCATION: (14)..(19)
<223> OTHER INFORMATION: ER cytosolic retention signal
ER is the Endoplasmic Reticulum
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: SIGNAL
<222> LOCATION: (21)..(26)
<223> OTHER INFORMATION: ER cytosolic retention signal
ER is the Endoplasmic Reticulum
<220> FEATURE:
<221> NAME/KEY: MOD_RES
<222> LOCATION: (27)
<223> OTHER INFORMATION: Linker residue beta-Alanine ; bAla
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 286

Thr Gly Ser Val Val Ile Val Gly Arg Ile Ile Leu Ala Leu Arg Arg
1 5 10 15

Arg Arg Leu Ala Leu Arg Arg Arg Arg Leu Ala Lys Asp Glu Leu
20 25 30

<210> SEQ ID NO 287
<211> LENGTH: 31

```
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: SIGNAL
<222> LOCATION: (14)..(19)
<223> OTHER INFORMATION: ER cytosolic retention signal
      ER is the Endoplasmic Reticulum
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: SIGNAL
<222> LOCATION: (21)..(26)
<223> OTHER INFORMATION: ER cytosolic retention signal
      ER is the Endoplasmic Reticulum
<220> FEATURE:
<221> NAME/KEY: MOD_RES
<222> LOCATION: (27)
<223> OTHER INFORMATION: Linker residue beta-Alanine ; bAla
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 287

Thr Gly Ser Val Val Ile Val Gly Gln Ile Ile Leu Ala Leu Arg Arg
  1               5                  10                  15

Arg Arg Leu Ala Leu Arg Arg Arg Arg Leu Ala Lys Asp Glu Leu
            20                  25                  30


<210> SEQ ID NO 288
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
```

<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 288

```
Asp Leu Glu Leu Glu Arg Ala Ala Asp Val Lys Trp Glu Ala Leu Arg
  1               5                  10                  15

Arg Arg Arg Leu Ala Leu Arg Arg Arg Arg Leu Ala Lys Asp Glu Leu
             20                  25                  30
```

<210> SEQ ID NO 289
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 289

```
Asp Leu Ser Leu Glu Lys Ala Ala Glu Val Ser Trp Glu Ala Leu Arg
  1               5                  10                  15
```

```
Arg Arg Arg Leu Ala Leu Arg Arg Arg Arg Leu Ala Lys Asp Glu Leu
            20                  25                  30


<210> SEQ ID NO 290
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 290

Asp Leu Thr Val Glu Lys Ala Ala Asp Val Thr Trp Glu Ala Leu Arg
  1               5                  10                  15

Arg Arg Arg Leu Ala Leu Arg Arg Arg Arg Leu Ala Lys Asp Glu Leu
            20                  25                  30


<210> SEQ ID NO 291
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 4
```

<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 291

Asp Leu Ser Leu Glu Lys Ala Ala Asn Val Gln Trp Asp Ala Leu Arg
1 5 10 15

Arg Arg Arg Leu Ala Leu Arg Arg Arg Arg Leu Ala Lys Asp Glu Leu
20 25 30

<210> SEQ ID NO 292
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:

<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 292

Asp Met Trp Ile Glu Arg Thr Ala Asp Ile Thr Trp Glu Ala Leu Arg
1 5 10 15

Arg Arg Arg Leu Ala Leu Arg Arg Arg Arg Leu Ala Lys Asp Glu Leu
20 25 30

<210> SEQ ID NO 293
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 293

Gly Leu Glu Leu Lys Lys Leu Gly Glu Val Ser Trp Glu Ala Leu Arg
1 5 10 15

Arg Arg Arg Leu Ala Leu Arg Arg Arg Arg Leu Ala Lys Asp Glu Leu
20 25 30

<210> SEQ ID NO 294
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:

```
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Japanese Encephalitis
      virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 294

Asp Met Trp Leu Glu Arg Ala Ala Asp Ile Ser Trp Glu Ala Leu Arg
  1               5                  10                  15

Arg Arg Arg Leu Ala Leu Arg Arg Arg Arg Leu Ala Lys Asp Glu Leu
             20                  25                  30


<210> SEQ ID NO 295
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: SIGNAL
<222> LOCATION: (15)..(20)
<223> OTHER INFORMATION: ER cytosolic retention signal
      ER is the Endoplasmic Reticulum
<220> FEATURE:
```

```
<221> NAME/KEY: MOD_RES
<222> LOCATION: (21)
<223> OTHER INFORMATION: Linker residue beta-Alanine ; bAla
<220> FEATURE:
<221> NAME/KEY: SIGNAL
<222> LOCATION: (22)..(27)
<223> OTHER INFORMATION: ER cytosolic retention signal
      ER is the Endoplasmic Reticulum
<220> FEATURE:
<221> NAME/KEY: MOD_RES
<222> LOCATION: (28)
<223> OTHER INFORMATION: Linker residue beta-Alanine ; bAla
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 295

Gln Leu Val Ala Glu Trp Ser Gly Cys Val Glu Trp His Ala Leu Arg
  1               5                  10                  15

Arg Arg Arg Leu Ala Leu Arg Arg Arg Arg Leu Ala Lys Asp Glu Leu
             20                  25                  30


<210> SEQ ID NO 296
<211> LENGTH: 31
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: SIGNAL
<222> LOCATION: (14)..(19)
<223> OTHER INFORMATION: ER cytosolic retention signal
      ER is the Endoplasmic Reticulum
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: SIGNAL
<222> LOCATION: (21)..(26)
<223> OTHER INFORMATION: ER cytosolic retention signal
      ER is the Endoplasmic Reticulum
<220> FEATURE:
<221> NAME/KEY: MOD_RES
<222> LOCATION: (27)
<223> OTHER INFORMATION: Linker residue beta-Alanine ; bAla
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 296

Thr Gly Ser Val Val Ile Val Gly Arg Ile Ile Leu Ala Leu Arg Arg
  1               5                  10                  15
```

```
Arg Arg Leu Ala Leu Arg Arg Arg Arg Leu Ala Lys Asp Glu Leu
            20                  25                  30


<210> SEQ ID NO 297
<211> LENGTH: 31
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: SIGNAL
<222> LOCATION: (14)..(19)
<223> OTHER INFORMATION: ER cytosolic retention signal
      ER is the Endoplasmic Reticulum
<220> FEATURE:
<221> NAME/KEY: MOD_RES
<222> LOCATION: (20)
<223> OTHER INFORMATION: Linker residue beta-Alanine ; bAla
<220> FEATURE:
<221> NAME/KEY: SIGNAL
<222> LOCATION: (21)..(26)
<223> OTHER INFORMATION: ER cytosolic retention signal
      ER is the Endoplasmic Reticulum
<220> FEATURE:
<221> NAME/KEY: MOD_RES
<222> LOCATION: (27)
<223> OTHER INFORMATION: Linker residue beta-Alanine ; bAla
<220> FEATURE:
<221> NAME/KEY: SIGNAL
<222> LOCATION: (28)..(31)
<223> OTHER INFORMATION: ER Retention signal KDEL
<220> FEATURE:
<223> OTHER INFORMATION: Carboxylic C-terminal end

<400> SEQUENCE: 297

Thr Gly Ser Val Val Ile Val Gly Gln Ile Ile Leu Ala Leu Arg Arg
  1               5                  10                  15

Arg Arg Leu Ala Leu Arg Arg Arg Arg Leu Ala Lys Asp Glu Leu
            20                  25                  30


<210> SEQ ID NO 298
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
```

<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 298

Asp Leu Glu Leu Glu Arg Ala Ala Asp Val Lys Trp Glu Ala Leu Arg
  1               5                  10                  15

Arg Arg Arg Leu Arg Arg Arg Arg Leu
             20                  25

<210> SEQ ID NO 299
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 299

Asp Leu Glu Leu Glu Arg Ala Ala Asp Val Lys Trp Glu Ala Leu Arg
  1               5                  10                  15

Arg Arg Arg Leu Arg Arg Arg Arg Leu
             20                  25

<210> SEQ ID NO 300
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal Cell penetrating peptide

<400> SEQUENCE: 300

Asp Leu Ser Leu Glu Lys Ala Ala Glu Val Ser Trp Glu Ala Leu Arg
1 5 10 15

Arg Arg Arg Leu Arg Arg Arg Arg Leu
20 25

<210> SEQ ID NO 301
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 301

Asp Leu Thr Val Glu Lys Ala Ala Asp Val Thr Trp Glu Ala Leu Arg
1 5 10 15

Arg Arg Arg Leu Arg Arg Arg Arg Leu
20 25

<210> SEQ ID NO 302
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 302

-continued

```
Asp Leu Ser Leu Glu Lys Ala Ala Asn Val Gln Trp Asp Ala Leu Arg
  1             5                   10                  15

Arg Arg Arg Leu Arg Arg Arg Arg Leu
            20                  25


<210> SEQ ID NO 303
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 303

Asp Met Trp Ile Glu Arg Thr Ala Asp Ile Thr Trp Glu Ala Leu Arg
  1             5                   10                  15

Arg Arg Arg Leu Arg Arg Arg Arg Leu
            20                  25


<210> SEQ ID NO 304
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 304

Gly Leu Glu Leu Lys Lys Leu Gly Glu Val Ser Trp Glu Ala Leu Arg
  1             5                   10                  15

Arg Arg Arg Leu Arg Arg Arg Arg Leu
```

20 25

<210> SEQ ID NO 305
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 305

Asp Met Trp Leu Glu Arg Ala Ala Asp Ile Ser Trp Glu Ala Leu Arg
1 5 10 15

Arg Arg Arg Leu Arg Arg Arg Arg Leu
20 25

<210> SEQ ID NO 306
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Thick-Borne
Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 306

Gln Leu Val Ala Glu Trp Ser Gly Cys Val Glu Trp His Ala Leu Arg
1 5 10 15

Arg Arg Arg Leu Arg Arg Arg Arg Leu
20 25

```
<210> SEQ ID NO 307
<211> LENGTH: 24
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(24)
<223> OTHER INFORMATION: ER cytosolic retention signal
      Cell penetrating peptide

<400> SEQUENCE: 307

Thr Gly Ser Val Val Ile Val Gly Arg Ile Ile Leu Ala Leu Arg Arg
  1               5                  10                  15

Arg Arg Leu Arg Arg Arg Arg Leu
             20


<210> SEQ ID NO 308
<211> LENGTH: 24
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE  ; MYRISTATE bound to the N terminal
      end of the chimerical peptide
      PALMITATE could also be used
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(24)
<223> OTHER INFORMATION: ER cytosolic retention signal
      Cell penetrating peptide

<400> SEQUENCE: 308

Thr Gly Ser Val Val Ile Val Gly Gln Ile Ile Leu Ala Leu Arg Arg
  1               5                  10                  15

Arg Arg Leu Arg Arg Arg Arg Leu
             20


<210> SEQ ID NO 309
<211> LENGTH: 25
```

<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 309

```
Asp Leu Ser Leu Glu Lys Ala Ala Glu Val Ser Trp Glu Ala Leu Arg
 1               5                  10                  15

Arg Arg Arg Leu Arg Arg Arg Arg Leu
             20                  25
```

<210> SEQ ID NO 310
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 310

```
Asp Leu Thr Val Glu Lys Ala Ala Asp Val Thr Trp Glu Ala Leu Arg
 1               5                  10                  15

Arg Arg Arg Leu Arg Arg Arg Arg Leu
             20                  25
```

<210> SEQ ID NO 311
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:

<221> NAME/KEY: DOMAIN
<222> LOCATION: (15)..(25)
<223> OTHER INFORMATION: ER cytosolic retention signal
      Cell penetrating peptide

<400> SEQUENCE: 311

Asp Leu Ser Leu Glu Lys Ala Ala Asn Val Gln Trp Asp Ala Leu Arg
  1               5                  10                  15

Arg Arg Arg Leu Arg Arg Arg Arg Leu
             20                  25

<210> SEQ ID NO 312
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 312

Asp Met Trp Ile Glu Arg Thr Ala Asp Ile Thr Trp Glu Ala Leu Arg
  1               5                  10                  15

Arg Arg Arg Leu Arg Arg Arg Arg Leu
             20                  25

<210> SEQ ID NO 313
<211> LENGTH: 25
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
      Cell penetrating peptide

<400> SEQUENCE: 313

Gly Leu Glu Leu Lys Lys Leu Gly Glu Val Ser Trp Glu Ala Leu Arg
  1               5                  10                  15

Arg Arg Arg Leu Arg Arg Arg Arg Leu
             20                  25

<210> SEQ ID NO 314
<211> LENGTH: 25

<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 314

Asp Met Trp Leu Glu Arg Ala Ala Asp Ile Ser Trp Glu Ala Leu Arg
1 5 10 15

Arg Arg Arg Leu Arg Arg Arg Arg Leu
20 25

<210> SEQ ID NO 315
<211> LENGTH: 25
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Thick-Borne
Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(25)
<223> OTHER INFORMATION: ER cytosolic retention signal
Cell penetrating peptide

<400> SEQUENCE: 315

Gln Leu Val Ala Glu Trp Ser Gly Cys Val Glu Trp His Ala Leu Arg
1 5 10 15

Arg Arg Arg Leu Arg Arg Arg Arg Leu
20 25

<210> SEQ ID NO 316
<211> LENGTH: 24
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(12)
<223> OTHER INFORMATION: NS3pro activation inhibitor segment,
NS3pro N-terminal domain binding segment,
segment NS4A from HCV
<220> FEATURE:
<221> NAME/KEY: MOD_RES
<222> LOCATION: (13)

<223> OTHER INFORMATION: Linker residue beta-Alanine ; bAla
<220> FEATURE:
<221> NAME/KEY: DOMAIN
<222> LOCATION: (14)..(24)
<223> OTHER INFORMATION: ER cytosolic retention signal
Cell penetrating peptide

<400> SEQUENCE: 316

Thr Gly Ser Val Val Ile Val Gly Arg Ile Ile Leu Ala Leu Arg Arg
1 5 10 15

Arg Arg Leu Arg Arg Arg Arg Leu
20

<210> SEQ ID NO 317
<211> LENGTH: 24
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(12)
<223> OTHER INFORMATION: NS3pro activation inhibitor segment,
NS3pro N-terminal domain binding segment,
segment NS4A from HCV,
mutation of R28 by Q
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(24)
<223> OTHER INFORMATION: ER cytosolic retention signal
Cell penetrating peptide

<400> SEQUENCE: 317

Thr Gly Ser Val Val Ile Val Gly Gln Ile Ile Leu Ala Leu Arg Arg
1 5 10 15

Arg Arg Leu Arg Arg Arg Arg Leu
20

<210> SEQ ID NO 318
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: DISULFID
<222> LOCATION: (15)..(32)

<400> SEQUENCE: 318

Asp Leu Glu Leu Glu Arg Ala Ala Asp Val Lys Trp Glu Ala Cys Ser
1 5 10 15

Asn Ile Val Ile Gly Ile Gly Asp Lys Ala Leu Lys Ile Asn Trp Cys
20 25 30

<210> SEQ ID NO 319
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: DISULFID
<222> LOCATION: (15)..(32)

<400> SEQUENCE: 319

Asp Leu Ser Leu Glu Lys Ala Ala Glu Val Ser Trp Glu Ala Cys Ser
1 5 10 15

Asn Ile Val Ile Gly Ile Gly Asp Lys Ala Leu Lys Ile Asn Trp Cys
20 25 30

<210> SEQ ID NO 320
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: DISULFID
<222> LOCATION: (15)..(32)

<400> SEQUENCE: 320

Asp Leu Thr Val Glu Lys Ala Ala Asp Val Thr Trp Glu Ala Cys Ser
1 5 10 15

Asn Ile Val Ile Gly Ile Gly Asp Lys Ala Leu Lys Ile Asn Trp Cys
20 25 30

<210> SEQ ID NO 321
<211> LENGTH: 32
<212> TYPE: PRT
<213> ORGANISM: Artificial Sequence
<220> FEATURE:
<223> OTHER INFORMATION: Description of the Artificial Sequence:

chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: DISULFID
<222> LOCATION: (15)..(32)

<400> SEQUENCE: 321

Asp Leu Ser Leu Glu Lys Ala Ala Asn Val Gln Trp Asp Ala Cys Ser
1 5 10 15

Asn Ile Val Ile Gly Ile Gly Asp Lys Ala Leu Lys Ile Asn Trp Cys
20 25 30

<210> SEQ ID NO 322
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: DISULFID
<222> LOCATION: (15)..(32)

<400> SEQUENCE: 322

Asp Met Trp Ile Glu Arg Thr Ala Asp Ile Thr Trp Glu Ala Cys Ser
1 5 10 15

Asn Ile Val Ile Gly Ile Gly Asp Lys Ala Leu Lys Ile Asn Trp Cys
20 25 30

<210> SEQ ID NO 323
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the YFV
<220> FEATURE:
<221> NAME/KEY: MOD_RES
<222> LOCATION: (14)

```
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: DISULFID
<222> LOCATION: (15)..(32)

<400> SEQUENCE: 323

Gly Leu Glu Leu Lys Lys Leu Gly Glu Val Ser Trp Glu Ala Cys Ser
  1               5                  10                  15

Asn Ile Val Ile Gly Ile Gly Asp Lys Ala Leu Lys Ile Asn Trp Cys
             20                  25                  30


<210> SEQ ID NO 324
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Japanese Encephalitis
      virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: DISULFID
<222> LOCATION: (15)..(32)

<400> SEQUENCE: 324

Asp Met Trp Leu Glu Arg Ala Ala Asp Ile Ser Trp Glu Ala Cys Ser
  1               5                  10                  15

Asn Ile Val Ile Gly Ile Gly Asp Lys Ala Leu Lys Ile Asn Trp Cys
             20                  25                  30


<210> SEQ ID NO 325
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: DISULFID
```

<222> LOCATION: (15)..(32)

<400> SEQUENCE: 325

Gln Leu Val Ala Glu Trp Ser Gly Cys Val Glu Trp His Ala Cys Ser
1 5 10 15

Asn Ile Val Ile Gly Ile Gly Asp Lys Ala Leu Lys Ile Asn Trp Cys
20 25 30

<210> SEQ ID NO 326
<211> LENGTH: 31
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(12)
<223> OTHER INFORMATION: NS3pro activation inhibitor segment, NS3pro N-terminal domain binding segment, segment NS4A from HCV
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(31)
<223> OTHER INFORMATION: cell penetrating peptide based on the FG hairpin of domain III from the envelope protein of DV3
<220> FEATURE:
<221> NAME/KEY: DISULFID
<222> LOCATION: (14)..(31)

<400> SEQUENCE: 326

Thr Gly Ser Val Val Ile Val Gly Arg Ile Ile Leu Ala Cys Ser Asn
1 5 10 15

Ile Val Ile Gly Ile Gly Asp Lys Ala Leu Lys Ile Asn Trp Cys
20 25 30

<210> SEQ ID NO 327
<211> LENGTH: 31
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(12)
<223> OTHER INFORMATION: NS3pro activation inhibitor segment, NS3pro N-terminal domain binding segment, segment NS4A from HCV, mutation of R28 by Q
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(31)
<223> OTHER INFORMATION: cell penetrating peptide based on the FG hairpin of domain III from the envelope protein of DV3
<220> FEATURE:
<221> NAME/KEY: DISULFID
<222> LOCATION: (14)..(31)

<400> SEQUENCE: 327

Thr Gly Ser Val Val Ile Val Gly Gln Ile Ile Leu Ala Cys Ser Asn
1 5 10 15

Ile Val Ile Gly Ile Gly Asp Lys Ala Leu Lys Ile Asn Trp Cys
20 25 30

<210> SEQ ID NO 328
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 328

Asp Leu Glu Leu Glu Arg Ala Ala Asp Val Lys Trp Glu Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 329
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN

```
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (15)..(32)

<400> SEQUENCE: 329

Asp Leu Ser Leu Glu Lys Ala Ala Glu Val Ser Trp Glu Ala Cys Ser
  1               5                  10                  15

Asn Ile Val Ile Gly Ile Gly Asp Lys Ala Leu Lys Ile Asn Trp Cys
            20                  25                  30

Ala Leu Arg Arg Arg Arg Leu
        35


<210> SEQ ID NO 330
<211> LENGTH: 39
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (15)..(32)

<400> SEQUENCE: 330

Asp Leu Thr Val Glu Lys Ala Ala Asp Val Thr Trp Glu Ala Cys Ser
  1               5                  10                  15

Asn Ile Val Ile Gly Ile Gly Asp Lys Ala Leu Lys Ile Asn Trp Cys
            20                  25                  30

Ala Leu Arg Arg Arg Arg Leu
        35
```

<210> SEQ ID NO 331
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 331

```
Asp Leu Ser Leu Glu Lys Ala Ala Asn Val Gln Trp Asp Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu
         35
```

<210> SEQ ID NO 332
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)

<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 332

Asp Met Trp Ile Glu Arg Thr Ala Asp Ile Thr Trp Glu Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 333
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 333

Gly Leu Glu Leu Lys Lys Leu Gly Glu Val Ser Trp Glu Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 334
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 334

```
Asp Met Trp Leu Glu Arg Ala Ala Asp Ile Ser Trp Glu Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu
         35
```

<210> SEQ ID NO 335
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Thick-Borne
Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN

```
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (15)..(32)

<400> SEQUENCE: 335

Gln Leu Val Ala Glu Trp Ser Gly Cys Val Glu Trp His Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu
         35


<210> SEQ ID NO 336
<211> LENGTH: 38
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(31)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (32)
<223> OTHER INFORMATION: Linker residue beta-Alanine ; bAla
<220> FEATURE:
<221> NAME/KEY: SIGNAL
<222> LOCATION: (33)..(38)
<223> OTHER INFORMATION: ER cytosolic retention signal
      ER is the Endoplasmic Reticulum
<220> FEATURE:
<221> NAME/KEY: DISULFID
<222> LOCATION: (14)..(31)

<400> SEQUENCE: 336

Thr Gly Ser Val Val Ile Val Gly Arg Ile Ile Leu Ala Cys Ser Asn
  1               5                  10                  15

Ile Val Ile Gly Ile Gly Asp Lys Ala Leu Lys Ile Asn Trp Cys Ala
             20                  25                  30

Leu Arg Arg Arg Arg Leu
         35
```

```
<210> SEQ ID NO 337
<211> LENGTH: 38
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(12)
<223> OTHER INFORMATION: NS3pro activation inhibitor segment,
      NS3pro N-terminal domain binding segment,
      segment NS4A from HCV,
      mutation of R28 by Q
<220> FEATURE:
<221> NAME/KEY: MOD_RES
<222> LOCATION: (13)
<223> OTHER INFORMATION: Linker residue beta-Alanine ; bAla
<220> FEATURE:
<221> NAME/KEY: DOMAIN
<222> LOCATION: (14)..(31)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (32)
<223> OTHER INFORMATION: Linker residue beta-Alanine ; bAla
<220> FEATURE:
<221> NAME/KEY: SIGNAL
<222> LOCATION: (33)..(38)
<223> OTHER INFORMATION: ER cytosolic retention signal
      ER is the Endoplasmic Reticulum
<220> FEATURE:
<221> NAME/KEY: DISULFID
<222> LOCATION: (14)..(31)

<400> SEQUENCE: 337

Thr Gly Ser Val Val Ile Val Gly Gln Ile Ile Leu Ala Cys Ser Asn
  1               5                  10                  15

Ile Val Ile Gly Ile Gly Asp Lys Ala Leu Lys Ile Asn Trp Cys Ala
             20                  25                  30

Leu Arg Arg Arg Arg Leu
         35


<210> SEQ ID NO 338
<211> LENGTH: 43
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
```

<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: SIGNAL
<222> LOCATION: (40)..(43)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 338

Asp Leu Glu Leu Glu Arg Ala Ala Asp Val Lys Trp Glu Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu Lys Asp Glu Leu
35 40

<210> SEQ ID NO 339
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: DISULFID
<222> LOCATION: (15)..(32)

<400> SEQUENCE: 339

Ser Ser Pro Ile Leu Ser Ile Thr Ile Ser Glu Asp Gly Ala Cys Ser
1 5 10 15

Asn Ile Val Ile Gly Ile Gly Asp Lys Ala Leu Lys Ile Asn Trp Cys
20 25 30

<210> SEQ ID NO 340
<211> LENGTH: 32
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment, -continued

```
      NS3pro C-terminal domain binding segment,
      segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: DISULFID
<222> LOCATION: (15)..(32)

<400> SEQUENCE: 340

Ala Ser His Asn Ile Leu Val Glu Val Gln Asp Asp Gly Ala Cys Ser
  1               5                  10                  15

Asn Ile Val Ile Gly Ile Gly Asp Lys Ala Leu Lys Ile Asn Trp Cys
             20                  25                  30


<210> SEQ ID NO 341
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: DISULFID
<222> LOCATION: (15)..(32)

<400> SEQUENCE: 341

Val Ser His Asn Leu Met Ile Thr Val Asp Asp Asp Gly Ala Cys Ser
  1               5                  10                  15

Asn Ile Val Ile Gly Ile Gly Asp Lys Ala Leu Lys Ile Asn Trp Cys
             20                  25                  30


<210> SEQ ID NO 342
<211> LENGTH: 32
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
```

hairpin of domain III from the envelope protein of DV3
<220> FEATURE:
<221> NAME/KEY: DISULFID
<222> LOCATION: (15)..(32)

<400> SEQUENCE: 342

Ser Ser Pro Ile Ile Glu Val Lys Gln Asp Glu Asp Gly Ala Cys Ser
1 5 10 15

Asn Ile Val Ile Gly Ile Gly Asp Lys Ala Leu Lys Ile Asn Trp Cys
20 25 30

<210> SEQ ID NO 343
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: DISULFID
<222> LOCATION: (15)..(32)

<400> SEQUENCE: 343

Ser Ser Ala Arg Tyr Asp Val Ala Leu Ser Glu Gln Gly Ala Cys Ser
1 5 10 15

Asn Ile Val Ile Gly Ile Gly Asp Lys Ala Leu Lys Ile Asn Trp Cys
20 25 30

<210> SEQ ID NO 344
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Japanese Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: DISULFID
<222> LOCATION: (15)..(32)

<400> SEQUENCE: 344

Ser Ser Arg Arg Leu Asp Val Lys Leu Asp Asp Asp Gly Ala Cys Ser
1 5 10 15

Asn Ile Val Ile Gly Ile Gly Asp Lys Ala Leu Lys Ile Asn Trp Cys
20 25 30

<210> SEQ ID NO 345
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the Thick-Borne Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: DISULFID
<222> LOCATION: (15)..(32)

<400> SEQUENCE: 345

Gly Glu Val Ser Leu Arg Val Arg Gln Asp Ala Met Gly Ala Cys Ser
1 5 10 15

Asn Ile Val Ile Gly Ile Gly Asp Lys Ala Leu Lys Ile Asn Trp Cys
20 25 30

<210> SEQ ID NO 346
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro C-terminal domain binding segment, segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: DISULFID
<222> LOCATION: (15)..(32)

<400> SEQUENCE: 346

Ser Ser Glu Arg Val Asp Val Arg Leu Asp Asp Asp Gly Ala Cys Ser
1 5 10 15

Asn Ile Val Ile Gly Ile Gly Asp Lys Ala Leu Lys Ile Asn Trp Cys
20 25 30

<210> SEQ ID NO 347
<211> LENGTH: 39
<212> TYPE: PRT
<213> ORGANISM: Artificial Sequence

```
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (15)..(32)

<400> SEQUENCE: 347

Ser Ser Pro Ile Leu Ser Ile Thr Ile Ser Glu Asp Gly Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu
         35


<210> SEQ ID NO 348
<211> LENGTH: 39
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
```

<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 348

Ala Ser His Asn Ile Leu Val Glu Val Gln Asp Asp Gly Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 349
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE ; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 349

Val Ser His Asn Leu Met Ile Thr Val Asp Asp Asp Gly Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 350
<211> LENGTH: 39
<212> TYPE: PRT
<213> ORGANISM: Artificial Sequence
<220> FEATURE:

<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the virus dengue 4
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (15)..(32)

<400> SEQUENCE: 350

Ser Ser Pro Ile Ile Glu Val Lys Gln Asp Glu Asp Gly Ala Cys Ser
1               5                   10                  15

Asn Ile Val Ile Gly Ile Gly Asp Lys Ala Leu Lys Ile Asn Trp Cys
            20                  25                  30

Ala Leu Arg Arg Arg Arg Leu
        35

<210> SEQ ID NO 351
<211> LENGTH: 39
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 351

Ser Ser Ala Arg Tyr Asp Val Ala Leu Ser Glu Gln Gly Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 352
<211> LENGTH: 39
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 352

Ser Ser Arg Arg Leu Asp Val Lys Leu Asp Asp Asp Gly Ala Cys Ser
1 5 10 15

Asn Ile Val Ile Gly Ile Gly Asp Lys Ala Leu Lys Ile Asn Trp Cys
20 25 30

Ala Leu Arg Arg Arg Arg Leu
35

<210> SEQ ID NO 353
<211> LENGTH: 39
<212> TYPE: PRT
<213> ORGANISM: Artificial Sequence
<220> FEATURE:

```
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the Thick-Borne
      Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
      ER is the Endoplasmic Reticulum
<220> FEATURE:
<221> NAME/KEY: DISULFID
<222> LOCATION: (15)..(32)

<400> SEQUENCE: 353

Gly Glu Val Ser Leu Arg Val Arg Gln Asp Ala Met Gly Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu
         35


<210> SEQ ID NO 354
<211> LENGTH: 39
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: LIPID
<222> LOCATION: (1)
<223> OTHER INFORMATION: MYRISTATE ; MYRISTATE bound to the N terminal
      end of the chimerical peptide
      PALMITATE could also be used
<220> FEATURE:
<221> NAME/KEY: DOMAIN
<222> LOCATION: (1)..(13)
<223> OTHER INFORMATION: NS3pro activation inhibitor segment,
      NS3pro C-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)
```

<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: DISULFID
<222> LOCATION: (15)..(32)

<400> SEQUENCE: 354

```
Ser Ser Glu Arg Val Asp Val Arg Leu Asp Asp Asp Gly Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu
         35
```

<210> SEQ ID NO 355
<211> LENGTH: 43
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: LIPID
<222> LOCATION: (1)
<223> OTHER INFORMATION: MYRISTATE; MYRISTATE bound to the N terminal
end of the chimerical peptide
PALMITATE could also be used
<220> FEATURE:
<221> NAME/KEY: DOMAIN
<222> LOCATION: (1)..(13)
<223> OTHER INFORMATION: NS3pro activation inhibitor segment,
NS3pro C-terminal domain binding segment,
segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)
<223> OTHER INFORMATION: Linker residue beta-Alanine ; bAla
<220> FEATURE:
<221> NAME/KEY: SIGNAL
<222> LOCATION: (34)..(39)
<223> OTHER INFORMATION: ER cytosolic retention signal
ER is the Endoplasmic Reticulum
<220> FEATURE:
<221> NAME/KEY: SIGNAL
<222> LOCATION: (40)..(43)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 355

```
Ser Ser Pro Ile Leu Ser Ile Thr Ile Ser Glu Asp Gly Ala Cys Ser
  1               5                  10                  15

Asn Ile Val Ile Gly Ile Gly Asp Lys Ala Leu Lys Ile Asn Trp Cys
             20                  25                  30

Ala Leu Arg Arg Arg Arg Leu Lys Asp Glu Leu
         35                  40
```

<210> SEQ ID NO 356
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus DV2
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 356

Asp Leu Glu Leu Glu Arg Ala Ala Asp Val Lys Trp Glu Ala Cys Ser
1 5 10 15

Asn Ile Val Ile Gly Ile Gly Asp Lys Ala Leu Lys Ile Asn Trp Cys
20 25 30

Ala Ala Lys Asp Glu Leu
35

<210> SEQ ID NO 357
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 1
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:

<223> OTHER INFORMATION: Carboxylic C-terminal end
<220> FEATURE:
<221> NAME/KEY: DISULFID
<222> LOCATION: (15)..(32)

<400> SEQUENCE: 357

Asp Leu Ser Leu Glu Lys Ala Ala Glu Val Ser Trp Glu Ala Cys Ser
1 5 10 15

Asn Ile Val Ile Gly Ile Gly Asp Lys Ala Leu Lys Ile Asn Trp Cys
20 25 30

Ala Ala Lys Asp Glu Leu
35

<210> SEQ ID NO 358
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 3
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 358

Asp Leu Thr Val Glu Lys Ala Ala Asp Val Thr Trp Glu Ala Cys Ser
1 5 10 15

Asn Ile Val Ile Gly Ile Gly Asp Lys Ala Leu Lys Ile Asn Trp Cys
20 25 30

Ala Ala Lys Asp Glu Leu
35

<210> SEQ ID NO 359
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the virus dengue 4
<220> FEATURE:
<221> NAME/KEY: MOD_RES

```
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 359

Asp Leu Ser Leu Glu Lys Ala Ala Asn Val Gln Trp Asp Ala Cys Ser
1               5                   10                  15

Asn Ile Val Ile Gly Ile Gly Asp Lys Ala Leu Lys Ile Asn Trp Cys
            20                  25                  30

Ala Ala Lys Asp Glu Leu
        35


<210> SEQ ID NO 360
<211> LENGTH: 38
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<221> NAME/KEY: DOMAIN
<222> LOCATION: (1)..(13)
<223> OTHER INFORMATION: NS3pro activation inhibitor segment,
      NS3pro N-terminal domain binding segment,
      segment of NS2B from the WNV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
      hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 360

Asp Met Trp Ile Glu Arg Thr Ala Asp Ile Thr Trp Glu Ala Cys Ser
1               5                   10                  15

Asn Ile Val Ile Gly Ile Gly Asp Lys Ala Leu Lys Ile Asn Trp Cys
            20                  25                  30

Ala Ala Lys Asp Glu Leu
        35
```

<210> SEQ ID NO 361
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the YFV
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 361

Gly Leu Glu Leu Lys Lys Leu Gly Glu Val Ser Trp Glu Ala Cys Ser
1 5 10 15

Asn Ile Val Ile Gly Ile Gly Asp Lys Ala Leu Lys Ile Asn Trp Cys
20 25 30

Ala Ala Lys Asp Glu Leu
35

<210> SEQ ID NO 362
<211> LENGTH: 38
<212> TYPE: PRT
<213> ORGANISM: Artificial Sequence
<220> FEATURE:
<223> OTHER INFORMATION: Description of the Artificial Sequence:
chimerical peptide
<220> FEATURE:
<221> NAME/KEY: DOMAIN
<222> LOCATION: (1)..(13)
<223> OTHER INFORMATION: NS3pro activation inhibitor segment,
NS3pro N-terminal domain binding segment,
segment of NS2B from the Japanese Encephalitis
virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG
hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 362

```
Asp Met Trp Leu Glu Arg Ala Ala Asp Ile Ser Trp Glu Ala Cys Ser
  1               5                  10                  15

Asn Ile Val Ile Gly Ile Gly Asp Lys Ala Leu Lys Ile Asn Trp Cys
            20                  25                  30

Ala Ala Lys Asp Glu Leu
        35
```

<210> SEQ ID NO 363
<211> LENGTH: 38
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(13)
<223> OTHER INFORMATION: NS3pro activation inhibitor segment, NS3pro N-terminal domain binding segment, segment of NS2B from the Thick-Borne Encephalitis virus
<220> FEATURE:
<221> NAME/KEY: MOD_RES
<222> LOCATION: (14)
<223> OTHER INFORMATION: Linker residue beta-Alanine ; bAla
<220> FEATURE:
<221> NAME/KEY: DOMAIN
<222> LOCATION: (15)..(32)
<223> OTHER INFORMATION: cell penetrating peptide based on the FG hairpin of domain III from the envelope protein of DV3
<220> FEATURE:
<221> NAME/KEY: MOD_RES
<222> LOCATION: (33)..(34)
<223> OTHER INFORMATION: Linker residue beta-Alanine ; bAla
<220> FEATURE:
<221> NAME/KEY: SIGNAL
<222> LOCATION: (35)..(38)
<223> OTHER INFORMATION: ER Retention signal KDEL
<220> FEATURE:
<223> OTHER INFORMATION: Carboxylic C-terminal end
<220> FEATURE:
<221> NAME/KEY: DISULFID
<222> LOCATION: (15)..(32)

<400> SEQUENCE: 363

```
Gln Leu Val Ala Glu Trp Ser Gly Cys Val Glu Trp His Ala Cys Ser
  1               5                  10                  15

Asn Ile Val Ile Gly Ile Gly Asp Lys Ala Leu Lys Ile Asn Trp Cys
            20                  25                  30

Ala Ala Lys Asp Glu Leu
        35
```

<210> SEQ ID NO 364
<211> LENGTH: 32
<212> TYPE: PRT
<213> ORGANISM: Artificial Sequence
<220> FEATURE:
<223> OTHER INFORMATION: Description of the Artificial Sequence: chimerical peptide
<220> FEATURE:
<221> NAME/KEY: DOMAIN
<222> LOCATION: (1)..(10)
<223> OTHER INFORMATION: cell penetrating peptide R10
<220> FEATURE:
<221> NAME/KEY: DOMAIN

```
<222> LOCATION: (11)..(13)
<223> OTHER INFORMATION: linker segment
<220> FEATURE:
<221> NAME/KEY: DOMAIN
<222> LOCATION: (14)..(26)
<223> OTHER INFORMATION: NS3pro activation inhibitor segment,
      NS3pro C-terminal domain binding segment,
      segment of NS2B from the virus DV2
<220> FEATURE:
<221> NAME/KEY: DOMAIN
<222> LOCATION: (27)..(28)
<223> OTHER INFORMATION: linker segment
<220> FEATURE:
<221> NAME/KEY: SIGNAL
<222> LOCATION: (29)..(32)
<223> OTHER INFORMATION: ER Retention signal KDEL
<220> FEATURE:
<223> OTHER INFORMATION: Carboxylic C-terminal end

<400> SEQUENCE: 364

Arg Arg Arg Arg Arg Arg Arg Arg Arg Arg Gly Gly Gly Ser Ser Pro
  1               5                   10                  15

Ile Leu Ser Ile Thr Ile Ser Glu Asp Gly Gly Gly Lys Asp Glu Leu
            20                  25                  30


<210> SEQ ID NO 365
<211> LENGTH: 11
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<223> OTHER INFORMATION: cell penetrating peptide; designed

<400> SEQUENCE: 365

Leu Arg Arg Arg Arg Leu Arg Arg Arg Arg Leu
  1               5                   10


<210> SEQ ID NO 366
<211> LENGTH: 12
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<223> OTHER INFORMATION: cell penetrating peptide; designed
<220> FEATURE:
<221> NAME/KEY: MOD_RES
<222> LOCATION: (7)
<223> OTHER INFORMATION: Linker residue beta-Alanine; bAla

<400> SEQUENCE: 366

Leu Arg Arg Arg Arg Leu Ala Arg Arg Arg Arg Leu
  1               5                   10


<210> SEQ ID NO 367
<211> LENGTH: 6
<212> TYPE: PRT
<213> ORGANISM: Artificial Sequence
<220> FEATURE:
<223> OTHER INFORMATION: Description of the Artificial Sequence:
      T segment ER retention signal

<400> SEQUENCE: 367

Leu Arg Arg Arg Arg Leu
  1               5


<210> SEQ ID NO 368
<211> LENGTH: 10
```

```
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<223> OTHER INFORMATION: ER retention signal; designed
<220> FEATURE:
<221> NAME/KEY: SIGNAL
<222> LOCATION: (1)..(6)
<223> OTHER INFORMATION: ER cytosolic retention signal
      ER is the Endoplasmic Reticulum
<220> FEATURE:
<221> NAME/KEY: SIGNAL
<222> LOCATION: (7)..(10)
<223> OTHER INFORMATION: ER Retention signal KDEL

<400> SEQUENCE: 368

Leu Arg Arg Arg Arg Leu Lys Asp Glu Leu
  1               5                  10


<210> SEQ ID NO 369
<211> LENGTH: 13
<212> TYPE: PRT
<213> ORGANISM: Artificial Sequence
<220> FEATURE:
<223> OTHER INFORMATION: Description of the Artificial Sequence:
      chimerical peptide
<220> FEATURE:
<223> OTHER INFORMATION: inhibitory I segment; designed

<400> SEQUENCE: 369

Gln Trp Pro Ala Leu Pro Lys Ile Glu Ala Gln Asp Gly
  1               5                  10


<210> SEQ ID NO 370
<211> LENGTH: 130
<212> TYPE: PRT
<213> ORGANISM: Dengue virus Type 2

<400> SEQUENCE: 370

Ser Trp Pro Leu Asn Glu Ala Ile Met Ala Val Gly Met Val Ser Ile
  1               5                  10                  15

Leu Ala Ser Ser Leu Leu Lys Asn Asp Ile Pro Met Thr Gly Pro Leu
             20                  25                  30

Val Ala Gly Gly Leu Leu Thr Val Cys Tyr Val Leu Thr Gly Arg Ser
         35                  40                  45

Ala Asp Leu Glu Leu Glu Arg Ala Ala Asp Val Lys Trp Glu Asp Gln
     50                  55                  60

Ala Glu Ile Ser Gly Ser Ser Pro Ile Leu Ser Ile Thr Ile Ser Glu
 65                  70                  75                  80

Asp Gly Ser Met Ser Ile Lys Asn Glu Glu Glu Glu Gln Thr Leu Thr
                 85                  90                  95

Ile Leu Ile Arg Thr Gly Leu Leu Val Ile Ser Gly Val Phe Pro Val
            100                 105                 110

Ser Ile Pro Ile Thr Ala Ala Ala Trp Tyr Leu Trp Glu Val Lys Lys
        115                 120                 125

Gln Arg
    130


<210> SEQ ID NO 371
<211> LENGTH: 130
<212> TYPE: PRT
<213> ORGANISM: Dengue virus Type 3

<400> SEQUENCE: 371
```

Ser Trp Pro Leu Asn Glu Gly Val Met Ala Val Gly Leu Val Ser Ile
1 5 10 15

Leu Ala Ser Ser Leu Leu Arg Asn Asp Val Pro Met Ala Gly Pro Leu
20 25 30

Val Ala Gly Gly Leu Leu Ile Ala Cys Tyr Val Ile Thr Gly Thr Ser
35 40 45

Ala Asp Leu Thr Val Glu Lys Ala Ala Asp Val Thr Trp Glu Glu Glu
50 55 60

Ala Glu Gln Thr Gly Val Ser His Asn Leu Met Ile Thr Val Asp Asp
65 70 75 80

Asp Gly Thr Met Arg Ile Lys Asp Asp Glu Thr Glu Asn Ile Leu Thr
85 90 95

Val Leu Leu Lys Thr Ala Leu Leu Ile Val Ser Gly Ile Phe Pro Tyr
100 105 110

Ser Ile Pro Ala Thr Met Leu Val Trp His Thr Trp Gln Lys Gln Thr
115 120 125

Gln Arg
130

<210> SEQ ID NO 372
<211> LENGTH: 130
<212> TYPE: PRT
<213> ORGANISM: Dengue virus Type 1S

<400> SEQUENCE: 372

Ser Trp Pro Leu Asn Glu Gly Ile Met Ala Val Gly Ile Val Ser Ile
1 5 10 15

Leu Leu Ser Ser Leu Leu Lys Asn Asp Val Pro Leu Ala Gly Pro Leu
20 25 30

Ile Ala Gly Gly Met Leu Ile Ala Cys Tyr Val Ile Ser Gly Ser Ser
35 40 45

Ala Asp Leu Ser Leu Glu Lys Ala Ala Glu Val Ser Trp Glu Glu Glu
50 55 60

Ala Glu His Ser Gly Ala Ser His Asn Ile Leu Val Glu Val Gln Asp
65 70 75 80

Asp Gly Thr Met Lys Ile Lys Asp Glu Glu Arg Asp Asp Thr Leu Thr
85 90 95

Ile Leu Leu Lys Ala Thr Leu Leu Ala Val Ser Gly Val Tyr Pro Leu
100 105 110

Ser Ile Pro Ala Thr Leu Phe Val Trp Tyr Phe Trp Gln Lys Lys Lys
115 120 125

Gln Arg
130

<210> SEQ ID NO 373
<211> LENGTH: 130
<212> TYPE: PRT
<213> ORGANISM: Dengue virus Type 4

<400> SEQUENCE: 373

Ser Trp Pro Leu Asn Glu Gly Ile Met Ala Val Gly Leu Val Ser Leu
1 5 10 15

Leu Gly Ser Ala Leu Leu Lys Asn Asp Val Pro Leu Ala Gly Pro Met
20 25 30

Val Ala Gly Gly Leu Leu Leu Ala Ala Tyr Met Met Ser Gly Ser Ser
35 40 45

```
Ala Asp Leu Ser Leu Glu Lys Ala Ala Asn Val Gln Trp Asp Glu Met
     50                  55                  60

Ala Asp Ile Thr Gly Ser Ser Pro Ile Ile Glu Val Lys Gln Asp Glu
 65                  70                  75                  80

Asp Gly Ser Phe Ser Ile Arg Asp Val Glu Glu Thr Asn Met Ile Thr
                 85                  90                  95

Leu Leu Val Lys Leu Ala Leu Ile Thr Val Ser Gly Leu Tyr Pro Leu
            100                 105                 110

Ala Ile Pro Val Thr Met Thr Leu Trp Tyr Met Trp Gln Val Lys Thr
        115                 120                 125

Gln Arg
    130


<210> SEQ ID NO 374
<211> LENGTH: 129
<212> TYPE: PRT
<213> ORGANISM: Murray Valley Encephalitis virus

<400> SEQUENCE: 374

Trp Pro Ala Thr Glu Val Leu Thr Ala Val Gly Leu Met Phe Ala Ile
  1               5                  10                  15

Val Gly Gly Leu Ala Glu Leu Asp Ile Ser Met Ser Val Pro Phe Thr
             20                  25                  30

Ile Ala Gly Leu Met Leu Val Ser Tyr Val Ile Ser Gly Lys Ala Thr
         35                  40                  45

Asp Met Trp Leu Glu Arg Ala Ala Asp Val Ser Trp Glu Ala Gly Ala
     50                  55                  60

Ala Ile Thr Gly Thr Ser Glu Arg Leu Asp Val Gln Leu Asp Asp Asp
 65                  70                  75                  80

Gly Asp Phe His Leu Leu Asn Asp Pro Gly Val Pro Trp Lys Ile Trp
                 85                  90                  95

Val Leu Arg Met Thr Cys Leu Ser Val Ala Ala Ile Thr Pro Trp Ala
            100                 105                 110

Ile Leu Pro Ser Ala Phe Gly Tyr Trp Leu Thr Leu Lys Tyr Thr Lys
        115                 120                 125

Arg
130


<210> SEQ ID NO 375
<211> LENGTH: 130
<212> TYPE: PRT
<213> ORGANISM: Yellow Fever virus 2

<400> SEQUENCE: 375

Ser Ile Pro Val Asn Glu Ala Leu Ala Ala Ala Gly Leu Val Gly Val
  1               5                  10                  15

Leu Ala Gly Leu Ala Phe Gln Glu Met Glu Asn Phe Leu Gly Pro Ile
             20                  25                  30

Ala Val Gly Gly Leu Leu Met Met Leu Val Ser Val Ala Gly Arg Val
         35                  40                  45

Asp Gly Leu Glu Leu Lys Lys Leu Gly Glu Val Ser Trp Glu Glu Glu
     50                  55                  60

Ala Glu Ile Ser Gly Ser Ser Ala Arg Tyr Asp Val Ala Leu Ser Glu
 65                  70                  75                  80

Gln Gly Glu Phe Lys Leu Leu Ser Glu Glu Lys Val Pro Trp Asp Gln
                 85                  90                  95
```

```
Val Val Met Thr Ser Leu Ala Leu Val Gly Ala Ala Leu His Pro Phe
            100                 105                 110

Ala Leu Leu Leu Val Leu Ala Gly Trp Leu Phe His Val Arg Gly Ala
        115                 120                 125

Arg Arg
    130


<210> SEQ ID NO 376
<211> LENGTH: 130
<212> TYPE: PRT
<213> ORGANISM: Yellow Fever virus 1

<400> SEQUENCE: 376

Ser Ile Pro Val Asn Glu Ala Leu Ala Ala Ala Gly Leu Val Gly Val
  1               5                  10                  15

Leu Ala Gly Leu Ala Phe Gln Glu Met Glu Asn Phe Leu Gly Pro Ile
             20                  25                  30

Ala Val Gly Gly Leu Leu Met Met Leu Val Ser Val Ala Gly Arg Val
         35                  40                  45

Asp Gly Leu Glu Leu Lys Lys Leu Gly Glu Val Ser Trp Glu Glu Glu
     50                  55                  60

Ala Glu Ile Ser Gly Ser Ser Ala Arg Tyr Asp Val Ala Leu Ser Glu
 65                  70                  75                  80

Gln Gly Glu Phe Lys Leu Leu Ser Glu Glu Lys Val Pro Trp Asp Gln
                 85                  90                  95

Val Val Met Thr Ser Leu Ala Leu Val Gly Ala Ala Leu His Pro Phe
            100                 105                 110

Ala Leu Leu Leu Val Leu Ala Gly Trp Leu Phe His Val Arg Gly Ala
        115                 120                 125

Arg Arg
    130


<210> SEQ ID NO 377
<211> LENGTH: 130
<212> TYPE: PRT
<213> ORGANISM: Saint Louis encephalitis virus

<400> SEQUENCE: 377

Ser Trp Pro Ala Ser Glu Val Leu Thr Gly Val Gly Leu Met Cys Ala
  1               5                  10                  15

Leu Ala Gly Gly Leu Leu Glu Glu Glu Thr Ser Met Val Val Pro Phe
             20                  25                  30

Ala Ile Ala Gly Leu Met Tyr Ile Thr Tyr Thr Val Ser Gly Lys Ala
         35                  40                  45

Ala Glu Met Trp Ile Glu Lys Ala Ala Asp Ile Thr Trp Glu Gln Asn
     50                  55                  60

Ala Glu Ile Thr Gly Thr Ser Pro Arg Leu Asp Val Asp Leu Asp Ser
 65                  70                  75                  80

His Gly Asn Phe Lys Leu Leu Asn Asp Pro Gly Ala Pro Val His Leu
                 85                  90                  95

Phe Ala Leu Arg Phe Ile Leu Leu Gly Leu Ser Ala Arg Phe His Trp
            100                 105                 110

Phe Ile Pro Phe Gly Val Leu Gly Phe Trp Leu Leu Gly Lys His Ser
        115                 120                 125

Lys Arg
    130
```

<210> SEQ ID NO 378
<211> LENGTH: 129
<212> TYPE: PRT
<213> ORGANISM: Japanese encephalitis virus 1

<400> SEQUENCE: 378

Trp Pro Ala Thr Glu Phe Leu Ser Ala Val Gly Leu Met Phe Ala Ile
1 5 10 15

Val Gly Gly Leu Ala Glu Leu Asp Ile Ser Met Ser Ile Pro Phe Met
20 25 30

Leu Ala Gly Leu Met Ala Val Ser Tyr Val Val Ser Gly Lys Ala Thr
35 40 45

Asp Met Trp Leu Glu Arg Ala Ala Asp Ile Ser Trp Glu Met Asp Ala
50 55 60

Ala Ile Thr Gly Ser Ser Arg Arg Leu Asp Val Lys Leu Asp Asp Asp
65 70 75 80

Gly Asp Phe His Leu Ile Asp Asp Pro Gly Val Pro Trp Lys Val Trp
85 90 95

Val Leu Arg Met Ser Cys Ile Gly Leu Ala Ala Leu Thr Pro Trp Ala
100 105 110

Ile Val Pro Ala Ala Phe Gly Tyr Trp Leu Thr Leu Lys Thr Thr Lys
115 120 125

Arg
130

<210> SEQ ID NO 379
<211> LENGTH: 129
<212> TYPE: PRT
<213> ORGANISM: Japanese encephalitis virus N

<400> SEQUENCE: 379

Trp Pro Ala Thr Glu Phe Leu Ser Ala Val Gly Leu Met Phe Ala Ile
1 5 10 15

Val Gly Gly Leu Ala Glu Leu Asp Ile Ser Met Ser Ile Pro Phe Met
20 25 30

Leu Ala Gly Leu Met Ala Val Ser Tyr Val Val Ser Gly Lys Ala Thr
35 40 45

Asp Met Trp Leu Glu Arg Ala Ala Asp Ile Ser Trp Glu Met Asp Ala
50 55 60

Ala Ile Thr Gly Ser Ser Arg Arg Leu Asp Val Lys Leu Asp Asp Asp
65 70 75 80

Gly Asp Phe His Leu Ile Asp Asp Pro Gly Val Pro Trp Lys Val Trp
85 90 95

Val Leu Arg Met Ser Cys Ile Gly Leu Ala Ala Leu Thr Pro Trp Ala
100 105 110

Ile Val Pro Ala Ala Phe Gly Tyr Trp Leu Thr Leu Lys Thr Thr Lys
115 120 125

Arg
130

<210> SEQ ID NO 380
<211> LENGTH: 129
<212> TYPE: PRT
<213> ORGANISM: Kunjin virus

<400> SEQUENCE: 380

Trp Pro Ala Thr Glu Val Met Thr Ala Val Gly Leu Met Phe Ala Ile
1 5 10 15

Val Gly Gly Leu Ala Glu Leu Asp Ile Ser Met Ala Ile Pro Met Thr
20 25 30

Ile Ala Gly Leu Met Phe Ala Ala Phe Val Ile Ser Gly Lys Ser Thr
35 40 45

Asp Met Trp Ile Glu Arg Thr Ala Asp Ile Ser Trp Glu Gly Asp Ala
50 55 60

Glu Ile Thr Gly Ser Ser Glu Arg Val Asp Val Arg Leu Asp Asp Asp
65 70 75 80

Gly Asn Phe Gln Leu Met Asn Asp Pro Gly Ala Pro Trp Lys Ile Trp
85 90 95

Met Leu Arg Met Ala Cys Leu Ala Ile Ser Ala Tyr Thr Pro Trp Ala
100 105 110

Ile Leu Pro Ser Val Val Gly Phe Trp Ile Thr Leu Gln Tyr Thr Lys
115 120 125

Arg
130

<210> SEQ ID NO 381
<211> LENGTH: 129
<212> TYPE: PRT
<213> ORGANISM: West Nile virus virus

<400> SEQUENCE: 381

Trp Pro Ala Thr Glu Val Met Thr Ala Val Gly Leu Met Phe Ala Ile
1 5 10 15

Val Gly Gly Leu Ala Glu Leu Asp Ile Ser Met Ala Ile Pro Met Thr
20 25 30

Ile Ala Gly Leu Met Phe Ala Ala Phe Val Ile Ser Gly Lys Ser Thr
35 40 45

Asp Met Trp Ile Glu Arg Thr Ala Asp Ile Thr Trp Glu Ser Asp Ala
50 55 60

Glu Ile Thr Gly Ser Ser Glu Arg Val Asp Val Arg Leu Asp Asp Asp
65 70 75 80

Gly Asn Phe Gln Leu Met Asn Asp Pro Gly Ala Pro Trp Lys Ile Trp
85 90 95

Met Leu Arg Met Ala Cys Leu Ala Ile Ser Ala Tyr Thr Pro Trp Ala
100 105 110

Ile Leu Pro Ser Val Ile Gly Phe Trp Ile Thr Leu Gln Tyr Thr Lys
115 120 125

Arg
130

<210> SEQ ID NO 382
<211> LENGTH: 126
<212> TYPE: PRT
<213> ORGANISM: Powasan virus

<400> SEQUENCE: 382

Arg Arg Ser Leu Ser Glu Pro Leu Thr Val Val Gly Val Met Leu Ala
1 5 10 15

Met Ala Ser Gly Leu Leu Arg His Ser Ser Glu Ala Leu Leu Ala Leu
20 25 30

Ser Ala Gly Ser Phe Leu Ile Leu Met Leu Ile Leu Gly Thr Arg Arg
35 40 45

-continued

```
Leu Gln Leu Thr Ala Glu Trp Ala Gly Val Val Glu Trp Asn Pro Glu
     50                  55                  60

Leu Val Asn Glu Gly Gly Glu Val Ser Leu Lys Val Arg Gln Asp Ala
 65                  70                  75                  80

Met Gly Asn Leu His Leu Thr Glu Val Glu Arg Glu Glu Arg Arg Leu
                 85                  90                  95

Ala Leu Trp Leu Val Phe Gly Leu Leu Ala Ser Ala Tyr His Trp Ser
            100                 105                 110

Gly Ile Leu Val Thr Met Gly Ala Trp Thr Val Tyr Glu Leu
        115                 120                 125
```

The invention claimed is:

1. A chimerical peptide having a primary structure $$[P]-[L_1]-[I]-[L_2]-[T] \text{ or } [I]-[L_3]-[P]-[P]-[L_4]-[T],$$

wherein [P] is a cell penetrating peptide, $[L_1]$-$[L_2]$-$[L_3]$ and $[L_4]$ are linker sequences of 0-6 amino acids,

[I] is an NS3pro activation inhibitor sequence which binds with at least one amino acid from the beta strands B2a and B2b of the C-terminal beta barrel or from the beta strand Al of the N-terminal beta barrel of the NS3pro protein from a virus of the Flaviviradae family,

[T] is an amino acid sequence between 0-10 residues capable of binding to a P1 and P2 substrate binding sites of the NS3pro protease from a virus of the Flaviviradae family, wherein said chimeric peptide is selected from the group consisting of SEQ ID NOS: 1-62 and 65-364, and wherein said peptide is able to inhibit or attenuate the infection by the virus.

2. The peptide according to the claim 1, wherein said inhibitor sequence is a peptide able to bind to NS3pro and contacts at least one residue comprised in the region Gly21-Lys28 of the N-terminal domain of the NS3pro protein from DV2 or structurally equivalent residues of the NS3pro protein from other Flavivirus.

3. The chimerical peptide according to the claim 1, wherein said inhibitor sequence is a peptide able to bind to NS3pro and contacts at least one residue comprised in the region Gly114-Thr118, Ser127 and Val162 of the C-terminal domain of the NS3pro protein from DV2 or structurally equivalent residues of the NS3pro protein from other Flavivirus.

4. The chimerical peptide according to the claim 1, wherein said inhibitor sequence contacts at least one residue comprised in the region Glu32-Thr38 of the N-terminal domain of the NS3pro protein from HCV or structurally equivalent residues of the NS3pro protein from other Hepacivirus.

5. The chimerical peptide according to the claim 1, wherein said inhibitor sequence includes region Asp50-Glu62 of the NS2B protein from DV2 or a structurally equivalent segment of the protein NS2B from other Flavivirus.

6. The chimerical peptide according to the claim 1 wherein said inhibitor sequence includes NS3pro protease which comprise the region Ser70-Gly82 of the NS2B protein from DV2 or a structurally equivalent segment of the protein NS2B from other Flavivirus.

7. The chimerical peptide according to the claim 1, wherein said inhibitor sequence includes region Thr20-Leu31 of the NS4A protein from HCV or a structurally equivalent segment of the protein NS4A from other Hepacivirus.

8. The chimerical peptide according to the claim 1, wherein said virus from the Flaviviridae family is one of the following Flavivirus: West Nile virus, St Louis Encephalitis virus, DV1, DV2, DV3, DV4, Japanese Encephalitis virus, Yellow Fever virus, Kunjin virus, Kyasanur Forest Disease virus, Tick-borne Encephalitis virus, Murray Valley virus, LANGAT virus, Louping ill virus, or Powassan virus.

9. The chimerical peptide according to the claim 1, wherein said virus from the Flaviviridae family is a Hepacivirus.

10. The chimerical peptide according to the claim 1, wherein said cell penetrating peptide is selected from one of the following cationic protein transduction domains: TAT peptide, heptaarginine, octaarginine, nonaarginine, decaarginine, or a peptide identified as SEQ ID NO: 366 or SEQ ID NO: 365.

11. The chimerical peptide according to the claim 1, wherein said cell penetrating peptide comprises region Ser376-Trp391 of the envelope protein from DV2 or a structurally equivalent segment from other serotype of dengue virus.

12. The chimerical peptide according to the claim 1, further comprising a signal of retention and/or localization in the endoplasmic reticulum wherein said signal increases the antiviral activity of the peptide.

13. The chimerical peptide according to the claim 1, wherein said peptide is lipidated and the lipidation increases the antiviral activity of the peptide.

14. A pharmaceutical composition comprising a pharmaceutically acceptable excipient and one or more peptides according to claim 1, said pharmaceutical composition being efficacious for treatment against infection by one or more viruses from the Flaviviridae family.

15. The chimerical peptide according to claim 9, wherein said Hepacivirus is HCV.

* * * * *

UNITED STATES PATENT AND TRADEMARK OFFICE

CERTIFICATE OF CORRECTION

PATENT NO. : 8,674,063 B2
APPLICATION NO. : 12/513085
DATED : March 18, 2014
INVENTOR(S) : Chinea Santiago et al.

It is certified that error appears in the above-identified patent and that said Letters Patent is hereby corrected as shown below:

IN THE SPECIFICATION:

Column 30, line 26

Now reads: "manner, with a 1050 of approximately 50-60 μM.";

Should read: -- manner, with a IC50 of approximately 50-60 μM. --.

Signed and Sealed this
Twelfth Day of August, 2014

Michelle K. Lee

*Deputy Director of the United States Patent and Trademark Office*